United States Patent
Chakravarty et al.

(10) Patent No.: US 9,629,850 B2
(45) Date of Patent: Apr. 25, 2017

(54) COMBINATION OF MEK INHIBITORS AND SELECTIVE INHIBITORS OF AURORA A KINASE

(75) Inventors: Arijit Chakravarty, Lexington, MA (US); Patrick Vincent, Encinitas, CA (US)

(73) Assignee: Millennium Pharmaceuticals, Inc., Cambridge, MA (US)

(*) Notice: Subject to any disclaimer, the term of this patent is extended or adjusted under 35 U.S.C. 154(b) by 0 days.

(21) Appl. No.: 14/122,779

(22) PCT Filed: Jun. 4, 2012

(86) PCT No.: PCT/US2012/040733
§ 371 (c)(1),
(2), (4) Date: Jul. 21, 2014

(87) PCT Pub. No.: WO2012/167247
PCT Pub. Date: Dec. 6, 2012

(65) Prior Publication Data
US 2014/0336180 A1    Nov. 13, 2014

Related U.S. Application Data

(60) Provisional application No. 61/493,217, filed on Jun. 3, 2011, provisional application No. 61/613,207, filed on Mar. 20, 2012.

(51) Int. Cl.
| | | |
|---|---|---|
| *A61K 31/19* | (2006.01) |
| *A61K 31/202* | (2006.01) |
| *A61K 31/198* | (2006.01) |
| *A61K 31/194* | (2006.01) |
| *A61K 31/55* | (2006.01) |
| *A61K 31/519* | (2006.01) |
| *A61K 45/06* | (2006.01) |

(52) U.S. Cl.
CPC ............ *A61K 31/55* (2013.01); *A61K 31/519* (2013.01); *A61K 45/06* (2013.01)

(58) Field of Classification Search
IPC .................. A61K 31/19,31/202, 31/98, 31/194
See application file for complete search history.

(56) References Cited

U.S. PATENT DOCUMENTS

| | | |
|---|---|---|
| 7,572,784 B2 | 8/2009 | Claiborne et al. |
| 8,026,246 B2 | 9/2011 | Claiborne et al. |
| 2008/0045501 A1 | 2/2008 | Claiborne et al. |
| 2010/0004247 A1 | 1/2010 | Mundt et al. |
| 2010/0227838 A1 | 9/2010 | Shah et al. |
| 2011/0312942 A1 | 12/2011 | Claiborne et al. |
| 2011/0312943 A1 | 12/2011 | Claiborne et al. |
| 2015/0166545 A1 | 6/2015 | Claiborne et al. |

FOREIGN PATENT DOCUMENTS

| | | |
|---|---|---|
| JP | 2010-510215 A | 4/2010 |
| JP | 2011-506420 A | 3/2011 |
| WO | WO-2005/111039 A2 | 11/2005 |
| WO | WO-2008/063525 A1 | 5/2008 |
| WO | WO-2008/079814 A2 | 7/2008 |
| WO | WO-2009/074827 A2 | 6/2009 |
| WO | WO 2009/114703 * | 9/2009 |

OTHER PUBLICATIONS

Dong et al. Bioorganic & Medicinal Chemistry Letters 21 (2011) 1315-1319.*
ClinicalTrials.gov (Sep. 2009).*
Carvajal, R.D. et al., Aurora Kinases: New Targets for Cancer Therapy, Clin. Cancer Res., 12:(23): 6869-6875 (2006).
Dotan, E. et al., The Ongoing Roll-out of Aurora Kinase Inhibitors in Cancer Treatment, Drugs of the Future, 35(10):845-858 (2010).
Extended European Search Report for EP12793812.4, 12 pages (Sep. 24, 2014).
International Preliminary Report on Patentability for PCT/US2012/040733, 5 pages (Dec. 4, 2013).
International Search Report for PCT/US2012/040733, 2 pages (Sep. 19, 2012).
PubChem CID No. 24771867, created May 5, 2008, modified Jun. 27, 2015, (5 pages).
Tseng et al., Aurora—A overexpression enhances cell-aggregation of Ha-ras transformants through the MEK/ERK signaling pathway, BMC Cancer, 9:435, 12 pages (2009).
Written Opinion for PCT/US2012/040733, 4 pages (Sep. 19, 2012).

* cited by examiner

*Primary Examiner* — Shirley V Gembeh
(74) *Attorney, Agent, or Firm* — Choate, Hall & Stewart LLP; Kristen C. Buteau, JD; Gang Wang, JD

(57) ABSTRACT

The present invention relates to methods for the treatment of proliferative disorders. In particular, the invention provides methods for treatment of proliferative disorders by administering a MEK inhibitor in combination with a selective inhibitor of Aurora A kinase.

6 Claims, 2 Drawing Sheets

COMBINATION OF MEK INHIBITORS AND SELECTIVE INHIBITORS OF AURORA A KINASE

PRIORITY CLAIM

This application is a 371 national phase of PCT/US2012/040733, filed Jun. 4, 2012, which claims priority from U.S. Provisional Patent Application Ser. No. 61/493,217, filed on Jun. 3, 2011, and U.S. Provisional Patent Application Ser. No. 61/613,207, filed on Mar. 20, 2012, each of which is hereby incorporated by reference in its entirety.

FIELD OF THE INVENTION

This invention relates to methods for the treatment of various cell proliferative disorders. In particular, the invention provides methods for treatment of various cell proliferative disorders by administering a MEK inhibitor in combination with a selective inhibitor of Aurora A kinase. The invention also provides pharmaceutical compositions and kits comprising a MEK inhibitor in combination with a selective Aurora A kinase inhibitor.

BACKGROUND OF THE INVENTION

Cancer is the second most common cause of death in the U.S. and accounts for one of every eight deaths worldwide. During 2010, the American Cancer Society estimated approximately 1,529,560 new cancer cases would be diagnosed in the U.S. alone, and an estimated 569,490 Americans would die from cancer. In 2008, an estimated 12.4 million new cancer cases were diagnosed, and 7.6 million people died from cancer worldwide. Although medical advances have improved cancer survival rates, there is a continuing need for new and more effective treatment.

Cancer is characterized by uncontrolled cell reproduction. The cell division cycle, which regulates the transition from quiescence to cell proliferation comprises four phases: G1, S phase (DNA synthesis), G2, and M phase (mitosis). Non-dividing cells rest in quiescent phase, G0. The cell division cycle also has several checkpoint mechanisms, which arrest the cell cycle and induce the transcription of genes that facilitate the repair of cell damage. Cell cycle checkpoints are regulatory pathways that control the order and timing of cell cycle transitions. The major cell cycle checkpoints include the DNA Damage Checkpoint, during phases G1 and G2, and the Spindle Assembly Checkpoint, during M phase. These checkpoints ensure that critical events such as DNA replication and chromosome segregation are completed in high fidelity.

Regulation of the cell cycle checkpoints is a critical determinant of the manner in which tumor cells respond to many chemotherapies and radiation. Many effective cancer therapies work by causing DNA damage; however, resistance to these agents remains a significant limitation in the treatment of cancer. One important mechanism leading to drug resistance is the activation of a checkpoint pathway that arrests the cell cycle to provide time for repair. Through this mechanism cell cycle progression is prevented, and immediate cell death of the damaged cell may be avoided.

The cell division cycle involves various protein kinases that are frequently overexpressed in cancer cells. Examples of such cell cycle kinases include (1) the G1/S phase kinases: the cyclin-dependent kinases (CDK2, CDK3, CDK4, CDK6, CDK7, and CDK9), and cell division cycle 7 kinase (CDC7); (2) the DNA damage checkpoint kinases: Ataxia-Telangiectasia Mutated kinase (ATM), ATM and Rad 3-related kinase (ATR), the checkpoint kinsases (CHK1 and CHK2), WEE1, and myelin transcription factor 1 (MYT1); and (3) the mitotic kinases: CDK1, NIMA-related kinase 2 (NEK2), polo like kinase 1 (PLK1), Aurora A kinase, Aurora B kinase, Aurora C kinase, the Budding Uninhibited by Benomyl kinases (BUB1, BUB1B—also known as BUBR1, and BUB3), and the kinetochore kinase TTK (also known as MPS1). (*Curr. Med. Chem.* (2007) 14, 969-985). Because of their important role in the cell division cycle, these cell cycle kinases have been explored as targets for cancer therapy.

The Aurora kinases, first identified in yeast (Ipl1), *Xenopus* (Eg2) and *Drosophila* (Aurora), are critical regulators of mitosis. (*Embo J* (1998) 17, 5627-5637; Genetics (1993) 135, 677-691; Cell (1995) 81, 95-105; *J Cell Sci* (1998) 111(Pt 5), 557-572). In humans, three isoforms of Aurora kinase exist, including Aurora A, Aurora B and Aurora C. Aurora A and Aurora B play critical roles in the normal progression of cells through mitosis, whereas Aurora C activity is largely restricted to meiotic cells. Aurora A and Aurora B are structurally closely related. Their catalytic domains lie in the C-terminus, where they differ in only a few amino acids. Greater diversity exists in their non-catalytic N-terminal domains. It is the sequence diversity in this region of Aurora A and Aurora B that dictates their interactions with distinct protein partners, allowing these kinases to have unique subcellular localizations and functions within mitotic cells.

Overexpression of Aurora B kinase has been reported in some cancers, and has been correlated to a worsened prognosis in some cancers. (*Mol Cancer Ther* (2007) 6, 1851-1857). Aurora B kinase localizes to the centromeres in preanaphase cells. There it plays a critical role in spindle bipolarity and the establishment and maintenance of the spindle assembly checkpoint. (*J Cell Biol* (2001) 153, 865-880; *J Cell Biol* (2003) 161, 267-280; *J Cell Biol* (2003) 161, 281-294; *Curr Biol* (2002) 12, 894-899). Cells lacking Aurora B kinase function demonstrate a loss of normal chromosome alignment during mitosis due to a fast-acting and potent override of the mitotic spindle checkpoint. During telophase, Aurora B kinase localizes to the spindle midzone and midbody, respectively. There, Aurora B kinase functions in cytokinesis. (*J Cell Biol* (2001) 152, 669-682; *Genes Cells* (2005) 10, 127-137). Inhibition of Aurora B kinase through the use of gene mutations, RNA interference or ATP competitive selective small molecule inhibitors leads to defects in the attachment of the spindle microtubules to kinetochores, chromosome segregation and formation of the cleavage furrow. (*J Cell Biol* (2001) 153, 865-880; *J Cell Biol* (2003) 161, 267-280; *J Cell Biol* (2001) 152, 669-682; *Mol Biol Cell* (2003) 14, 3325-3341; *Curr Biol* (2002) 12, 894-899; *Genes Cells* (2005) 10, 127-137). Aurora B kinase inhibition also prevents the proper formation of the spindle assembly checkpoint, causing cells to exit mitosis prematurely without a mitotic arrest and often without completing cytokinesis. (*J Cell Biol* (2003) 161, 267-280; *J Cell Biol* (2003) 161, 281-294). These cells enter the G1 portion of the cell cycle with double the amount of DNA, in a process known as endoreduplication. Reports in the literature suggest that this endoreduplication event is a prerequisite for the antiproliferative and antisurvival effects of Aurora B inhibition. This effect may be related to the phosphorylation of the Rb tumor suppressor protein by Aurora-B, which might contribute to the cell cycle arrest in the postmitotic G1 phase on unscheduled exit from mitosis. In agreement with this, it was found that endoreduplication, and thus apoptosis, after Aurora-B inhibition by ZM447439 is not dependent on p53. (*Mol Cancer Ther* (2009) 8(7), 2046-56).

Although Aurora B kinase and Aurora A kinase are both members of the Aurora kinase family, they have distinct roles during the process of mitotic division. In the course of normal mitotic cell division, cells organize bipolar spindles, with two radial arrays of microtubules each focused into a spindle pole at one end, and connected to chromosomes at the other end. In the instant before sister chromatids segregate into daughter cells, the chromosomes are arranged in a straight line (the 'metaphase plate'). This process of organizing bipolar mitotic spindles with fully aligned chromosomes serves to ensure the integrity of a cell's chromosomal complement during mitosis.

The Aurora A gene (AURKA) localizes to chromosome 20q13.2 which is commonly amplified or overexpressed at a high incidence in a diverse array of tumor types. (*Embo J*(1998) 17, 3052-3065; *Int J Cancer* (2006) 118, 357-363; *J Cell Biol* (2003) 161, 267-280; *Mol Cancer Ther* (2007) 6, 1851-1857; *J Natl Cancer Inst* (2002) 94, 1320-1329). Increased Aurora A gene expression has been correlated to the etiology of cancer and to a worsened prognosis. (*Int J Oncol* (2004) 25, 1631-1639; *Cancer Res* (2007) 67, 10436-10444; *Clin Cancer Res* (2004) 10, 2065-2071; *Clin Cancer Res* (2007) 13, 4098-4104; *Int J Cancer* (2001) 92, 370-373; *Br J Cancer* (2001) 84, 824-831; *J Natl Cancer Inst* (2002) 94, 1320-1329). This concept has been supported in experimental models, demonstrating that Aurora A overexpression leads to oncogenic transformation. (*Cancer Res* (2002) 62, 4115-4122; *Mol Cancer Res* (2009) 7, 678-688; *Oncogene* (2006) 25, 7148-7158; *Cell Res* (2006) 16, 356-366; *Oncogene* (2008) 27, 4305-4314; *Nat Genet* (1998) 20, 189-193). Overexpression of Aurora A kinase is suspected to result in a stoichiometric imbalance between Aurora A and its regulatory partners, leading to chromosomal instability and subsequent transforming events. The potential oncogenic role of Aurora A has led to considerable interest in targeting this kinase for the treatment of cancer.

As a key regulator of mitosis, Aurora A plays an essential role in mitotic entry and normal progression of cells through mitosis. (*Nat Rev Mol Cell Biol* (2003) 4, 842-854; *Curr Top Dev Biol* (2000) 49, 331-42; *Nat Rev Mol Cell Biol* (2001) 2(1), 21-32). During a normal cell cycle, Aurora A kinase is first expressed in the G2 stage where it localizes to centrosomes and functions in centrosome maturation and separation as well as in the entry of cells into mitosis. In mitotic cells Aurora A kinase predominantly localizes to centrosomes and the proximal portion of incipient mitotic spindles. There it interacts with and phosphorylates a diverse set of proteins that collectively function in the formation of mitotic spindle poles and spindles, the attachment of spindles to sister chromatid at the kinetochores, the subsequent alignment and separation of chromosome, the spindle assembly checkpoint and cytokinesis. (*J Cell Sci* (2007) 120, 2987-2996; *Trends Cell Biol* (1999) 9, 454-459; *Nat Rev Mol Cell Biol* (2003) 4, 842-854; *Trends Cell Biol* (2005) 15, 241-250).

Although selective inhibition of Aurora A kinase results in a delayed mitotic entry (*The Journal of biological chemistry* (2003) 278, 51786-51795), cells commonly enter mitosis despite having inactive Aurora A kinase. Cells in which Aurora A kinase has been selectively inhibited demonstrate a variety of mitotic defects including abnormal mitotic spindles (monopolar or multipolar spindles) and defects in the process of chromosome alignment. With time, monopolar and multipolar spindles may resolve to form two opposing spindle poles, although some of these defects may lead immediately to cell death via defective mitoses. While spindle defects resulting from Aurora A kinase inhibition induce mitotic delays, presumably through activation of the spindle assembly checkpoint, cells ultimately divide at a frequency near that of untreated cells. (*Mol Cell Biol* (2007) 27(12), 4513-25; *Cell Cycle* (2008) 7(17), 2691-704.; *Mol Cancer Ther* (2009) 8(7), 2046-56.). This inappropriate cell division occurs following a slow-acting suppression of the spindle assembly checkpoint due to loss of Aurora A kinase function. (Cell Cycle (2009) 8(6), 876-88). Bipolar spindles that are formed in the absence of Aurora A kinase function frequently show chromosome alignment and segregation defects, including chromosome congression defects at metaphase, lagging chromosomes at anaphase, and telophase bridges. Consistent with the chromosome segregation defects, cells treated with MLN8054, a selective inhibitor of Aurora A kinase, develop aneuploidy that increases over time. Subsequent to repeated passages through defective mitotic divisions, cells treated with MLN8054 will often undergo senescence, an irreversible growth arrest with distinctive morphological characteristics. (*Mol Cancer Res* (2010) 8(3), 373-84). In some cell lines, MLN8054-treated cells exit from mitosis and activate a p53-dependent postmitotic G1 checkpoint, which subsequently induces p21 and Bax, leading to G1 arrest followed by the induction of apoptosis. (*Mol. Cancer. Ther* (2009) 8(7), 2046-56). Some cells may also exit mitosis without cytokinesis. These cells enter the G1 phase of the cell cycle with double the normal DNA content and are therefore referred to as G1 tetraploid cells. Lastly, some cells may divide, albeit with severe chromosome segregation defects (*Mol Cell Biol* (2007) 27(12), 4513-25). In the latter two outcomes, the abnormal mitotic divisions result in deleterious aneuploidy leading to cell death or arrest. Alternatively, it is possible that a portion of these cells may be resistant to these terminal outcomes and can reenter the cell cycle, as aneuploidy has been demonstrated to be both a suppressor and a promoter of tumor cell growth.

Other targets for cancer therapy include the mitogen-activated protein kinase (MAPK) cascades, which are key signaling pathways involved in the regulation of normal cell proliferation, survival and differentiation. Of the known MAPK signaling pathways, the RAF-MEK-ERK pathway mediates proliferative and anti-apoptotic signaling from growth factors and oncogenic factors such as Ras and Raf mutant phenotypes that promote tumor growth, progression, and metastasis. Depending upon the stimulus and cell type, this pathway can transmit signals, which result in the prevention or induction of apoptosis or cell cycle progression.

Extracellular-signal-regulated kinase (ERK) is a downstream component of an evolutionarily conserved signaling module that is activated by the Raf serine/threonine kinases. Raf activates the MAP kinase ERK kinase (MEK)1/2 dual-specificity protein kinases, which then activate ERK1/2. Additionally, the Raf-MEK-ERK pathway is a key downstream effector of the Ras small GTPase. Ras is a key downstream effector of the epidermal growth factor receptor (EGFR). ERK activation also promotes upregulated expression of EGFR ligands, promoting an autocrine growth loop critical for tumor growth. Other signal transduction pathways, such as the PI3K/PTEN/Akt pathway, interact with the Raf/MEK/ERK pathway to regulate positively or negatively its activity, or to alter the phosphorylation status of downstream targets.

The frequent mutational activation of this pathway in human cancers points to an important role for this pathway in human oncogenesis. Ras small GTPase, the most frequently mutated oncogene in human cancers, is mutationally activated and/or overexpressed in a wide variety of human cancers. Abnormal activation of this pathway occurs in leukemia because of mutations at Ras as well as genes in other pathways which serve to regulate its activity. Raf and Erk are also frequently mutated in a number of different tumor types.

Constitutive action of MAPKs has been reported in >30% of primary tumor cell lines including cell lines derived from colon, lung, breast, pancreas, ovary, and kidney. (*Oncogene* (1999) 18, 813-822). Higher concentrations of active MAPK/ERK (pMAPK/pERK) have been detected in tumor tissue as compared to normal adjacent tissue. (*J. Clin. Invest.* (1997) 99, 1478-1483).

Inhibition of Ras/Raf/MEK activity has been shown to be accompanied by a cell cycle arrest at the G0-G1 boundary, as well as in some cases, apoptosis mediated by the down-regulation of the Bcl2 antiapoptotic protein, both of which act to block cell proliferation. A number of biochemical markers have been associated with this arrest, including upregulation of p21Waf1, p27Kip1, inhibition of cyclin/cyclin-dependent kinase 2 (cdk2) activity, accumulation of hypophosphorylated pRb, and inhibition of E2F activity. (*Cancer Res* (2005) 65(11), 4870-80).

Given the importance of the protein kinases involved in driving the cell cycle, it would be beneficial if more effective treatment regimens, which target these kinases could be developed. In particular, combined treatment regimens could be helpful for patients suffering from cell proliferative disorders, and might potentially even decrease the rate of relapse or overcome the resistance to a particular anticancer agent sometimes seen in these patients.

There is thus a need for new cancer treatment regimens, including combination therapies.

DETAILED DESCRIPTION OF THE INVENTION

Figure 1:
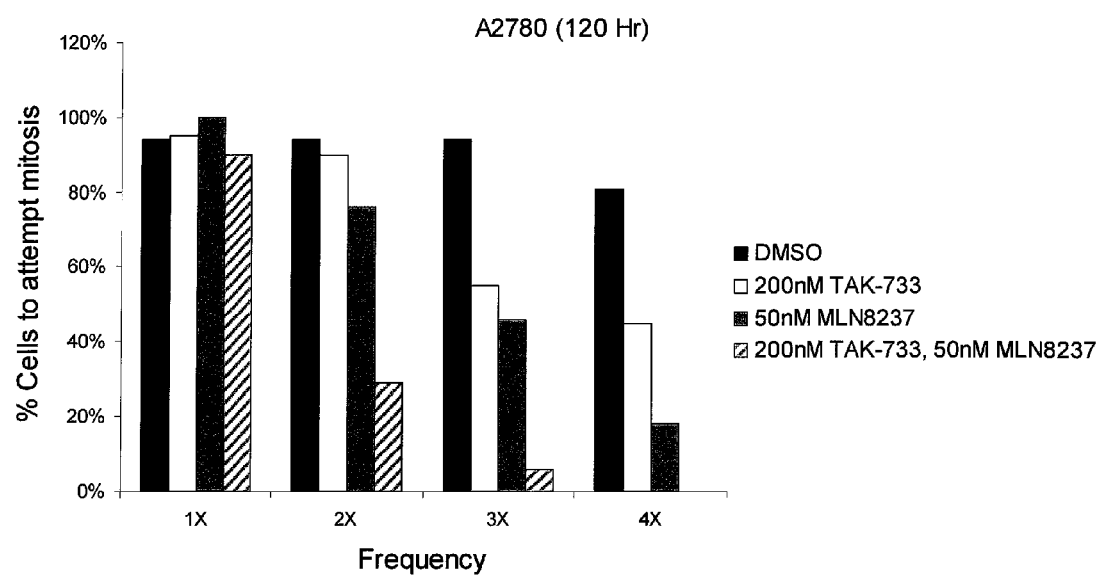
FIG. 1 Frequency of mitosis in A2780 cells treated with DMSO (black bars), 200 nM TAK-733 (white bars), 50 nM MLN8237 (gray bars), or 200 nM TAK-733 and 50 nM MLN8237 (hatched bars) continuously for 120 hours. Time lapse videos were generated from cell images taken at 5 minute intervals over 120 hours and the time of mitotic entry was recorded when adherent (interphase) cells rounded up from the bottom of the plate. In this paragraph, MLN8237 refers to the sodium salt, sodium 4-{[9-chloro-7-(2-fluoro-6-methoxyphenyl)-5H-pyrimido[5,4-d][2]benzazepin-2-yl]amino}-2-methoxybenzoate monohydrate, and TAK-733 refers to 3-[(2R)-2,3-dihydroxypropyl]-6-fluoro-5-[(2-fluoro-4-iodophenyl)amino]-8-methylpyrido[2,3-d]pyrimidine-4,7(3H,8H)-dione.

The present invention provides new combination therapies for the treatment of proliferative disorders. In particular, the present invention provides a method to treat a patient suffering from a proliferative disorder comprising administering to said patient a MEK inhibitor in combination with a selective inhibitor of Aurora A kinase, wherein the amounts of each inhibitor are therapeutically effective when used in combination. The invention also provides a MEK inhibitor in combination with a selective inhibitor of Aurora A kinase for use in the manufacture of a medicament for the treatment of a proliferative disorder, wherein the amounts of each inhibitor are therapeutically effective when used in combination. The invention also provides pharmaceutical compositions and kits comprising a MEK inhibitor in combination with a selective inhibitor of Aurora A kinase.

While single agent MEK inhibitors and single agent selective inhibitors of Aurora A kinase may prove effective in treating a certain number of patients and certain cancer types, the present inventors have surprisingly discovered that combined therapy with a MEK inhibitor and a selective inhibitor of Aurora A kinase offers benefits not achieved with either agent individually.

As described above, the canonical understanding of MEK inhibition is a complete arrest at the G0-G1 boundary of the cell cycle, which blocks cell proliferation. Contrary to this understanding, the present inventors have discovered that cells treated with a MEK inhibitor continue to cycle through one or more cell cycle events. This continued cell cycle division despite the inhibition of MEK occurs with abnormal cell cycle progression times, and altered rates of passage through the G1, S and G2/M phases. The inventors have also observed upregulation of DNA damage markers, and abnormal mitotic phenotypes in some cell types.

These observations are consistent with the reported role for MEK function in DNA repair and DNA damage checkpoint function. Without wishing to be bound by theory, the present inventors believe that MEK inhibition causes a reduction in cellular viability due to induction of cellular lesions related to compromise of DNA damage response and cell-cycle checkpoint function. These cellular lesions induce a slowing of cell cycle progression and induction of cell death or eventual growth arrest. In the immediate aftermath of MEK inhibitor treatment, the inventors report that cells continue to cycle for multiple rounds of cell division. This continued cycling phenotype of single agent MEK inhibitor treatment is unintuitive in light of the literature, and suggests that, in combination with a selective Aurora A inhibitor, MEK inhibitor treatment will provide added therapeutic benefit as normal cell cycle progression will be perturbed at multiple points without the activity of either agent precluding the activity of the other due to induction of an immediate cell-cycle block. By contrast, in the canonical view, a MEK inhibitor would not be expected to combine well with an Aurora A kinase inhibitor, as the complete, and immediate, cell cycle block thought to be induced by MEK inhibition would interfere with the ability of Aurora A kinase inhibition to reduce cellular viability via the induction of mitotic defects.

Definitions:

Terms used herein shall be accorded the following defined meanings, unless otherwise indicated.

As used herein, the term "MEK" refers to members of the MAPK kinase family, which are dual specificity enzymes that phosphorylate threonine and tyrosine residues within the activation loop of their MAP kinase substrates. Enzymes in this family include MEK1, MEK2, MEK3, MEK4, MEK5, MEK6, and MEK7.

The term "MEK inhibitor" or "inhibitor of MEK" is used to signify a compound which is capable of interacting with a MEK and inhibiting its enzymatic activity. Inhibiting MEK enzymatic activity means reducing the ability of MEK to phosphorylate a substrate peptide or protein. In various embodiments, such reduction of MEK activity is at least about 50%, at least about 75%, at least about 90%, at least about 95%, or at least about 99%. In various embodiments, the concentration of MEK inhibitor required to reduce MEK enzymatic activity is less than about 1 μM, less than about 500 nM, less than about 100 nM, or less than about 50 nM.

In some embodiments, such inhibition is selective, i.e., the MEK inhibitor reduces the ability of MEK to phosphorylate a substrate peptide or protein at a concentration that is lower than the concentration of the inhibitor that is required to produce another, unrelated biological effect, e.g., reduction of the enzymatic activity of a different kinase. In some embodiments, the MEK inhibitor also reduces the enzymatic activity of another kinase, preferably one that is implicated in cancer.

As used herein, the term "Aurora A kinase" refers to a serine/threonine kinases involved in mitotic progression. Aurora A kinase is also known as AIK, ARK1, AURA, BTAK, STK6, STK7, STK15, AURORA2, MGC34538, and AURKA. A variety of cellular proteins that play a role in cell division are substrates for phosphorylation by the Aurora A kinase enzyme, including, without limitation, p53, TPX-2, XIEg5 (in *Xenopus*), and D-TACC (in *Drosophila*). The Aurora A kinase enzyme is also itself a substrate for autophosphorylation, e.g., at Thr288. Preferably, the Aurora A kinase is a human Aurora A kinase.

The term "inhibitor of Aurora A kinase" or "Aurora A kinase inhibitor" is used to signify a compound that is capable of interacting with Aurora A kinase and inhibiting its enzymatic activity. Inhibiting Aurora A kinase enzymatic activity means reducing the ability of Aurora A kinase to phosphorylate a substrate peptide or protein. In various embodiments, such reduction of Aurora A kinase activity is at least about 75%, at least about 90%, at least about 95%, or at least about 99%. In various embodiments, the concentration of Aurora A kinase inhibitor required to reduce an Aurora A kinase enzymatic activity is less than about 1 μM, less than about 500 nM, less than about 100 nM, or less than about 50 nM. Preferably, the concentration that is required to inhbit the enzymatic activity of Aurora A kinase is lower than the concentration of the inhibitor that is required to inhibit the enzymatic activity of Aurora B kinase. In various embodiments, the concentration of an Aurora A kinase inhibitor that is required to reduce Aurora A kinase enzymatic activity is at least about 2-fold, at least about 5-fold, at least about 10-fold, at least about 20-fold, at least about 50-fold, at least about 100-fold, at least about 500-fold, or at least about 1000-fold lower than the concentration of the inhibitor that is required to reduce Aurora B kinase enzymatic activity.

Inhibition of Aurora A and inhibition of Aurora B result in markedly different cellular phenotypes. (*Proc. Natl. Acad. Sci.* (2007) 104: 4106; *Mol Cancer Ther* (2009) 8(7), 2046-56; *Chem. Biol.* (2008) 15(6) 552-62). For example, inhibition of Aurora A in the absence of Aurora B inhibition results in increased mitotic index as measured by quantifying phosphorylated histone H3 on serine 10 (pH is H3). pHisH3 is a unique substrate of Aurora B in physiological systems (e.g. intact cells). By contrast, inhibition of Aurora B or dual inhibition of Aurora A and Aurora B results in a decrease in pH is H3. Accordingly, as used herein, the term "selective inhibitor of Aurora A kinase" or "selective Aurora A kinase inhibitor" refers to an inhibitor that exhibits an Aurora A kinase inhibitor phenotype at effective antitumor concentrations. In some embodiments, the selective Aurora A kinase inhibitor causes a transient mitotic delay, as measured by quantification of pH is H3, when administered to mice at a dose where the free fraction adjusted concentration ($C_{ave}$) in plasma is equivalent to the free fraction adjusted concentration achieved in plasma in humans at the maximum tolerated dose (MTD). As used herein, "free fraction adjusted concentration" refers to the plasma concentration of free drug (not protein bound).

As used herein, the term "in combination" refers to use of both a MEK inhibitor and a selective Aurora A kinase inhibitor in the treatment of the same disease or condition in the same patient. As further described below, unless explicitly specified, the term "in combination" does not restrict the timing of administration of the MEK inhibitor and selective Aurora A kinase inhibitor.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

As used herein, the term "comprises" means "includes, but is not limited to."

The term "aliphatic" or "aliphatic group", as used herein, means a substituted or unsubstituted straight-chain, branched or cyclic $C_{1-12}$ hydrocarbon, which is completely saturated or which contains one or more units of unsaturation, but which is not aromatic. For example, suitable aliphatic groups include substituted or unsubstituted linear, branched or cyclic alkyl, alkenyl, alkynyl groups and hybrids thereof, such as (cylcoalkyl)alkyl, (cycloalkenyl)alkyl or (cycloalkyl)alkenyl.

The terms "alkyl", "alkenyl", and "alkynyl", used alone or as part of a larger moiety, refer to a straight and branched chain aliphatic group having from 1 to 12 carbon atoms. For purposes of the present invention, the term "alkyl" will be used when the carbon atom attaching the aliphatic group to the rest of the molecule is a saturated carbon atom. However, an alkyl group may include unsaturation at other carbon atoms. Thus, alkyl groups include, without limitation, methyl, ethyl, propyl, allyl, propargyl, butyl, pentyl, and hexyl.

For purposes of the present invention, the term "alkenyl" will be used when the carbon atom attaching the aliphatic group to the rest of the molecule forms part of a carbon-carbon double bond. Alkenyl groups include, without limitation, vinyl, 1-propenyl, 1-butenyl, 1-pentenyl, and 1-hexenyl.

For purposes of the present invention, the term "alkynyl" will be used when the carbon atom attaching the aliphatic group to the rest of the molecule forms part of a carbon-carbon triple bond. Alkynyl groups include, without limitation, ethynyl, 1-propynyl, 1-butynyl, 1-pentynyl, and 1-hexynyl.

The term "cycloaliphatic", used alone or as part of a larger moiety, refers to a saturated or partially unsaturated cyclic aliphatic ring system having from 3 to about 14 members, wherein the aliphatic ring system is optionally substituted. In some embodiments, the cycloaliphatic is a monocyclic hydrocarbon having 3-8 or 3-6 ring carbon atoms. Nonlimiting examples include cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloaliphatic is a bridged or fused bicyclic hydrocarbon having 6-12, 6-10, or 6-8 ring carbon atoms, wherein any individual ring in the bicyclic ring system has 3-8 members.

In some embodiments, two adjacent substituents on the cycloaliphatic ring, taken together with the intervening ring atoms, form an optionally substituted fused 5- to 6-membered aromatic or 3- to 8-membered non-aromatic ring having 0-3 ring heteroatoms selected from the group consisting of O, N, and S. Thus, the term "cycloaliphatic" includes aliphatic rings that are fused to one or more aryl, heteroaryl, or heterocyclyl rings. Nonlimiting examples include indanyl, 5,6,7,8-tetrahydroquinoxalinyl, decahydronaphthyl, or tetrahydronaphthyl, where the radical or point of attachment is on the aliphatic ring. The term "cycloaliphatic" may be used interchangeably with the terms "carbocycle", "carbocyclyl", "carbocyclo", or "carbocyclic".

"Cycloalkyl" means a non-aromatic, saturated or partially unsaturated, monocyclic, bicyclic or polycyclic ring assembly. $(C_X)$cycloalkyl and $(C_{X-Y})$cycloalkyl are typically used where X and Y indicate the number of carbon atoms in the ring assembly. For example, $(C_{3-10})$cycloalkyl includes cyclopropyl, cyclobutyl, cyclopentyl, cyclohexyl, cyclohexenyl, 2,5-cyclohexadienyl, bicyclo[2.2.2]octyl, adamantan-1-yl, decahydronaphthyl, oxocyclohexyl, dioxocyclohexyl, thiocyclohexyl, 2-oxobicyclo[2.2.1]hept-1-yl, and the like. In particular embodiments, "cycloalkyl," either alone or represented along with another radical, can be a $(C_{3-14})$ cycloalkyl, a $(C_{3-10})$cycloalkyl, a $(C_{3-7})$cycloalkyl, a $(C_{8-10})$ cycloalkyl or a $(C_{5-7})$cycloalkyl. Alternatively, "cycloalkyl," either alone or represented along with another radical, can be a $(C_5)$cycloalkyl, a $(C_6)$cycloalkyl, a $(C_7)$cycloalkyl, a $(C_8)$ cycloalkyl, a $(C_9)$cycloalkyl or a $(C_{10})$cycloalkyl.

"Bicycloalkyl" means a saturated or partially unsaturated fused, spiro or bridged bicyclic ring assembly. In particular embodiments, "bicycloalkyl," either alone or represented along with another radical, can be a $(C_{4-15})$bicycloalkyl, a $(C_{4-10})$bicycloalkyl, a $(C_{1-10})$bicycloalkyl or a $(C_{8-10})$bicycloalkyl. Alternatively, "bicycloalkyl," either alone or represented along with another radical, can be a $(C_8)$bicycloalkyl, a $(C_9)$bicycloalkyl or a $(C_{10})$bicycloalkyl.

"Bicycloaryl" means a fused, spiro or bridged bicyclic ring assembly wherein at least one of the rings comprising the assembly is aromatic. $(C_X)$bicycloaryl and $(C_{X-Y})$bicycloaryl are typically used where X and Y indicate the number of carbon atoms in the bicyclic ring assembly and directly attached to the ring. In particular embodiments, "bicycloaryl," either alone or represented along with another radical, can be a (a $(C_{4-15})$bicycloaryl, a $(C_{4-10})$bicycloaryl, a $(C_{6-10})$bicycloaryl or a $(C_{8-10})$bicycloaryl. Alternatively, "bicycloalkyl," either alone or represented along with another radical, can be a $(C_8)$bicycloaryl, a $(C_9)$bicycloaryl or a $(C_{10})$bicycloaryl.

The terms "aryl" and "ar-", used alone or as part of a larger moiety, e.g., "aralkyl", "aralkoxy", or "aryloxyalkyl", refer to a $C_6$ to $C_{14}$ aromatic hydrocarbon, comprising one to three rings, each of which is optionally substituted. Preferably, the aryl group is a $C_{6-10}$ aryl group. Aryl groups include, without limitation, phenyl, naphthyl, and anthracenyl. In some embodiments, two adjacent substituents on the aryl ring, taken together with the intervening ring atoms, form an optionally substituted fused 5- to 6-membered aromatic or 4- to 8-membered non-aromatic ring having 0-3 ring heteroatoms selected from the group consisting of O, N, and S. Thus, the term "aryl", as used herein, includes groups in which an aromatic ring is fused to one or more heteroaryl, cycloaliphatic, or heterocyclyl rings, where the radical or point of attachment is on the aromatic ring. Nonlimiting examples of such fused ring systems include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, tetrahydroquinolinyl, tetrahydroisoquinolinyl, fluorenyl, indanyl, phenanthridinyl, tetrahydronaphthyl, indolinyl, phenoxazinyl, benzodioxanyl, and benzodioxolyl. An aryl group may be mono-, bi-, tri-, or polycyclic, preferably mono-, bi-, or tricyclic, more preferably mono- or bicyclic. The term "aryl" may be used interchangeably with the terms "aryl group", "aryl moiety", and "aryl ring".

An "aralkyl" or "arylalkyl" group comprises an aryl group covalently attached to an alkyl group, either of which independently is optionally substituted. Preferably, the aralkyl group is $C_{6-10}$ aryl($Cl_{1-6}$)alkyl, $C_{6-10}$ aryl($C_{1-4}$)alkyl, or $C_{6-10}$ aryl($C_{1-3}$)alkyl, including, without limitation, benzyl, phenethyl, and naphthylmethyl.

The terms "heteroaryl" and "heteroar-", used alone or as part of a larger moiety, e.g., heteroaralkyl, or "heteroaralkoxy", refer to groups having 5 to 14 ring atoms, preferably 5, 6, 9, or 10 ring atoms; having 6, 10, or 14 π electrons shared in a cyclic array; and having, in addition to carbon atoms, from one to four heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, two adjacent substituents on the heteroaryl, taken together with the intervening ring atoms, form an optionally substituted fused 5- to 6-membered aromatic or 4- to 8-membered non-aromatic ring having 0-3 ring heteroatoms selected from the group consisting of O, N, and S. Thus, the terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono-, bi-, tri-, or polycyclic, preferably mono-, bi-, or tricyclic, more preferably mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 3- to 7-membered monocyclic, or to a fused 7- to 10-membered or bridged 6- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a heterocyclyl ring having 1-3 heteroatoms selected from oxygen, sulfur or nitrogen, the nitrogen may be N (as in 3,4-dihydro-2H-pyrrolyl), NH (as in pyrrolidinyl) or $^+$NR (as in N-substituted pyrrolidinyl). A heterocyclic ring can be attached to its pendant group at any heteroatom or carbon atom that results in a stable structure, and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl.

In some embodiments, two adjacent substituents on a heterocyclic ring, taken together with the intervening ring atoms, for an optionally substituted fused 5- to 6-membered aromatic or 3- to 8-membered non-aromatic ring having 0-3 ring heteroatoms selected from the group consisting of O, N, and S. Thus, the terms "heterocycle", "heterocyclyl", "heterocyclyl ring", "heterocyclic group", "heterocyclic moiety", and "heterocyclic radical", are used interchangeably herein, and include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond between ring atoms. The term "partially unsaturated" is intended to encompass rings having multiple sites of unsaturation, but is not intended to include aryl or heteroaryl moieties, as herein defined.

The terms "haloaliphatic", "haloalkyl", "haloalkenyl" and "haloalkoxy" refer to an aliphatic, alkyl, alkenyl or alkoxy group, as the case may be, which is substituted with one or more halogen atoms. As used herein, the term "halogen" or "halo" means F, Cl, Br, or I. The term "fluoroaliphatic" refers to a haloaliphatic wherein the halogen is fluoro.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms is replaced with a substituent. Suitable substituents include those described below for a substituted aliphatic group. An alkylene chain also may be substituted at one or more positions with an aliphatic group or a substituted aliphatic group.

"Amino" means a nitrogen moiety having two further substituents where, for example, a hydrogen or carbon atom is attached to the nitrogen. For example, representative amino groups include —NH$_2$, —NHCH$_3$, —N(CH$_3$)$_2$, —NH((C$_{1-10}$)alkyl), —N((C$_{1-10}$)alkyl)$_2$, —NH(aryl), —NH(heteroaryl), —N(aryl)$_2$, —N(heteroaryl)$_2$, and the like. Optionally, the two substituents together with the nitrogen may also form a ring. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Carbonyl" means the radical —C(=O)— and/or —C(=O)R, wherein R is hydrogen or a further substituent. It is noted that the carbonyl radical may be further substituted with a variety of substituents to form different carbonyl groups including acids, acid halides, aldehydes, amides, esters, and ketones.

"Carboxy" means the radical —C(=O)—O— and/or —C(=O)—OR, wherein R is hydrogen or a further substituent. It is noted that compounds of the invention containing carboxy moieties may include protected derivatives thereof, i.e., where the oxygen is substituted with a protecting group. Suitable protecting groups for carboxy moieties include benzyl, tert-butyl, and the like.

"Cyano" means the radical —CN.

"Nitro" means the radical —NO$_2$.

"Hydroxy" means the radical —OH.

"Imino" means the radical —CR(=NR') and/or —C(=NR')—, wherein R and R' are each independently hydrogen or a further substituent.

"Oxy" means the radical —O— or —OR, wherein R is hydrogen or a further substituent. Accordingly, it is noted that the oxy radical may be further substituted with a variety of substituents to form different oxy groups including hydroxy, alkoxy, aryloxy, heteroaryloxy or carbonyloxy.

"Sulfinyl" means the radical —SO— and/or —SO—R, wherein R is hydrogen or a further substituent. It is noted that the sulfinyl radical may be further substituted with a variety of substituents to form different sulfinyl groups including sulfinic acids, sulfinamides, sulfinyl esters, and sulfoxides.

"Sulfonyl" means the radical —SO$_2$— and/or —SO$_2$—R, wherein R is hydrogen or a further substituent. It is noted that the sulfonyl radical may be further substituted with a variety of substituents to form different sulfonyl groups including sulfonic acids, sulfonamides, sulfonate esters, and sulfones.

"Thio" denotes replacement of an oxygen by a sulfur and includes, but is not limited to, —SR, —S— and =S containing groups.

"Thioalkyl" means an alkyl, as defined above, except where one or more of the carbon atoms forming the alkyl chain are replaced with sulfur atoms (—S— or —S—R, wherein R is hydrogen or a further substituent). For example, a thio(C$_{1-10}$)alkyl refers to a chain comprising between 1 and 10 carbons and one or more sulfur atoms.

"Thiocarbonyl" means the radical —C(=S)— and/or —C(=S)—R, wherein R is hydrogen or a further substituent. It is noted that the thiocarbonyl radical may be further substituted with a variety of substituents to form different thiocarbonyl groups including thioacids, thioamides, thioesters, and thioketones.

"Substituent convertible to hydrogen in vivo" means any group that is convertible to a hydrogen atom by enzymological or chemical means including, but not limited to, hydrolysis and hydrogenolysis. Examples include hydrolyzable groups, such as acyl groups, groups having an oxycarbonyl group, amino acid residues, peptide residues, o-nitrophenylsulfenyl, trimethylsilyl, tetrahydro-pyranyl, diphenylphosphinyl, and the like. Examples of acyl groups include formyl, acetyl, trifluoroacetyl, and the like. Examples of groups having an oxycarbonyl group include ethoxycarbonyl, t-butoxycarbonyl [(CH$_3$)$_3$C—OCO—], benzyloxycarbonyl, p-methoxybenzyloxycarbonyl, vinyloxycarbonyl, β-(p-toluenesulfonyl)ethoxycarbonyl, and the like. Examples of suitable amino acid residues include amino acid residues per se and amino acid residues that are protected with a protecting group. Suitable amino acid residues include, but are not limited to, residues of Gly (glycine), Ala (alanine; $CH_3CH(NH_2)CO-$), Arg (arginine), Asn (asparagine), Asp (aspartic acid), Cys (cysteine), Glu (glutamic acid), His (histidine), Ile (isoleucine), Leu (leucine; $(CH_3)_2CHCH_2CH(NH_2)CO-$), Lys (lysine), Met (methionine), Phe (phenylalanine), Pro (proline), Ser (serine), Thr (threonine), Trp (tryptophan), Tyr (tyrosine), Val (valine), Nva (norvaline), Hse (homoserine), 4-Hyp (4-hydroxyproline), 5-Hyl (5-hydroxylysine), Orn (ornithine) and β-Ala. Examples of suitable protecting groups include those typically employed in peptide synthesis, including acyl groups (such as formyl and acetyl), arylmethyloxycarbonyl groups (such as benzyloxycarbonyl and p-nitrobenzyloxycarbonyl), t-butoxycarbonyl groups [$(CH_3)_3C-OCO-$], and the like. Suitable peptide residues include peptide residues comprising two to five, and optionally two to three, of the aforesaid amino acid residues. Examples of such peptide residues include, but are not limited to, residues of such peptides as Ala-Ala [$CH_3CH(NH_2)CO-NHCH(CH_3)CO-$], Gly-Phe, Nva-Nva, Ala-Phe, Gly-Gly, Gly-Gly-Gly, Ala-Met, Met-Met, Leu-Met and Ala-Leu. The residues of these amino acids or peptides can be present in stereochemical configurations of the D-form, the L-form or mixtures thereof. In addition, the amino acid or peptide residue may have an asymmetric carbon atom. Examples of suitable amino acid residues having an asymmetric carbon atom include residues of Ala, Leu, Phe, Trp, Nva, Val, Met, Ser, Lys, Thr and Tyr. Peptide residues having an asymmetric carbon atom include peptide residues having one or more constituent amino acid residues having an asymmetric carbon atom. Examples of suitable amino acid protecting groups include those typically employed in peptide synthesis, including acyl groups (such as formyl and acetyl), arylmethyloxycarbonyl groups (such as benzyloxycarbonyl and p-nitrobenzyloxycarbonyl), t-butoxycarbonyl groups [$(CH_3)_3C-OCO-$], and the like. Other examples of substituents "convertible to hydrogen in vivo" include reductively eliminable hydrogenolyzable groups. Examples of suitable reductively eliminable hydrogenolyzable groups include, but are not limited to, arylsulfonyl groups (such as o-toluenesulfonyl); methyl groups substituted with phenyl or benzyloxy (such as benzyl, trityl and benzyloxymethyl); arylmethoxycarbonyl groups (such as benzyloxycarbonyl and o-methoxy-benzyloxycarbonyl); and halogenoethoxycarbonyl groups (such as β,β,β-trichloroethoxycarbonyl and β-iodoethoxycarbonyl).

A compound having a formula that is represented with a dashed bond is intended to include the formulae optionally having zero, one or more double bonds, as exemplified and shown below:

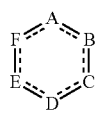

represents

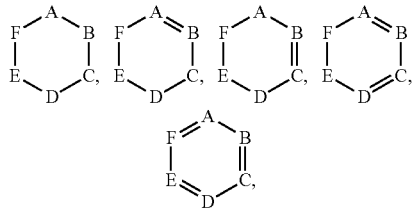

etc.

The term "substituted", as used herein, means that a hydrogen radical of the designated moiety is replaced with the radical of a specified substituent, provided that the substitution results in a stable or chemically feasible compound. The phrase "one or more substituents", as used herein, refers to a number of substituents that equals from one to the maximum number of substituents possible based on the number of available bonding sites, provided that the above conditions of stability and chemical feasibility are met. Unless otherwise indicated, an optionally substituted group may have a substituent at each substitutable position of the group, and the substituents may be either the same or different.

An aryl (including the aryl moiety in aralkyl, aralkoxy, aryloxyalkyl and the like) or heteroaryl (including the heteroaryl moiety in heteroaralkyl and heteroaralkoxy and the like) group may contain one or more substituents. Examples of suitable substituents on the unsaturated carbon atom of an aryl or heteroaryl group include -halo, $-NO_2$, $-CN$, $-R^*$, $-C(R^*)=C(R^*)_2$, $-C\equiv C-R^*$, $-OR^*$, $-SR^\circ$, $-S(O)R^\circ$, $-SO_2R^\circ$, $-SO_3R^\circ$, $-SO_2N(R^+)_2$, $-N(R^+)_2$, $-NR^+C(O)R^*$, $-NR^+C(O)N(R^+)_2$, $-NR^+CO_2R^\circ$, $-O-CO_2R^*$, $-OC(O)N(R^+)_2$, $-O-C(O)R^*$, $-CO_2R^*$, $-C(O)-C(O)R^*$, $-C(O)R^*$, $-C(O)N(R^+)_2$, $-C(O)N(R^+)C(=NR^+)-N(R^+)_2$, $-N(R^+)C(=NR^+)-N(R^+)-C(O)R^*$, $-C(=NR^+)-N(R^+)_2$, $-C(=NR^+)-OR^*$, $-N(R^+)-N(R^+)_2$, $-N(R^+)C(=NR^+)-N(R^+)_2$, $-NR^+SO_2R^\circ$, $-NR^+SO_2N(R^+)_2$, $-P(O)(R^*)_2$, $-P(O)(OR^*)_2$, $-O-P(O)-OR^*$, and $-P(O)(NR^+)-N(R^+)_2$; or two adjacent substituents, taken together with their intervening atoms, form a 5-6 membered unsaturated or partially unsaturated ring having 0-3 ring atoms selected from the group consisting of N, O, and S.

An aryl (including the aryl moiety in aralkyl, aralkoxy, aryloxyalkyl and the like) or heteroaryl (including the heteroaryl moiety in heteroaralkyl and heteroaralkoxy and the like) group may contain one or more substituents. Examples of suitable substituents on the unsaturated carbon atom of an aryl or heteroaryl group include -halo, $-NO_2$, $-CN$, $-R^*$, $-C(R^*)=C(R^*)_2$, $-C\equiv C-R^*$, $-OR^*$, $-SR^\circ$, $-S(O)R^\circ$, $-SO_2R$, $-SO_3R^\circ$, $-SO_2N(R^+)_2$, $-N(R^+)_2$, $-NR^+C(O)R^*$, $-NR^+C(O)N(R^+)_2$, $-NR^+CO_2R^\circ$, $-O-CO_2R^*$, $-OC(O)N(R^+)_2$, $-O-C(O)R^*$, $-CO_2R^*$, $-C(O)-C(O)R^*$, $-C(O)R^*$, $-C(O)N(R^+)_2$, $-C(O)N(R^+)C(=NR^+)-N(R^+)_2$, $-N(R^+)C(=NR^+)-N(R^+)-C(O)R^*$, $-C(=NR^+)-N(R^+)_2$, $-C(=NR^+)-OR^*$, $-N(R^+)-N(R^+)_2$, $-N(R^+)C(=NR^+)-N(R^+)_2$, $-NR^+SO_2R^\circ$, $-NR^+SO_2N(R^+)_2$, $-P(O)(R^*)_2$, $-P(O)(OR^*)_2$, $-O-P(O)-OR^*$, and $-P(O)(NR^+)-N(R^+)_2$; or two adjacent substituents, taken together with their intervening atoms, form a 5-6 membered unsaturated or partially unsaturated ring having 0-3 ring atoms selected from the group consisting of N, O, and S.

Each $R^+$, independently, is hydrogen or an optionally substituted aliphatic, aryl, heteroaryl, or heterocyclyl group, or two R+ on the same nitrogen atom, taken together with the nitrogen atom, form a 5-8 membered aromatic or non-aromatic ring having, in addition to the nitrogen atom, 0-2 ring heteroatoms selected from N, O, and S. Each R* independently is hydrogen or an optionally substituted aliphatic, aryl, heteroaryl, or heterocyclyl group. Each R° is an optionally substituted aliphatic or aryl group.

An aliphatic group or a non-aromatic heterocyclic ring may be substituted with one or more substituents. Examples of suitable substituents on the saturated carbon of an aliphatic group or of a non-aromatic heterocyclic ring include, without limitation, those listed above for the unsaturated carbon of an aryl or heteroaryl group and the following: =O, =S, =C(R*)$_2$, =N—N(R*)$_2$, =N—OR*, =N—NHC(O)R*, =N—NHCO$_2$R°, =N—NHSO$_2$R°, or =N—R*, where each R* and R° is as defined above.

Suitable substituents on the nitrogen atom of a non-aromatic heterocyclic ring include —R*, —N(R*)$_2$, —C(O) R*, —CO$_2$R*, —C(O)—C(O)R*—C(O)CH$_2$C(O)R*, —SO$_2$R*, —SO$_2$N(R*)$_2$, —C(=S)N(R*)$_2$, —C(=NH)— N(R*)$_2$, and —NR*SO$_2$R*; wherein each R* is as defined above.

Unless otherwise stated, structures depicted herein are meant to include compounds which differ only in the presence of one or more isotopically enriched atoms. For example, compounds having the present structure except for the replacement of a hydrogen atom by a deuterium or tritium, or the replacement of a carbon atom by a $^{13}$C— or $^{14}$C-enriched carbon are within the scope of the invention.

It will be apparent to one skilled in the art that certain compounds described herein may exist in tautomeric forms, all such tautomeric forms of the compounds being within the scope of the invention. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Any molecule capable of inhibiting the enzymatic activity of MEK may be used in the methods, pharmaceutical compositions, and kits of the present invention. In some embodiments the MEK inhibitor is a small molecular weight compound. Examples of such compounds include, but are not limited to, compounds disclosed in WO 08/079,814, WO 10/059,503, and U.S. Application No. 61/477,196, filed Apr. 20, 2011, all of which are hereby incorporated by reference in their entirety, 3-[(2R)-2,3-dihydroxypropyl]-6-fluoro-5-[(2-fluoro-4-iodophenyl)amino]-8-methylpyrido[2,3-d]pyrimidine-4,7(3H,8H)-dione (TAK-733), PD98059, U0126, Ro 09-2210, CI-1040 (Pfizer—formerly PD184352), PD0325901 (Pfizer), AZD6244 (Array BioPharma/AstraZeneca—formerly ARRY-142886), GDC-0973 (Exelixis/Genentech—formerly XL518), AR-119/RDEA119 (Ardea Biosciences/Bayer—formerly BAY 869766), GSK1120212 (GlaxoSmithKline), AZD8330 (Array BioPharma/AstraZeneca), RO5126766, RO4987655, RO4927350, RO5068760 (Hoffmann La Roche), AS703026, AS-701173, and AS-701255 (EMD Serono). Also suitable for use in the methods, pharmaceutical compositions, and kits of the invention are solvated and hydrated forms of any of these compounds. Also suitable for use in the methods, pharmaceutical compositions, and kits of the invention are pharmaceutically acceptable salts of any of the compounds, and solvated and hydrated forms of such salts. These MEK inhibitors can be prepared in a number of ways well known to one skilled in the art of organic synthesis, including, but not limited to, the methods of synthesis described in detail in the references referred to herein.

In some embodiments the MEK inhibitor of the present invention is an ATP-competitive MEK inhibitor, a non-ATP competitive MEK inhibitor, or an ATP-uncompetitive MEK inhibitor. In certain embodiments, the MEK inhibitor is a non-ATP competitive allosteric inhibitor. In other embodiments the MEK inhibitor inhibits gene expression, for example by interfering with mRNA stability or translation. In some other embodiments the MEK inhibitor is small interfering RNA (siRNA), also known as short interfering RNA, silencing RNA, short hairpin RNA (shRNA), or small hairpin RNA.

MEK inhibitors can be assayed in vitro or in vivo for their ability to selectively bind to and/or inhibit MEK. In vitro assays include assays to determine selective inhibition of the ability of MEK to phosphorylate a substrate protein or peptide. Alternate in vitro assays quantitate the ability of the compound to selectively bind to MEK. Selective inhibitor binding may be measured by radiolabelling the inhibitor prior to binding, isolating the inhibitor/MEK complex and determining the amount of radiolabel bound. Alternatively, selective inhibitor binding may be determined by running a competition experiment in which new inhibitors are incubated with MEK bound to a known radioligand. The compounds also can be assayed for their ability to affect cellular or physiological functions mediated by MEK activity. Assays for each of these activities are known in the art.

In some embodiments, the MEK inhibitor is a compound represented by formula (I):

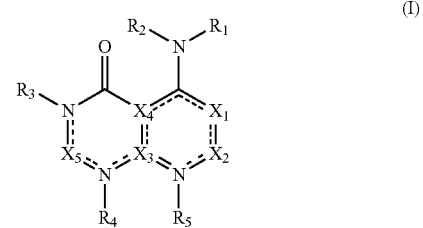

or a pharmaceutically acceptable salt thereof;
wherein:
$X_1$ and $X_2$ are each independently selected from the group consisting of $CR_6R_7$, CO, CS and $NR_8$;
$X_3$ and $X_4$ are each independently selected from the group consisting of $CR_7$ and N;
$X_5$ is selected from the group consisting of $CR_6R_7$, CS and $NR_8$;
$R_1$ is selected from the group consisting of $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;
$R_2$ is hydrogen or a substituent convertible in vivo to hydrogen;
$R_3$ is selected from the group consisting of hydrogen, oxy, hydroxy, carbonyloxy, alkoxy, hydroxyalkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, amino$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$ alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, provided that $R_3$ is absent when the atom to which it is bound forms part of a double bond;

$R_4$ is selected from the group consisting of hydrogen, oxy, hydroxy, carbonyloxy, $(C_{1-10})$alkoxy, $(C_{4-12})$aryloxy, hetero$(C_{1-10})$aryloxy, carbonyl, oxycarbonyl, amino, $(C_{1-10})$alkylamino, sulfonamido, amido, $(C_{1-10})$alkylamido, imino, sulfonyl, sulfinyl, $(C_{1-10})$alkyl, halo$(C_{1-10})$alkyl, hydroxy$(C_{1-10})$alkyl, amido$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, provided that $R_4$ is absent when the atom to which it is bound forms part of a double bond;

$R_5$ is selected from the group consisting of hydrogen, oxy, hydroxy, carbonyloxy, alkoxy, aryloxy, heteroaryloxy, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_5$ and $R_4$ are taken together to form a substituted or unsubstituted ring, provided that $R_5$ is absent when the atom to which it is bound forms part of a double bond;

$R_6$ and $R_7$ are each independently selected from the group consisting of hydrogen, halo, cyano, heteroaryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$Cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_7$ and $R_5$ are taken together to form a substituted or unsubstituted ring, provided that $R_7$ is absent when the atom to which it is bound forms part of a double bond; and $R_8$ is selected from the group consisting of hydrogen, oxy, hydroxy, carbonyloxy, $(C_{1-10})$alkoxy, $(C_{4-12})$aryloxy, hetero$(C_{1-10})$aryloxy, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, provided that $R_8$ is absent when the atom to which it is bound forms part of a double bond.

In some other embodiments, the MEK inhibitor is a compound represented by formula (IA):

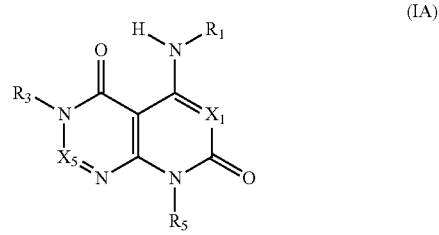

(IA)

or a tautomer, enantiomer, or pharmaceutically acceptable salt thereof, wherein $X_1$ is $CR_6$;

$X_5$ is $CR_6$;

$R_1$ is $(C_{4-12})$aryl unsubstituted or substituted with one or more substituents through available valencies selected from the group consisting of halo; nitro; cyano; thio having a substituent selected from the group consisting of hydrogen and $(C_{1-10})$alkyl; hydroxy; $(C_{1-10})$alkoxy itself optionally having a substituent selected from the group consisting of halo, nitro, cyano, hydroxy, $(C_{1-10})$alkoxy, amino, $(C_{3-12})$cycloalkyl, and $(C_{4-12})$aryl; $(C_{4-12})$aryloxy; oxycarbonyl having a substituent selected from the group consisting of hydrogen and $(C_{1-10})$alkyl; aminocarbonyl itself optionally having a $(C_{1-10})$alkyl; amino itself optionally having a $(C_{1-10})$alkyl; $(C_{1-10})$alkylamino itself optionally having a $(C_{1-10})$alkyl; sulfonyl having a substituent selected from the group consisting of $(C_{1-10})$alkyl and $(C_{3-12})$cycloalkyl; sulfinyl having a substituent selected from the group consisting of $(C_{1-10})$alkyl and $(C_{3-12})$cycloalkyl; $(C_{1-10})$alkyl itself optionally having a substituent selected from the group consisting of halo, nitro, cyano, hydroxy, $(C_{1-10})$alkoxy, amino, $(C_{3-12})$cycloalkyl, and $(C_{4-12})$aryl; halo$(C_{1-10})$alkyl itself optionally having a substituent selected from the group consisting of nitro, cyano, hydroxy, $(C_{1-10})$alkoxy, amino, $(C_{3-12})$cycloalkyl, and $(C_{4-12})$aryl; hydroxy$(C_{1-10})$alkyl itself optionally having a substituent selected from the group consisting of halo, nitro, cyano, $(C_{1-10})$alkoxy, amino, $(C_{3-12})$cycloalkyl, and $(C_{4-12})$aryl; $(C_{3-12})$cycloalkyl; and $(C_{4-12})$aryl itself optionally having a substituent selected from the group consisting of halo, nitro, cyano, hydroxy, $(C_{1-10})$alkoxy, amino, and $(C_{3-12})$cycloalkyl;

$R_3$ is selected from the group consisting of hydrogen; hydroxy; $(C_{1-10})$alkoxy unsubstituted or substituted with one or more substituents through available valencies selected from the group consisting of halo; nitro; cyano; thio having a substituent selected from the group consisting of hydrogen and $(C_{1-10})$alkyl; hydroxy; $(C_{1-10})$alkoxy itself optionally having a substituent selected from the group consisting of halo, nitro, cyano, hydroxy, $(C_{1-10})$alkoxy, amino, $(C_{3-12})$cycloalkyl, and $(C_{4-12})$aryl; $(C_{4-12})$aryloxy; oxycarbonyl having a substituent selected from the group consisting of hydrogen and $(C_{1-10})$alkyl; aminocarbonyl itself optionally having a $(C_{1-10})$alkyl; amino itself optionally having a $(C_{1-10})$alkyl; $(C_{1-10})$alkylamino itself optionally having a $(C_{1-10})$alkyl; $(C_{3-12})$cycloalkyl; and $(C_{4-12})$aryl itself optionally having a substituent selected from the group consisting of halo, nitro, cyano, hydroxy, $(C_{1-10})$alkoxy, amino, and $(C_{3-12})$cycloalkyl; hydroxy$(C_{1-10})$alkoxy unsubstituted or substituted with one or more substituents through available valencies selected from the group consisting of halo; nitro; cyano; thio having a substituent selected from the group consisting of hydrogen and $(C_{1-10})$alkyl; $(C_{1-10})$alkoxy itself optionally having a substituent selected from the group consisting of halo, nitro, cyano, hydroxy, $(C_{1-10})$alkoxy, amino, $(C_{3-12})$cycloalkyl, and $(C_{4-12})$aryl; $(C_{4-12})$aryloxy; oxycarbonyl having a substituent selected from the group consisting of hydrogen and $(C_{1-10})$alkyl; aminocarbonyl itself optionally having a $(C_{1-10})$alkyl; amino itself optionally having a $(C_{1-10})$alkyl; $(C_{1-10})$alkylamino itself optionally having a $(C_{1-10})$alkyl; $(C_{3-12})$cycloalkyl; and $(C_{4-12})$aryl itself optionally having a substituent selected from the group consisting of halo, nitro, cyano, hydroxy, $(C_{1-10})$alkoxy, amino, and $(C_{3-12})$cycloalkyl; $(C_{1-10})$alkyl unsubstituted or substituted with one or more substituents through available valencies selected from the group consisting of halo; nitro; cyano; thio having a substituent selected from the group consisting of hydrogen and $(C_{1-10})$alkyl; hydroxy; $(C_{1-10})$alkoxy itself optionally having a substituent selected from the group consisting of halo, nitro, cyano, hydroxy, $(C_{1-10})$alkoxy, amino, $(C_{3-12})$cycloalkyl, and $(C_{4-12})$aryl; $(C_{4-12})$aryloxy; oxycarbonyl itself having a substituent selected from the group consisting of hydrogen and $(C_{1-10})$alkyl; aminocarbonyl itself optionally having a $(C_{1-10})$alkyl; amino itself optionally having a $(C_{1-10})$alkyl; $(C_{1-10})$alkylamino itself optionally having a $(C_{1-10})$alkyl; $(C_{3-12})$cycloalkyl; and $(C_{4-12})$aryl itself optionally having a substituent selected from the group consisting of halo, nitro, cyano, hydroxy, $(C_{1-10})$alkoxy, amino, and $(C_{3-12})$cycloalkyl; halo$(C_{1-10})$alkyl unsubstituted or substituted with one or more substituents through available valencies selected from the group consisting of nitro; cyano; thio having a substituent selected from the group consisting of hydrogen and $(C_{1-10})$alkyl; hydroxy; $(C_{1-10})$alkoxy itself optionally having a substituent selected from the group consisting of halo, nitro, cyano, hydroxy, $(C_{1-10})$alkoxy, amino, $(C_{3-12})$cycloalkyl, and $(C_{4-12})$aryl; $(C_{4-12})$aryloxy; oxycarbonyl having a substituent selected from the group consisting of hydrogen and $(C_{1-10})$alkyl; aminocarbonyl itself optionally having a $(C_{1-10})$alkyl; amino itself optionally having a $(C_{1-10})$alkyl; $(C_{1-10})$alkylamino itself optionally having a $(C_{1-10})$alkyl; $(C_{3-12})$cycloalkyl; and $(C_{4-12})$aryl itself optionally having a substituent selected from the group consisting of halo, nitro, cyano, hydroxy, $(C_{1-10})$alkoxy, amino, and $(C_{3-12})$cycloalkyl; hydroxy$(C_{1-10})$alkyl unsubstituted or substituted with one or more substituents through available valencies selected from the group consisting of halo; nitro; cyano; thio having a substituent selected from the group consisting of hydrogen and $(C_{1-10})$alkyl; $(C_{1-10})$alkoxy itself optionally having a substituent selected from the group consisting of halo, nitro, cyano, hydroxy, $(C_{1-10})$alkoxy, amino, $(C_{3-12})$cycloalkyl, and $(C_{4-12})$aryl; $(C_{4-12})$aryloxy; oxycarbonyl having a substituent selected from the group consisting of hydrogen and $(C_{1-10})$alkyl; aminocarbonyl itself optionally having a $(C_{1-10})$alkyl; amino itself optionally having a $(C_{1-10})$alkyl; $(C_{1-10})$alkylamino itself optionally having a $(C_{1-10})$alkyl; $(C_{3-12})$cycloalkyl; and $(C_{4-12})$aryl itself optionally having a substituent selected from the group consisting of halo, nitro, cyano, hydroxy, $(C_{1-10})$alkoxy, amino, and $(C_{3-12})$cycloalkyl; amino$(C_{1-10})$alkyl unsubstituted or substituted with one or more substituents through available valencies selected from the group consisting of halo; nitro; cyano; thio having a substituent selected from the group consisting of hydrogen and $(C_{1-10})$alkyl; hydroxy; $(C_{1-10})$alkoxy itself optionally having a substituent selected from the group consisting of halo, nitro, cyano, hydroxy, $(C_{1-10})$alkoxy, amino, $(C_{3-12})$cycloalkyl, and $(C_{4-12})$aryl; $(C_{4-12})$aryloxy; oxycarbonyl having a substituent selected from the group consisting of hydrogen and $(C_{1-10})$alkyl; aminocarbonyl itself optionally having a $(C_{1-10})$alkyl; $(C_{3-12})$cycloalkyl; and $(C_{4-12})$aryl itself optionally having a substituent selected from the group consisting of halo, nitro, cyano, hydroxy, $(C_{1-10})$alkoxy, amino, and $(C_{3-12})$cycloalkyl; $(C_{3-12})$cycloalkyl $(C_{1-5})$alkyl unsubstituted or substituted with one or more substituents through available valencies selected from the group consisting of halo; nitro; cyano; thio having a substituent selected from the group consisting of hydrogen and $(C_{1-10})$alkyl; hydroxy; $(C_{1-10})$alkoxy itself optionally having a substituent selected from the group consisting of halo, nitro, cyano, hydroxy, $(C_{1-10})$alkoxy, amino, $(C_{3-12})$cycloalkyl, and $(C_{4-12})$aryl; $(C_{4-12})$aryloxy; oxycarbonyl having a substituent selected from the group consisting of hydrogen and $(C_{1-10})$alkyl; aminocarbonyl itself optionally having a $(C_{1-10})$alkyl; amino itself optionally having a $(C_{1-10})$alkyl; $(C_{1-10})$alkylamino itself optionally having a $(C_{1-10})$alkyl; and $(C_{4-12})$aryl itself optionally having a substituent selected from the group consisting of halo, nitro, cyano, hydroxy, $(C_{1-10})$alkoxy, amino, and $(C_{3-12})$cycloalkyl; hetero$(C_{3-12})$cycloalkyl $(C_{1-5})$alkyl wherein the hetero$(C_{3-12})$cycloalkyl is selected from the group consisting of piperidyl, 4-morpholinyl, 4-piperazinyl, pyrrolidinyl, 1,3-dioxanyl, and 1,4-dioxanyl and is unsubstituted or substituted with one or more substituents through available valencies selected from the group consisting of halo; nitro; cyano; thio having a substituent selected from the group consisting of hydrogen and $(C_{1-10})$alkyl; hydroxy; $(C_{1-10})$alkoxy itself optionally having a substituent selected from the group consisting of halo, nitro, cyano, hydroxy, $(C_{1-10})$alkoxy, amino, $(C_{3-12})$cycloalkyl, and $(C_{4-12})$aryl; $(C_{4-12})$aryloxy; oxycarbonyl having a substituent selected from the group consisting of hydrogen and $(C_{1-10})$alkyl; aminocarbonyl itself optionally having a $(C_{1-10})$alkyl; amino itself optionally having a $(C_{1-10})$alkyl; $(C_{1-10})$alkylamino itself optionally having a $(C_{1-10})$alkyl; $(C_{3-12})$cycloalkyl; and $(C_{4-12})$aryl itself optionally having a substituent selected from the group consisting of halo, nitro, cyano, hydroxy, $(C_{1-10})$alkoxy, amino, and $(C_{3-12})$cycloalkyl; aryl$(C_{1-10})$alkyl unsubstituted or substituted with one or more substituents through available valencies selected from the group consisting of halo; nitro; cyano; thio having a substituent selected from the group consisting of hydrogen and $(C_{1-10})$alkyl; hydroxy; $(C_{1-10})$alkoxy itself optionally having a substituent selected from the group consisting of halo, nitro, cyano, hydroxy, $(C_{1-10})$alkoxy, amino, $(C_{3-12})$cycloalkyl, and $(C_{4-12})$aryl; $(C_{4-12})$aryloxy; oxycarbonyl having a substituent selected from the group consisting of hydrogen and $(C_{1-10})$alkyl; aminocarbonyl itself optionally having a $(C_{1-10})$alkyl; amino itself optionally having a $(C_{1-10})$alkyl; $(C_{1-10})$alkylamino itself optionally having a $(C_{1-10})$alkyl; $(C_{3-12})$cycloalkyl; and $(C_{4-12})$aryl itself optionally having a substituent selected from the group consisting of halo, nitro, cyano, hydroxy, ($C_{1-10}$)alkoxy, amino, and ($C_{3-12}$)cycloalkyl; heteroaryl ($C_{1-5}$)alkyl wherein the heteroaryl is selected from the group consisting of furyl, imidazolyl, isothiazolyl, isoxazolyl, oxadiazolyl, oxazolyl, 1,2,3-oxadiazolyl, pyrazinyl, pyrazolyl, pyridazinyl, pyridinyl, pyrimidinyl, pyrrolinyl, thiazolyl, 1,3,4-thiadiazolyl, triazolyl and tetrazolyl and is unsubstituted or substituted with one or more substituents through available valencies selected from the group consisting of halo; nitro; cyano; thio having a substituent selected from the group consisting of hydrogen and ($C_{1-10}$)alkyl; hydroxy; ($C_{1-10}$)alkoxy itself optionally having a substituent selected from the group consisting of halo, nitro, cyano, hydroxy, ($C_{1-10}$)alkoxy, amino, ($C_{3-12}$)cycloalkyl, and ($C_{4-12}$)aryl; ($C_{4-12}$)aryloxy; oxycarbonyl having a substituent selected from the group consisting of hydrogen and ($C_{1-10}$)alkyl; aminocarbonyl itself optionally having a ($C_{1-10}$)alkyl; amino itself optionally having a ($C_{1-10}$)alkyl; ($C_{1-10}$)alkylamino itself optionally having a ($C_{1-10}$)alkyl; ($C_{3-12}$)cycloalkyl; and ($C_{4-12}$)aryl itself optionally having a substituent selected from the group consisting of halo, nitro, cyano, hydroxy, ($C_{1-10}$)alkoxy, amino, and ($C_{3-12}$)cycloalkyl; ($C_{3-12}$)cycloalkyl unsubstituted or substituted with one or more substituents through available valencies selected from the group consisting of halo; nitro; cyano; ($C_{1-10}$)alkoxy itself optionally having a substituent selected from the group consisting of halo, nitro, cyano, hydroxy, ($C_{1-10}$)alkoxy, amino, ($C_{3-12}$)cycloalkyl, and ($C_{4-12}$)aryl; and ($C_{1-10}$)alkyl; ($C_{4-12}$)aryl unsubstituted or substituted with one or more substituents through available valencies selected from the group consisting of halo; nitro; cyano; thio having a substituent selected from the group consisting of hydrogen and ($C_{1-10}$)alkyl; ($C_{1-10}$)alkoxy itself optionally having a substituent selected from the group consisting of halo, nitro, cyano, hydroxy, ($C_{1-10}$)alkoxy, amino, ($C_{3-12}$) cycloalkyl, and ($C_{4-12}$)aryl; ($C_{4-12}$)aryloxy; oxycarbonyl having a substituent selected from the group consisting of hydrogen and ($C_{1-10}$)alkyl; aminocarbonyl itself optionally having a ($C_{1-10}$)alkyl; amino itself optionally having a ($C_{1-10}$)alkyl; ($C_{1-10}$)alkylamino itself optionally having a ($C_{1-10}$)alkyl; sulfonyl having a substituent selected from the group consisting of ($C_{1-10}$)alkyl and ($C_{3-12}$)cycloalkyl; sulfinyl having a substituent selected from the group consisting of ($C_{1-10}$)alkyl and ($C_{3-12}$)cycloalkyl; ($C_{1-10}$)alkyl itself optionally having a substituent selected from the group consisting of halo, nitro, cyano, hydroxy, ($C_{1-10}$)alkoxy, amino, ($C_{3-12}$)cycloalkyl, and ($C_{4-12}$)aryl; halo($C_{1-10}$)alkyl itself optionally having a substituent selected from the group consisting of nitro, cyano, hydroxy, ($C_{1-10}$)alkoxy, amino, ($C_{3-12}$)cycloalkyl, and ($C_{4-12}$)aryl; hydroxy($C_{1-10}$)alkyl itself optionally having a substituent selected from the group consisting of halo, nitro, cyano, ($C_{1-10}$)alkoxy, amino, ($C_{3-12}$)cycloalkyl, and ($C_{4-12}$)aryl; and ($C_{4-12}$)aryl itself optionally having a substituent selected from the group consisting of halo, nitro, cyano, hydroxy, ($C_{1-10}$)alkoxy, amino, and ($C_{3-12}$)cycloalkyl; hetero($C_{1-10}$)aryl wherein the heteroaryl is selected from the group consisting of furyl, imidazolyl, isothiazolyl, isoxazolyl, oxadiazolyl, oxazolyl, 1,2,3-oxadiazolyl, pyrazinyl, pyrazolyl, pyridazinyl, pyridinyl, pyrimidinyl, pyrrolinyl, thiazolyl, 1,3,4-thiadiazolyl, triazolyl and tetrazolyl and is unsubstituted or substituted with one or more substituents through available valencies selected from the group consisting of halo; nitro; cyano; thio having a substituent selected from the group consisting of hydrogen and ($C_{1-10}$)alkyl; hydroxy; ($C_{1-10}$)alkoxy itself optionally having a substituent selected from the group consisting of halo, nitro, cyano, hydroxy, ($C_{1-10}$) alkoxy, amino, ($C_{3-12}$)cycloalkyl, and ($C_{4-12}$)aryl; ($C_{4-12}$) aryloxy; oxycarbonyl having a substituent selected from the group consisting of hydrogen and ($C_{1-10}$)alkyl; aminocarbonyl itself optionally having a ($C_{1-10}$)alkyl; amino itself optionally having a ($C_{1-10}$)alkyl; ($C_{1-10}$)alkylamino itself optionally having a ($C_{1-10}$)alkyl; ($C_{3-12}$)cycloalkyl; and ($C_{4-12}$)aryl itself optionally having a substituent selected from the group consisting of halo, nitro, cyano, hydroxy, ($C_{1-10}$)alkoxy, amino, and ($C_{3-12}$)cycloalkyl;

$R_5$ is ($C_{1-6}$)alkyl unsubstituted or substituted with one or more substituents through available valencies selected from the group consisting of halo; nitro; cyano; thio having a substituent selected from the group consisting of hydrogen and ($C_{1-10}$)alkyl; hydroxy; ($C_{1-10}$)alkoxy itself optionally having a substituent selected from the group consisting of halo, nitro, cyano, hydroxy, ($C_{1-10}$)alkoxy, amino, ($C_{3-12}$)cycloalkyl, and ($C_{4-12}$)aryl; ($C_{4-12}$)aryloxy; oxycarbonyl having a substituent selected from the group consisting of hydrogen and ($C_{1-10}$)alkyl; aminocarbonyl itself optionally having a ($C_{1-10}$)alkyl; amino itself optionally having a ($C_{1-10}$)alkyl; ($C_{1-10}$)alkylamino itself optionally having a ($C_{1-10}$)alkyl; and ($C_{4-12}$)aryl itself optionally having a substituent selected from the group consisting of halo, nitro, cyano, hydroxy, ($C_{1-10}$)alkoxy, amino, and ($C_{3-12}$)cycloalkyl;

$R_6$ are each independently selected from the group consisting of hydrogen; halo; amino unsubstituted or substituted with one or more ($C_{1-10}$)alkyl; and ($C_{1-5}$)alkyl unsubstituted or substituted with one or more substituents through available valencies selected from the group consisting of halo; nitro; cyano; thio having a substituent selected from the group consisting of hydrogen and ($C_{1-10}$)alkyl; hydroxy; ($C_{1-10}$)alkoxy itself optionally having a substituent selected from the group consisting of halo, nitro, cyano, hydroxy, ($C_{1-10}$)alkoxy, amino, ($C_{3-12}$)cycloalkyl, and ($C_{4-12}$)aryl; ($C_{4-12}$)aryloxy; oxycarbonyl having a substituent selected from the group consisting of hydrogen and ($C_{1-10}$)alkyl; aminocarbonyl itself optionally having a ($C_{1-10}$)alkyl; amino itself optionally having a ($C_{1-10}$)alkyl; ($C_{1-10}$)alkylamino itself optionally having a ($C_{1-10}$)alkyl; and ($C_{4-12}$)aryl itself optionally having a substituent selected from the group consisting of halo, nitro, cyano, hydroxy, ($C_{1-10}$)alkoxy, amino, and ($C_{3-12}$) cycloalkyl.

In some embodiments, for the compound of forumula (IA), the $R_6$ on $X_1$ is halo.

In some other embodiments, for the compound of forumula (IA), the $R_6$ on $X_1$ is hydrogen.

In yet other embodiments, for the compound of forumula (IA), the $R_6$ on $X_5$ is halo.

In yet other embodiments, for the compound of forumula (IA), the $R_6$ on $X_5$ is ($C_{1-5}$)alkyl unsubstituted or substituted with one or more substituents through available valencies selected from the group consisting of halo; nitro; cyano; thio having a substituent selected from the group consisting of hydrogen and ($C_{1-10}$)alkyl; hydroxy; ($C_{1-10}$)alkoxy itself optionally having a substituent selected from the group consisting of halo, nitro, cyano, hydroxy, ($C_{1-10}$)alkoxy, amino, ($C_{3-12}$)cycloalkyl, and ($C_{4-12}$)aryl; ($C_{4-12}$)aryloxy; oxycarbonyl having a substituent selected from the group consisting of hydrogen and ($C_{1-10}$)alkyl; aminocarbonyl itself optionally having a ($C_{1-10}$)alkyl; amino itself optionally having a ($C_{1-10}$)alkyl; ($C_{1-10}$)alkylamino itself optionally having a ($C_{1-10}$)alkyl; and ($C_{4-12}$)aryl itself optionally having a substituent selected from the group consisting of halo, nitro, cyano, hydroxy, $(C_{1-10})$alkoxy, amino, and $(C_{3-12})$cycloalkyl.

In yet other embodiments, for the compound of forumula (IA), the $R_6$ on $X_5$ is hydrogen.

In yet other embodiments, for the compound of forumula (IA), $R_1$ comprises:

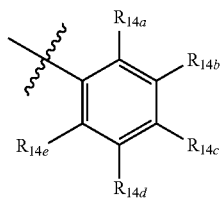

wherein $R_{14a}$, $R_{14b}$, $R_{14c}$, $R_{14d}$ and $R_{14e}$ are each independently selected from the group consisting of hydrogen, halo, cyano, $(C_{1-10})$alkoxy itself optionally having a substituent selected from the group consisting of halo, nitro, cyano, hydroxy, $(C_{1-10})$alkoxy, amino $(C_{3-12})$cycloalkyl, and $(C_{4-12})$aryl; $(C_{1-3})$alkyl itself optionally having a substituent selected from the group consisting of halo, nitro, cyano, hydroxy, $(C_{1-10})$alkoxy, amino $(C_{3-12})$cycloalkyl, and $(C_{4-12})$aryl; and hydroxy$(C_{1-3})$alkyl itself optionally having a substituent selected from the group consisting of halo, nitro, cyano, $(C_{1-10})$alkoxy, amino $(C_{3-12})$cycloalkyl, and $(C_{4-12})$aryl.

In some embodiments, the MEK inhibitor is a compound represented by formula (II):

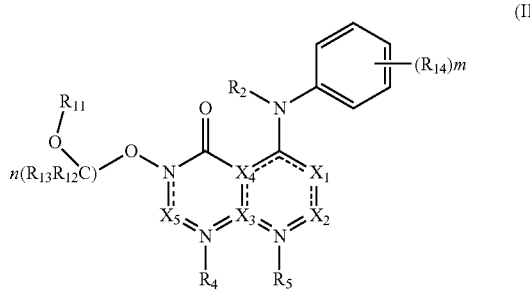

or a pharmaceutically acceptable salt thereof;

wherein:

m is selected from the group consisting of 0, 1, 2, 3, 4 and 5;

n is selected from the group consisting of 1, 2, 3, 4, 5 and 6;

$R_{11}$ is selected from the group consisting of hydrogen, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

each $R_{12}$ and $R_{13}$ is independently selected from the group consisting of hydrogen, halo, nitro, cyano, thio, oxy, hydroxy, carbonyloxy, alkoxy, aryloxy, heteroaryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, heteroaryl$(C_{1-5})$alkyl, $(C_{9-2})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted; and each $R_{14}$ is independently selected from the group consisting of hydrogen, halo, nitro, cyano, thio, oxy, hydroxy, carbonyloxy, alkoxy, aryloxy, heteroaryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-15})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or two $R_{14}$ are taken together to form a substituted or unsubstituted ring.

Table 1 provides the chemical names for specific examples of compounds of formula (I).

TABLE 1

| | Examples of Compounds of Formula (I) |
|---|---|
| I-1: | 5-(2-fluoro-4-iodophenylamino)-3,8-dimethylpyrido[2,3-d]pyrimidine-4,7(3H,8H)-dione |
| I-2: | 5-(2-fluoro-4-iodophenylamino)-3-(2-hydroxyethyl)-8-methylpyrido[2,3-d]pyrimidine-4,7(3H,8H)-dione |
| I-3 | methyl 2-(5-(2-fluoro-4-iodophenylamino)-8-methyl-4,7-dioxo-7,8-dihydropyrido[2,3-d]pyrimidin-3(4H)-yl)acetate |
| I-4 | 5-(2-fluoro-4-iodophenylamino)-3,6,8-trimethylpyrido[2,3-d]pyrimidine-4,7(3H,8H)-dione |
| I-5 | (S)-3-(2,3-Dihydroxypropyl)-5-(2-fluoro-4-iodophenylamino)-8-methylpyrido[2,3-d]pyrimidine-4,7(3H,8H)-dione |
| I-6 | (R)-3-(2,3-Dihydroxypropyl)-5-(2-fluoro-4-iodophenylamino)-8-methylpyrido[2,3-d]pyrimidine-4,7(3H,8H)-dione |
| I-7 | (S)-6-Chloro-3-(2,3-dihydroxypropyl)-5-(2-fluoro-4-iodophenylamino)-8-methylpyrido[2,3-d]pyrimidine-4,7(3H,8H)-dione |
| I-8 | (R)-3-(2,3-Dihydroxypropyl)-5-(2-fluoro-4-iodophenylamino)-6,8-dimethylpyrido[2,3-d]pyrimidine-4,7(3H,8H)-dione |

TABLE 1-continued

Examples of Compounds of Formula (I)

| | |
|---|---|
| I-9 | (S)-5-(4-Bromo-2-fluorophenylamino)-3-(2,3-dihydroxypropyl)-6,8-dimethylpyrido[2,3-d]pyrimidine-4,7(3H,8H)-dione |
| I-10 | (R)-5-(4-Bromo-2-fluorophenylamino)-3-(2,3-dihydroxypropyl)-6,8-dimethylpyrido[2,3-d]pyrimidine-4,7(3H,8H)-dione |
| I-11 | 5-(4-Bromo-2-fluorophenylamino)-3-(2-hydroxyethyl)-6,8-dimethylpyrido[2,3-d]pyrimidine-4,7(3H,8H)-dione |
| I-12 | 5-(2-Fluoro-4-iodophenylamino)-6,8-dimethylpyrido[2,3-d]pyrimidine-4,7(3H,8H)-dione |
| I-13 | (S)-3-(2,3-Dihydroxypropyl)-5-(2-fluoro-4-iodophenylamino)-6,8-dimethylpyrido[2,3-d]pyrimidine-4,7(3H,8H)-dione |
| I-14 | 5-(2-Fluoro-4-iodophenylamino)-3-(2-hydroxyethyl)-6,8-dimethylpyrido[2,3-d]pyrimidine-4,7(3H,8H)-dione |
| I-15 | 5-(2-Fluorophenylamino)-3-(2-hydroxyethyl)-6,8-dimethylpyrido[2,3-d]pyrimidine-4,7(3H,8H)-dione |
| I-16 | (R)-3-(2,3-Dihydroxypropyl)-5-(4-ethynyl-2-fluorophenylamino)-6,8-dimethylpyrido[2,3-d]pyrimidine-4,7(3H,8H)-dione |
| I-17 | 6-Fluoro-5-(2-fluoro-4-iodophenylamino)-3-(2-hydroxyethyl)-8-methylpyrido[2,3-d]pyrimidine-4,7(3H,8H)-dione |
| I-18 | (R)-3-(2,3-Dihydroxypropyl)-6-fluoro-5-(2-fluoro-4-iodophenylamino)-8-methylpyrido[2,3-d]pyrimidine-4,7(3H,8H)-dione |
| I-19 | (S)-3-(2,3-Dihydroxypropyl)-6-fluoro-5-(2-fluoro-4-iodophenylamino)-8-methylpyrido[2,3-d]pyrimidine-4,7(3H,8H)-dione |
| I-20 | (R)-5-(4-Bromo-2-fluorophenylamino)-3-(2,3-dihydroxypropyl)-6-fluoro-8-methylpyrido[2,3-d]pyrimidine-4,7(3H,8H)-dione |
| I-21 | (S)-3-(2,3-Dihydroxypropyl)-5-(4-ethynyl-2-fluorophenylamino)-6-fluoro-8-methylpyrido[2,3-d]pyrimidine-4,7(3H,8H)-dione |
| I-22 | (R)-3-(2,3-dihydroxypropyl)-5-(4-ethynyl-2-fluorophenylamino)-6-fluoro-8-methylpyrido[2,3-d]pyrimidine-4,7(3H,8H)-dione |
| I-23 | (R)-N-(4-(3-(2,3-Dihydroxypropyl)-6-fluoro-8-methyl-4,7-dioxo-3,4,7,8-tetrahydropyrido[2,3-d]pyrimidin-5-ylamino)-3-fluorophenyl)methanesulfonamide |
| I-24 | 3-(1,3-Dihydroxypropan-2-yl)-5-(2-fluoro-4-iodophenylamino)-8-methylpyrido[2,3-d]pyrimidine-4,7(3H,8H)-dione |
| I-25 | 3-(1,3-Dihydroxypropan-2-yl)-6-fluoro-5-(2-fluoro-4-iodophenylamino)-8-methylpyrido[2,3-d]pyrimidine-4,7(3H,8H)-dione |
| I-26 | 5-(2-Fluoro-4-iodophenylamino)-3-(2-hydroxyethoxy)-8-methylpyrido[2,3-d]pyrimidine-4,7(3H,8H)-dione |
| I-27 | (R)-3-(2,3-Dihydroxypropoxy)-5-(2-fluoro-4-iodophenylamino)-8-methylpyrido[2,3-d]pyrimidine-4,7(3H,8H)-dione |
| I-28 | (R)-3-(2,3-Dihydroxypropoxy)-6-fluoro-5-(2-fluoro-4-iodophenylamino)-8-methylpyrido[2,3-d]pyrimidine-4,7(3H,8H)-dione |
| I-29 | (R)-5-(4-Bromo-2-fluorophenylamino)-6-chloro-3-(2,3-dihydroxypropyl)-8-methylpyrido[2,3-d]pyrimidine-4,7(3H,8H)-dione |
| I-30 | 6-Chloro-5-(2-fluoro-4-iodophenylamino)-3-(2-hydroxyethyl)-8-methylpyrido[2,3-d]pyrimidine-4,7(3H,8H)-dione |
| I-31 | 5-(2-Fluoro-4-iodophenylamino)-3-(3-hydroxypropyl)-8-methylpyrido[2,3-d]pyrimidine-4,7(3H,8H)-dione |
| I-32 | 6-Chloro-5-(2-fluoro-4-iodophenylamino)-3-(3-hydroxypropyl)-8-methylpyrido[2,3-d]pyrimidine-4,7(3H,8H)-dione |
| I-33 | 5-(4-Bromo-2-fluorophenylamino)-3-(3-hydroxypropyl)-8-methylpyrido[2,3-d]pyrimidine-4,7(3H,8H)-dione |
| I-34 | 5-(4-Bromo-2-fluorophenylamino)-6-chloro-3-(3-hydroxypropyl)-8-methylpyrido[2,3-d]pyrimidine-4,7(3H,8H)-dione |
| I-35 | 5-(4-Bromo-2-chlorophenylamino)-3-(3-hydroxypropyl)-8-methylpyrido[2,3-d]pyrimidine-4,7(3H,8H)-dione |
| I-36 | 5-(4-Bromo-2-chlorophenylamino)-6-chloro-3-(3-hydroxypropyl)-8-methylpyrido[2,3-d]pyrimidine-4,7(3H,8H)-dione |
| I-37 | 3-(2-(Dimethylamino)ethyl)-5-(2-fluoro-4-iodophenylamino)-8-methylpyrido[2,3-d]pyrimidine-4,7(3H,8H)-dione |
| I-38 | 5-(2-Fluoro-4-iodophenylamino)-3-(2-hydroxypropyl)-8-methylpyrido[2,3-d]pyrimidine-4,7(3H,8H)-dione |
| I-39 | (S)-3-(2,4-Dihydroxybutyl)-5-(2-fluoro-4-iodophenylamino)-8-methylpyrido[2,3-d]pyrimidine-4,7(3H,8H)-dione |
| I-40 | 6-Chloro-5-(2-fluoro-4-iodophenylamino)-3-(2-hydroxypropyl)-8-methylpyrido[2,3-d]pyrimidine-4,7(3H,8H)-dione |
| I-41 | (S)-5-(4-Bromo-2-fluorophenylamino)-3-(2,3-dihydroxypropyl)-6-fluoro-8-methylpyrido[2,3-d]pyrimidine-4,7(3H,8H)-dione |
| I-42 | 3-Benzyl-5-(2-fluoro-4-iodophenylamino)-8-methylpyrido[2,3-d]pyrimidine-4,7(3H,8H)-dione |
| I-43 | 3-(1,3-Dihydroxypropan-2-yl)-5-(2-fluoro-4-iodophenylamino)-6,8-dimethylpyrido[2,3-d]pyrimidine-4,7(3H,8H)-dione |
| I-44 | (S)-3-(2,3-Dihydroxypropyl)-5-(4-ethynyl-2-fluorophenylamino)-6,8-dimethylpyrido[2,3-d]pyrimidine-4,7(3H,8H)-dione |
| I-45 | 2-fluoro-5-(2-fluoro-4-iodophenylamino)-3,8-dimethylpyrido[2,3-d]pyrimidine-4,7(3H,8H)-dione |
| I-46 | 5-(2-fluoro-4-iodophenylamino)-3,8-dimethyl-2-(methylamino)pyrido[2,3-d]pyrimidine-4,7(3H,8H)-dione |

TABLE 1-continued

Examples of Compounds of Formula (I)

| | |
|---|---|
| I-47 | 5-(2-fluoro-4-iodophenylamino)-2,3,8-trimethylpyrido[2,3-d]pyrimidine-4,7(3H,8H)-dione |
| I-48 | 5-(2-fluoro-4-iodophenylamino)-1,8-dimethylpyrido[2,3-d]pyrimidine-4,7(1H,8H)-dione |
| I-49 | 3-(5-(2-fluoro-4-iodophenylamino)-8-methyl-4,7-dioxo-7,8-dihydropyrido[2,3-d]pyrimidin-1(4H)-yl)propanamide |
| I-50 | N-(2-(5-(2-fluoro-4-iodophenylamino)-8-methyl-4,7-dioxo-7,8-dihydropyrido[2,3-d]pyrimidin-1(4H)-yl)ethyl)acetamide |
| I-51 | 5-(2-fluoro-4-iodophenylamino)-1-(2-hydroxyethyl)-8-methylpyrido[2,3-d]pyrimidine-4,7(1H,8H)-dione |
| I-52 | 2-(5-(2-fluoro-4-iodophenylamino)-8-methyl-4,7-dioxo-7,8-dihydropyrido[2,3-d]pyrimidin-1(4H)-yl)-N-methylacetamide |
| I-53 | 1-ethyl-5-(2-fluoro-4-iodophenylamino)-8-methylpyrido[2,3-d]pyrimidine-4,7(1H,8H)-dione |
| I-54 | 3-cyclopropyl-5-(2-fluoro-4-iodophenylamino)-8-methylpyrido[2,3-d]pyrimidine-4,7(3H,8H)-dione |
| I-55 | (S)-5-(4-bromo-2-chlorophenylamino)-3-(2,3-dihydroxypropyl)-8-methylpyrido[2,3-d]pyrimidine-4,7(3H,8H)-dione |
| I-56 | (S)-3-(2,3-dihydroxypropoxy)-5-(2-fluoro-4-iodophenylamino)-8-methylpyrido[2,3-d]pyrimidine-4,7(3H,8H)-dione |
| I-57 | 3-(2-aminoethoxy)-5-(2-fluoro-4-iodophenylamino)-8-methylpyrido[2,3-d]pyrimidine-4,7(3H,8H)-dione |
| I-58 | 3-(3-aminopropyl)-5-(2-fluoro-4-iodophenylamino)-8-methylpyrido[2,3-d]pyrimidine-4,7(3H,8H)-dione |
| I-59 | 3-(2-aminoethyl)-5-(2-fluoro-4-iodophenylamino)-8-methylpyrido[2,3-d]pyrimidine-4,7(3H,8H)-dione |
| I-60 | 5-(2-fluoro-4-iodophenylamino)-8-methyl-3-(pyrrolidin-3-ylmethyl)pyrido[2,3-d]pyrimidine-4,7(3H,8H)-dione |
| I-61 | (S)-5-(2-chloro-4-iodophenylamino)-3-(2,3-dihydroxypropyl)-8-methylpyrido[2,3-d]pyrimidine-4,7(3H,8H)-dione |
| I-62 | (S)-5-(4-bromo-2-fluorophenylamino)-3-(2,3-dihydroxypropyl)-8-methylpyrido[2,3-d]pyrimidine-4,7(3H,8H)-dione |
| I-63 | (S)-3-(2,3-dihydroxypropyl)-5-(2-fluoro-4-iodophenylamino)-6,8-dimethylpyrido[4,3-d]pyrimidine-4,7(3H,6H)-dione |
| I-64 | (R)-3-(2,3-dihydroxypropyl)-5-(2-fluoro-4-iodophenylamino)-6,8-dimethylpyrido[4,3-d]pyrimidine-4,7(3H,6H)-dione |
| I-65 | 5-(2-fluoro-4-iodophenylamino)-3-(2-hydroxyethoxy)-6,8-dimethylpyrido[4,3-d]pyrimidine-4,7(3H,6H)-dione |
| I-66 | 5-(2-fluoro-4-iodophenylamino)-3-(3-hydroxypropyl)-6,8-dimethylpyrido[4,3-d]pyrimidine-4,7(3H,6H)-dione |
| I-67 | 5-(2-fluoro-4-iodophenylamino)-3-(2-hydroxyethyl)-6,8-dimethylpyrido[4,3-d]pyrimidine-4,7(3H,6H)-dione |
| I-68 | (R)-3-(2,3-Dihydroxypropyl)-5-(2-fluoro-4-iodophenylamino)-6,8-dimethylpyrido[2,3-d]pyrimidine-4,7(3H,8H)-dione |
| I-69 | (S)-3-(2,3-Dihydroxypropyl)-5-(2-fluoro-4-iodophenylamino)-6,8-dimethylpyrido[2,3-d]pyrimidine-4,7(3H,8H)-dione |
| I-70 | (R)-3-(2,3-Dihydroxypropyl)-6-fluoro-5-(2-fluoro-4-iodophenylamino)-8-methylpyrido[2,3-d]pyrimidine-4,7(3H,8H)-dione |
| I-71 | (S)-3-(2,3-Dihydroxypropyl)-6-fluoro-5-(2-fluoro-4-iodophenylamino)-8-methylpyrido[2,3-d]pyrimidine-4,7(3H,8H)-dione |
| I-72 | (S)-3-(2,3-Dihydroxypropyl)-5-(4-ethynyl-2-fluorophenylamino)-6-fluoro-8-methylpyrido[2,3-d]pyrimidine-4,7(3H,8H)-dione |
| I-73 | (R)-3-(2,3-dihydroxypropyl)-5-(4-ethynyl-2-fluorophenylamino)-6-fluoro-8-methylpyrido[2,3-d]pyrimidine-4,7(3H,8H)-dione |
| I-74 | 3-(1,3-Dihydroxypropan-2-yl)-6-fluoro-5-(2-fluoro-4-iodophenylamino)-8-methylpyrido[2,3-d]pyrimidine-4,7(3H,8H)-dione |
| I-75 | (R)-3-(2,3-Dihydroxypropoxy)-6-fluoro-5-(2-fluoro-4-iodophenylamino)-8-methylpyrido[2,3-d]pyrimidine-4,7(3H,8H)-dione |

Compounds of formula (I), (IA), and (II) are known in the art and can be prepared by the methods of WO 2008/079814, which is hereby incorporated by reference in its entirety. In one embodiment, the compound of formula (I) (IA), or (I) is 3-[(2R)-2,3-dihydroxypropyl]-6-fluoro-5-[(2-fluoro-4-iodophenyl)amino]-8-methylpyrido[2,3-d]pyrimidine-4,7(3H,8H)-dione (TAK-733), or a pharmaceutically acceptable salt thereof.

Any molecule capable of selectively inhibiting the enzymatic activity of Aurora A kinase may be used in the methods, pharmaceutical compositions, and kits of the present invention. In some embodiments the selective Aurora A kinase inhibitor is a small molecular weight compound. In particular, selective inhibitors of Aurora A kinase include the compounds described herein, as well as compounds disclosed in, for example, US Publication No. 2008/0045501, U.S. Pat. No. 7,572,784, WO 05/111039, WO 08/021,038, U.S. Pat. No. 7,718,648, WO 08/063,525, US Publication No. 2008/0167292, U.S. Pat. No. 8,026,246, WO 10/134,965, US Publication No. 2010/0310651, WO 11/014,248, US Publication No. 2011/0039826, and US Publication No. 2011/0245234, each of which is hereby incorporated by reference in its entirety, as well as the compounds sodium 4-{[9-chloro-7-(2-fluoro-6-methoxyphenyl)-5H-pyrimido[5,4-d][2]benzazepin-2-yl]amino}-2-methoxybenzoate, KW-2449 (Kyowa), ENMD-2076 (EntreMed), and MK-5108 (Vertex/Merck). Also suitable for use in the methods, pharmaceutical compositions, and kits of the invention are solvated and hydrated forms of any of these compounds. Also suitable for use in the methods, pharmaceutical compositions, and kits of the invention are pharmaceutically acceptable salts of any of the compounds, and solvated and hydrated forms of such salts. These selective Aurora A kinase inhibitors can be prepared in a number of ways well known to one skilled in the art of organic synthesis, including, but not limited to, the methods of synthesis described in detail in the references referred to herein.

Aurora A kinase inhibitors can be assayed in vitro or in vivo for their ability to selectively bind to and/or inhibit an Aurora A kinase. In vitro assays include assays to determine selective inhibition of the ability of an Aurora A kinase to phosphorylate a substrate protein or peptide. Alternate in vitro assays quantitate the ability of the compound to selectively bind to an Aurora A kinase. Selective inhibitor binding may be measured by radiolabelling the inhibitor prior to binding, isolating the inhibitor/Aurora A kinase complex and determining the amount of radiolabel bound. Alternatively, selective inhibitor binding may be determined by running a competition experiment in which new inhibitors are incubated with Aurora A kinase bound to a known radioligand. The compounds also can be assayed for their ability to affect cellular or physiological functions mediated by Aurora A kinase activity. In order to assess selectivity for Aurora A kinase over Aurora B kinase, inhibitors can also be assayed in vitro and in vivo for their ability to selectively bind to and/or inhibit an Aurora B kinase, using assays analogous to those described above for Aurora A kinase. Inhibitors can be assayed in vitro and in vivo for their ability to inhibit Aurora A kinase in the absence of Aurora B kinase inhibition, by immunofluorescent detection of pH is H3. (*Proc. Natl. Acad. Sci.* (2007) 104, 4106). Assays for each of these activities are known in the art.

In some embodiments, the selective Aurora A kinase inhibitor is a compound represented by formula (III):

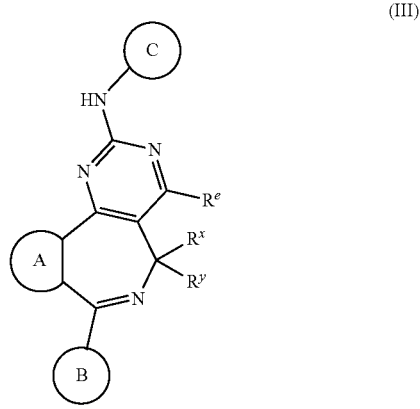

(III)

or a pharmaceutically acceptable salt thereof;
wherein:
Ring A is a substituted or unsubstituted 5- or 6-membered aryl, heteroaryl, cycloaliphatic, or heterocyclyl ring;
Ring B is a substituted or unsubstituted aryl, heteroaryl, cycloaliphatic, or heterocyclyl ring;
Ring C is a substituted or unsubstituted aryl, heteroaryl, heterocyclyl, or cycloaliphatic ring;
$R^c$ is hydrogen, —$OR^5$, —$N(R^4)_2$, —$SR^5$, or a $C_{1-3}$ aliphatic optionally substituted with $R^3$ or $R^7$;
each of $R^x$ and $R^y$ independently is hydrogen, fluoro, or an optionally substituted $C_{1-6}$ aliphatic; or Rx and $R^Y$, taken together with the carbon atom to which they are attached, form an optionally substituted 3- to 6-membered cycloaliphatic ring;
each $R^3$ independently is selected from the group consisting of -halo, —OH, —O($C_{1-3}$ alkyl), —CN, —$N(R^4)_2$, —C(O)($C_{1-3}$ alkyl), —$CO_2H$, —$CO_2(C_{1-3}$alkyl), —C(O)$NH_2$, and —C(O)NH($C_{1-3}$alkyl);
each $R^4$ independently is hydrogen or an optionally substituted aliphatic, aryl, heteroaryl, or heterocyclyl group; or two $R^4$ on the same nitrogen atom, taken together with the nitrogen atom, form an optionally substituted 5- to 6-membered heteroaryl or 4- to 8-membered heterocyclyl ring having, in addition to the nitrogen atom, 0-2 ring heteroatoms selected from N, O, and S;
each $R^5$ independently is hydrogen or an optionally substituted aliphatic, aryl, heteroaryl, or heterocyclyl group; and
each $R^7$ independently is an optionally substituted aryl, heterocyclyl, or heteroaryl group.

Ring A is a substituted or unsubstituted 5- or 6-membered aryl, heteroaryl, cycloaliphatic, or heterocyclyl ring. Examples of Ring A include furano, dihydrofurano, thieno, dihydrothieno, cyclopenteno, cyclohexeno, 2H-pyrrolo, pyrrolo, pyrrolino, pyrrolidino, oxazolo, thiazolo, imidazolo, imidazolino, imidazolidino, pyrazolo, pyrazolino, pyrazolidino, isoxazolo, isothiazolo, oxadiazolo, triazolo, thiadiazolo, 2H-pyrano, 4H-pyrano, benzo, pyridino, piperidino, dioxano, morpholino, dithiano, thiomorpholino, pyridazino, pyrimidino, pyrazino, piperazino, and triazino, any of which groups may be substituted or unsubstituted. Preferred values for Ring A include, without limitation, substituted or unsubstituted rings selected from the group consisting of furano, thieno, pyrrolo, oxazolo, thiazolo, imidazolo, pyrazolo, isoxazolo, isothiazolo, triazolo, benzo, pyridino, pyridazino, pyrimidino, and pyrazino.

Ring A may be substituted or unsubstituted. In some embodiments, each substitutable saturated ring carbon atom in Ring A is unsubstituted or is substituted with =O, =S, =C($R^5$)$_2$, =N—N($R^4$)$_2$, =N—$OR^5$, =N—NHC(O)$R^5$, =N—NHCO$_2R^6$, =N—NHSO$_2R^6$, =N—$R^5$ or —$R^b$, where $R^b$, $R^4$, $R^5$, and $R^6$ are as defined below. Each substitutable unsaturated ring carbon atom in Ring A is unsubstituted or substituted with —$R^b$. Each substitutable ring nitrogen atom in Ring A is unsubstituted or is substituted with —$R^{9b}$, and one ring nitrogen atom in Ring A optionally is oxidized. Each $R^{9b}$ independently is —C(O)$R^5$, —C(O)N($R^4$)$_2$, —$CO_2R^6$, —$SO_2R^6$, —$SO_2N(R^4)_2$, or a $C_{1-4}$ aliphatic optionally substituted with $R^3$ or $R^7$.

Each $R^b$ independently is $R^{2b}$, an optionally substituted aliphatic, or an optionally substituted aryl, heterocyclyl, or heteroaryl group; or two adjacent $R^b$, taken together with the intervening ring atoms, form an optionally substituted fused 4- to 8-membered aromatic or non-aromatic ring having 0-3 ring heteroatoms selected from the group consisting of O, N, and S.

Each $R^{2b}$ independently is -halo, —$NO_2$, —CN, —C($R^5$) =C($R^5$)$_2$, —C($R^5$)=C($R^5$)($R^{10}$), —C=C—$R^5$, —C≡C—$R^{10}$, —$OR^5$, —S $R^6$, —S(O)$R^6$, —$SO_2R^6$, —$SO_2N(R^4)_2$, —N($R^4$)$_2$, —$NR^4C(O)R^5$, —$NR^4C(O)N(R^4)_2$, —$NR^4CO_2R^6$, —O—$CO_2R^5$, —OC(O)N($R^4$)$_2$, —O—C(O)$R^5$, —$CO_2R^5$, —C(O)—C(O)$R^5$, —C(O)$R^5$, —C(O)N($R^4$)$_2$, —C(=$NR^4$)—N($R^4$)$_2$, —C(=$NR^4$)—$OR^5$, —N($R^4$)—N($R^4$)$_2$, N($R^4$)C(=$NR^4$)—N($R^4$)$_2$, —N($R^4$)SO$_2R^6$, —N($R^4$)SO$_2$N($R^4$)$_2$, —P(O)($R^5$)$_2$, or —P(O)(O$R^5$)$_2$, where the variables $R^4$, $R^5$, and $R^7$ have the values described above; each $R^6$ independently is an optionally substituted aliphatic or aryl group; and each $R^{10}$ independently is $—CO_2R^5$ or $—C(O)N(R^4)_2$.

In some embodiments, Ring A is substituted by 0-2 substituents $R^b$. In some such embodiments, each $R^b$ independently is $C_{1-3}$ aliphatic or $R^{2b}$, and each $R^{2b}$ independently is selected from the group consisting of -halo, $—NO_2$, $—C(R^5)=C(R^5)_2$, $—C≡C—R^5$, $—OR^5$, and $—N(R^4)_2$. In some embodiments, each $R^b$ independently is selected from the group consisting of -halo, $C_{1-3}$ aliphatic, $C_{1-3}$ fluoroaliphatic, and $—OR^5$, where $R^5$ is hydrogen or $C_{1-3}$ aliphatic. In certain preferred embodiments, Ring A is substituted with 0, 1, or 2 substituents, preferably 0 or 1 substituents, independently selected from the group consisting of chloro, fluoro, bromo, methyl, trifluoromethyl, and methoxy.

In some embodiments, Ring B is a substituted or unsubstituted mono- or bicyclic aryl or heteroaryl ring selected from the group consisting of furanyl, thienyl, pyrrolyl, oxazolyl, thiazolyl, imidazolyl, pyrazolyl, isoxazolyl, isothiazolyl, oxadiazolyl, triazolyl, thiadiazolyl, phenyl, pyridyl, pyridazinyl, pyrimidinyl, pyrazinyl, triazinyl, indolizinyl, indolyl, isoindolyl, indazolyl, benzo[b]furanyl, benzo[b]thienyl, benzimidazolyl, benzthiazolyl, benzoxazolyl, purinyl, quinolyl, isoquinolyl, cinnolinyl, phthalazinyl, quinazolinyl, quinoxalinyl, naphthyridinyl, and pteridinyl.

Each substitutable saturated ring carbon atom in Ring B is unsubstituted or is substituted with $=O$, $=S$, $=C(R^5)_2$, $=N—N(R^4)_2$, $=N—OR^5$, $=N—NHC(O)R^5$, $=N—NHCO_2R^6$, $=N—NHSO_2R^6$, $=N—R^5$ or $—R^c$. Each substitutable unsaturated ring carbon atom in Ring B is unsubstituted or substituted with $—R^c$. Each substitutable ring nitrogen atom in Ring B is unsubstituted or is substituted with $—R^{9c}$, and one ring nitrogen atom in Ring B optionally is oxidized. Each $R^{9c}$ independently is $—C(O)R^5$, $—C(O)N(R^4)_2$, $—CO_2R^6$, $—SO_2R^6$, $—SO_2N(R^4)_2$, or a $C_{1-4}$ aliphatic optionally substituted with $R^3$ or $R^7$. Ring B may be unsubstituted or may be substituted on any one or more of its component rings, wherein the substituents may be the same or different. In some embodiments, Ring B is substituted with 0-2 independently selected $R^c$ and 0-3 independently selected $R^{2c}$ or $C_{1-6}$ aliphatic groups. The variables $R^3$, $R^4$, R, $R^6$, and $R^7$ are as defined above for Ring A, and $R^c$ and $R^{2c}$ are defined below.

Each $R^c$ independently is $R^{2c}$, an optionally substituted $C_{1-6}$ aliphatic, or an optionally substituted aryl, heteroaryl, or heterocyclyl group.

Each $R^{2c}$ independently is -halo, $—NO_2$, $—CN$, $—C(R^5)=C(R)_2$, $—C(R^5)=C(R^5)(R^{11})$, $—C≡C—R^5$, $—C≡C—R^{10}$, $—OR^5$, $—SR^6$, $—S(O)R^6$, $—SO_2R^6$, $—SO_2N(R^4)_2$, $—N(R^4)_2$, $—NR^4C(O)R^5$, $—NR^4C(O)N(R^4)_2$, $—NR^4CO_2R^6$, $—O—CO_2R^5$, $—OC(O)N(R^4)_2$, $—O—C(O)R^5$, $—CO_2R^5$, $—C(O)—C(O)R^5$, $—C(O)R^5$, $—C(O)N(R^4)_2$, $—C(=NR^4)—N(R^4)_2$, $—C(=NR^4)—OR^5$, $—N(R^4)—N(R^4)_2$, $—N(R^4)C(=NR^4)—N(R^4)_2$, $—N(R^4)SO_2R^6$, $—N(R^4)SO_2N(R^4)_2$, $—P(O)(R^5)_2$, or $—P(O)(OR^5)_2$.

In some embodiments, Ring B is a monocyclic 5- or 6-membered aryl or heteroaryl ring, substituted with 0-2 independently selected $R^c$ and 0-2 independently selected $R^{2c}$ or $C_{1-6}$ aliphatic groups. In certain such embodiments, Ring B is a substituted or unsubstituted phenyl or pyridyl ring.

In some embodiments, Ring B is substituted with 0-2 substituents R. In some such embodiments, each $R^c$ independently is $C_{1-3}$ aliphatic or $R^2$, and each $R^{2c}$ independently is selected from the group consisting of -halo, $—NO_2$, $—C(R^5)=C(R^5)_2$, $—C≡C—R^5$, $—OR^5$, and $—N(R^4)_2$. In some embodiments, each $R^c$ independently is selected from the group consisting of -halo, $C_{1-3}$ aliphatic, $C_{1-3}$ haloaliphatic, and $—OR^5$, where $R^5$ is hydrogen or $C_{1-3}$ aliphatic. In certain preferred embodiments, Ring B is substituted with 0, 1, or 2 substituents, independently selected from the group consisting of chloro, fluoro, bromo, methyl, trifluoromethyl, and methoxy.

Each substitutable saturated ring carbon atom in Ring C is unsubstituted or is substituted with $=O$, $=S$, $=C(R^5)_2$, $=N—N(R^4)_2$, $=N—OR^5$, $=N—NHC(O)R^5$, $=N—NHCO_2R^6$, $=N—NHSO_2R^6$, $=N—R^5$ or $—R^d$. Each substitutable unsaturated ring carbon atom in Ring C is unsubstituted or substituted with $—R^d$. Each substitutable ring nitrogen atom in Ring C is unsubstituted or is substituted with $—R^{9d}$, and one ring nitrogen atom in Ring C optionally is oxidized. Each $R^{9d}$ independently is $—C(O)R^5$, $—C(O)N(R^4)_2$, $—CO_2R^6$, $—SO_2R^6$, $—SO_2N(R^4)_2$, or a $C_{1-4}$ aliphatic optionally substituted with $R^3$ or $R^7$. Ring C may be unsubstituted or may be substituted on any one or more of its component rings, wherein the substituents may be the same or different. In some embodiments, Ring C is substituted with 0-2 independently selected $R^d$ and 0-3 independently selected $R^{2d}$ or $C_{1-6}$ aliphatic groups. The variables $R^3$, $R^4$, $R^5$, $R^6$, and $R^7$ are as described above for Rings A and B. The variables $R^d$ and $R^{2d}$ are described below.

Each $R^d$ independently is $R^{2d}$, an optionally substituted aliphatic, or an optionally substituted aryl, heteroaryl, or heterocyclyl group.

Each $R^{2d}$ independently is -halo, $—NO_2$, $—CN$, $—C(R^5)=C(R^5)_2$, $—C(R^5)=C(R^5)_2(R^{10})$, $—C≡C—R^5$, $—C≡C—R^{10}$, $—OR^5$, $—SR^6$, $—S(O)R^6$, $—SO_2R^6$, $—SO_2N(R^4)_2$, $—N(R^4)_2$, $—NR^4C(O)R^5$, $—NR^4C(O)N(R^4)_2$, $—NR^4CO_2R^6$, $—O—CO_2R^5$, $—OC(O)N(R^4)_2$, $—O—C(O)R^5$, $—CO_2R^5$, $—C(O)—C(O)R^5$, $—C(O)R^5$, $—C(O)N(R^4)_2$, $—C(=NR^4)—N(R^4)_2$, $—C(=NR^4)—OR^5$, $—N(R^4)—N(R^4)_2$, $—N(R^4)C(=NR^4)—N(R^4)_2$, $—N(R^4)SO_2R^6$, $—N(R^4)SO_2N(R^4)_2$, $—P(O)(R^5)_2$, or $—P(O)(OR^5)_2$. Additionally, $R^{2d}$ can be $—SO_3R^5$, $—C(O)N(R^4)C(=NR^4)—N(R^4)_2$ or $—N(R^4)C(=NR^4)—N(R^4)—C(O)R^5$.

In some embodiments, Ring C is a monocyclic 5- or 6-membered aryl or heteroaryl ring, which is substituted with 0-2 independently selected substituents $R^d$ and 0-2 independently selected $R^{2d}$ or $C_{1-6}$ aliphatic groups. In some such embodiments, Ring C is an optionally substituted heteroaryl ring selected from the group consisting of pyridyl, pyrimidinyl, pyrazinyl, pyridazinyl, imidazolyl, pyrazolyl, and oxazolyl. In some other embodiments, Ring C is a substituted or unsubstituted phenyl ring. In some embodiments, Ring C is a monocyclic 5- or 6-membered aryl or heteroaryl ring, which is substituted with 0, 1, or 2 substituents $R^d$, as defined above.

In some other embodiments, Ring C is a monocyclic 5- or 6-membered heterocyclyl or cycloaliphatic ring, which is substituted with 0-2 independently selected substituents $R^d$ and 0-2 independently selected $R^{2d}$ or $C_{1-6}$ aliphatic groups.

In some embodiments, the selective Aurora A kinase inhibitor is a compound represented by formula (IV):

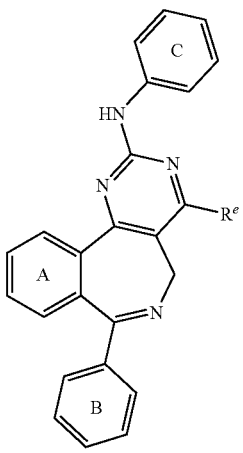

(IV)

or a pharmaceutically acceptable salt thereof;
wherein:
$R^e$ is hydrogen or a $C_{1-3}$ aliphatic optionally substituted with $R^3$ or $R^7$;
Ring A is substituted with 0-3 $R^b$;
  each $R^b$ independently is selected from the group consisting of $C_{1-6}$ aliphatic, $R^{2b}$, $R^{7b}$, -$T^1$-$R^{2b}$, and -T-$R^{7b}$;
  each $R^{2b}$ independently is -halo, —$NO_2$, —CN, —C($R^5$)=C($R^5$)$_2$, —C≡C—$R^5$, —$OR^5$, —$SR^6$, —S(O)$R^6$, —$SO_2R^6$, —$SO_2N(R^4)_2$, —N($R^4$)$_2$, —$NR^4C(O)R^5$, —$NR^4C(O)N(R^4)_2$, —$NR^4CO_2R^6$, —O—$CO_2R^5$, —OC(O)N($R^4$)$_2$, —O—C(O)$R^5$, —$CO_2R^5$, —C(O)—C(O)$R^5$, —C(O)$R^5$, —C(O)N($R^4$)$_2$, —C(=$NR^4$)—N($R^4$)$_2$, —C(=$NR^4$)—$OR^5$, —N($R^4$)—N($R^4$)$_2$, —N($R^4$)C(=$NR^4$)—N($R^4$)$_2$, —N($R^4$)$SO_2R^6$, —N($R^4$)$SO_2N(R^4)_2$, —P(O)($R^5$)$_2$, or —P(O)($OR^5$)$_2$;
  each $R^{7b}$ independently is an optionally substituted aryl, heterocyclyl, or heteroaryl group;
Ring B is substituted with 0-2 independently selected $R^c$ and 0-2 independently selected $R^{2c}$ or $C_{1-6}$ aliphatic groups;
  each $R^c$ independently is selected from the group consisting of $C_{1-6}$ aliphatic, $R^{2c}$, $R^7$, -$T^1$-$R^{2c}$, and -T-$R^{7c}$;
  each $R^{2c}$ independently is -halo, —$NO_2$, —CN, —C($R^5$)=C($R^5$)$_2$, —C≡C—$R^5$, —$OR^5$, —$SR^6$, —S(O)$R^6$, —$SO_2R^6$, —$SO_2N(R^4)_2$, —N($R^4$)$_2$, —$NR^4C(O)R^5$, —$NR^4C(O)N(R^4)_2$, —$NR^4CO_2R^6$, —O—$CO_2R^5$, —OC(O)N($R^4$)$_2$, —O—C(O)$R^5$, —$CO_2R^5$, —C(O)—C(O)$R^5$, —C(O)$R^5$, —C(O)N($R^4$)$_2$, —C(=$NR^4$)—N($R^4$)$_2$, —C(=$NR^4$)—$OR^5$, —N($R^4$)—N($R^4$)$_2$, —N($R^4$)C(=$NR^4$)—N($R^4$)$_2$, —N($R^4$)$SO_2R^6$, —N($R^4$)$SO_2N(R^4)_2$, —P(O)($R^5$)$_2$, or —P(O)($OR^5$)$_2$;
  each $R^{7c}$ independently is an optionally substituted aryl, heterocyclyl, or heteroaryl group;
$T^1$ is a $C_{1-6}$ alkylene chain optionally substituted with $R^3$ or $R^{3b}$, wherein $T^1$ or a portion thereof optionally forms part of a 3- to 7-membered ring;
Ring C is substituted with 0-2 independently selected $R^d$ and 0-3 independently selected $R^{2d}$ or $C_{1-6}$ aliphatic groups;
  each $R^d$ independently is selected from the group consisting of $C_{1-6}$ aliphatic, $R^{2d}$, $R^{7d}$, -$T^2$-$R^{2d}$, -$T^2$-$R^{7d}$, -V-$T^3$-$R^{2d}$, and -V-$T^3$-$R^{7d}$;
  $T^2$ is a $C_{1-6}$ alkylene chain optionally substituted with $R^3$ or $R^{3b}$, wherein the alkylene chain optionally is interrupted by —C($R^5$)=C($R^5$)—, —C≡C—, —O—, —S—, —S(O)—, —S(O)$_2$—, —$SO_2N(R^4)$—, —N($R^4$)—, —N($R^4$)C(O)—, —$NR^4C(O)N(R^4)$—, —N($R^4$)$CO_2$—, —C(O)N($R^4$)—, —C(O)—, —C(O)—C(O)—, —$CO_2$—, —OC(O)—, —OC(O)O—, —OC(O)N($R^4$)—, —N($R^4$)—N($R^4$)—, —N($R^4$)$SO_2$—, or —$SO_2N(R^4)$—, and wherein $T^2$ or a portion thereof optionally forms part of a 3-7 membered ring;

$T^3$ is a $C_{1-6}$ alkylene chain optionally substituted with $R^3$ or $R^{3b}$, wherein the alkylene chain optionally is interrupted by —C($R^5$)=C($R^5$)—, —C≡C—, —O—, —S—, —S(O)—, —S(O)$_2$—, —$SO_2N(R^4)$—, —N($R^4$)—, —N($R^4$)C(O)—, —$NR^4C(O)N(R^4)$—, —N($R^4$)$CO_2$—, —C(O)N($R^4$)—, —C(O)—, —C(O)—C(O)—, —$CO_2$—, —OC(O)—, —OC(O)O—, —OC(O)N($R^4$)—, —N($R^4$)—N($R^4$)—, —N($R^4$)$SO_2$—, or —$SO_2N(R^4)$—, and wherein $T^3$ or a portion thereof optionally forms part of a 3-7 membered ring;

V is —C($R^5$)=C($R^5$)—, —C≡C—, —O—, —S—, —S(O)—, —S(O)$_2$—, —$SO_2N(R^4)$—, —N($R^4$)—, —N($R^4$)C(O)—, —$NR^4C(O)N(R^4)$—, —N($R^4$)$CO_2$—, —C(O)N($R^4$)—, —C(O)—, —C(O)—C(O)—, —$CO_2$—, —OC(O)—, —OC(O)O—, —OC(O)N($R^4$)—, —C($NR^4$)=N—, —C($OR^5$)=N—, —N($R^4$)—N($R^4$)—, —N($R^4$)$SO_2$—, —N($R^4$)$SO_2$N($R^4$)—, —P(O)($R^5$)—, —P(O)($OR^5$)—O—, —P(O)—O—, or —P(O)(N$R^5$)—N($R^5$)—;

$R^{2d}$ is -halo, —$NO_2$, —CN, —C($R^5$)=C($R^5$)$_2$, —C≡C—$R^5$, —$OR^5$, —$SR^6$, —S(O)$R^6$, —$SO_2R^6$, —$SO_2N(R^4)_2$, —N($R^4$)$_2$, —$NR^4C(O)R^5$, —$NR^4C(O)N(R^4)_2$, —$NR^4CO_2R^6$, —O—$CO_2R^5$, —OC(O)N($R^4$)$_2$, —O—C(O)$R^5$, —$CO_2R^5$, —C(O)—C(O)$R^5$, —C(O)$R^5$, —C(O)N($R^4$)$_2$, —C(=$NR^4$)—N($R^4$)$_2$, —C(=$NR^4$)—$OR^5$, —N($R^4$)—N($R^4$)$_2$, —N($R^4$)C(=$NR^4$)—N($R^4$)$_2$, —N($R^4$)$SO_2R^6$, —N($R^4$)$SO_2N(R^4)_2$, —P(O)($R^5$)$_2$, or —P(O)($OR^5$)$_2$; and each $R^{7d}$ independently is an optionally substituted aryl, heterocyclyl, or heteroaryl group.

each $R^3$ independently is selected from the group consisting of -halo, —OH, —O($C_{1-3}$alkyl), —CN, —N($R^4$)$_2$, —C(O)($C_{1-3}$ alkyl), —$CO_2H$, —$CO_2$($C_{1-3}$ alkyl), —C(O)$NH_2$, and —C(O)NH($C_{1-3}$ alkyl);

each $R^{3b}$ independently is a $C_{1-3}$ aliphatic optionally substituted with $R^3$ or $R^7$, or two substituents $R^{3b}$ on the same carbon atom, taken together with the carbon atom to which they are attached, form a 3- to 6-membered carbocyclic ring;

each $R^4$ independently is hydrogen or an optionally substituted aliphatic, aryl, heteroaryl, or heterocyclyl group; or two $R^4$ on the same nitrogen atom, taken together with the nitrogen atom, form an optionally substituted 5- to 8-membered heteroaryl or heterocyclyl ring having, in addition to the nitrogen atom, 0-2 ring heteroatoms selected from N, O, and S;

each $R^5$ independently is hydrogen or an optionally substituted aliphatic, aryl, heteroaryl, or heterocyclyl group;

each $R^6$ independently is an optionally substituted aliphatic or aryl group; and each $R^7$ independently is an optionally substituted aryl, heterocyclyl, or heteroaryl group.

Table 2 provides the chemical names for specific examples of compounds of formula (IV).

TABLE 2

| | Examples of Compounds of Formula (IV) |
|---|---|
| IV-1 | 4-[9-Chloro-7-(2-fluoro-phenyl)-5H-benzo[c]pyrimido[4,5-e]azepin-2-ylamino]-N-(2-methylamino-ethyl)-benzamide |
| IV-2 | N-(2-Amino-ethyl)-4-[9-chloro-7-(2-fluoro-phenyl)-5H-benzo[c]pyrimido-[4,5-e]azepin-2-ylamino]-N-methyl-benzamide |
| IV-3 | 4-[9-Chloro-7-(2-fluoro-phenyl)-5H-benzo[c]pyrimido[4,5-e]azepin-2-ylamino]-N-methyl-N-(2-methylamino-ethyl)-benzamide |
| IV-4 | 4-[9-Chloro-7-(2-fluoro-phenyl)-5H-benzo[c]pyrimido[4,5-e]azepin-2-ylamino]-N-(2-dimethylamino-ethyl)-benzamide |
| IV-5 | 4-[9-Chloro-7-(2-fluoro-phenyl)-5H-benzo[c]pyrimido[4,5-e]azepin-2-ylamino]-N-(2-dimethylamino-ethyl)-N-methyl-benzamide |
| IV-6 | 4-[9-Chloro-7-(2-fluoro-phenyl)-5H-benzo[c]pyrimido[4,5-e]azepin-2-ylamino]-N-(3-dimethylamino-propyl)-benzamide |
| IV-7 | 4-[9-Chloro-7-(2-fluoro-phenyl)-5H-benzo[c]pyrimido[4,5-e]azepin-2-ylamino]-N-(3-dimethylamino-propyl)-N-methyl-benzamide |
| IV-8 | {4-[9-Chloro-7-(2-fluoro-phenyl)-5H-benzo[c]pyrimido[4,5-e]azepin-2-ylamino]-phenyl}-piperazin-1-yl-methanone |
| IV-9 | {4-[9-Chloro-7-(2-fluoro-phenyl)-5H-benzo[c]pyrimido[4,5-e]azepin-2-ylamino]-phenyl}-(4-methyl-piperazin-1-yl)-methanone |
| IV-10 | {4-[9-Chloro-7-(2-chloro-phenyl)-5H-benzo[c]pyrimido[4,5-e]azepin-2-ylamino]-phenyl}-(4-methyl-piperazin-1-yl)-methanone |
| IV-11 | [4-(9-Chloro-7-o-tolyl-5H-benzo[c]pyrimido[4,5-e]azepin-2-ylamino)-phenyl]-(4-methyl-piperazin-1-yl)-methanone |
| IV-12 | {4-[9-Chloro-7-(2-methoxy-phenyl)-5H-benzo[c]pyrimido[4,5-e]azepin-2-ylamino]-phenyl}-(4-methyl-piperazin-1-yl)-methanone |
| IV-13 | {4-[9-Chloro-7-(4-fluoro-phenyl)-5H-benzo[c]pyrimido[4,5-e]azepin-2-ylamino]-phenyl}-(4-methyl-piperazin-1-yl)-methanone |
| IV-14 | {4-[7-(2-Fluoro-phenyl)-9-methyl-5H-benzo[c]pyrimido[4,5-e]azepin-2-ylamino]-phenyl}-(4-methyl-piperazin-1-yl)-methanone |
| IV-15 | 2-{3-[9-Chloro-7-(2-fluoro-phenyl)-5H-benzo[c]pyrimido[4,5-e]azepin-2-ylamino]-phenyl}-1-(4-methyl-piperazin-1-yl)-ethanone |
| IV-16 | 4-[9-Chloro-7-(2-fluoro-phenyl)-5H-benzo[c]pyrimido[4,5-e]azepin-2-ylamino]-N-piperidin-4-yl-benzamide |
| IV-17 | (4-Amino-piperidin-1-yl)-{4-[9-chloro-7-(2-fluoro-phenyl)-5H-benzo[c]pyrimido[4,5-e]azepin-2-ylamino]-phenyl}-methanone |
| IV-18 | {4-[9-Chloro-7-(2-fluoro-phenyl)-5H-benzo[c]pyrimido[4,5-e]azepin-2-ylamino]-phenyl}-(4-dimethylamino-piperidin-1-yl)-methanone |
| IV-19 | 4-[9-Chloro-7-(2-fluoro-phenyl)-5H-benzo[c]pyrimido[4,5-e]azepin-2-ylamino]-N-[3-(4-methyl-piperazin-1-yl)-propyl]-benzamide |
| IV-20 | 4-[9-Chloro-7-(2-chloro-phenyl)-5H-benzo[c]pyrimido[4,5-e]azepin-2-ylamino]-N-[3-(4-methyl-piperazin-1-yl)-propyl]-benzamide |
| IV-21 | 4-(9-Chloro-7-o-tolyl-5H-benzo[c]pyrimido[4,5-e]azepin-2-ylamino)-N-[3-(4-methyl-piperazin-1-yl)-propyl]-benzamide |
| IV-22 | 4-[9-Chloro-7-(2-methoxy-phenyl)-5H-benzo[c]pyrimido[4,5-e]azepin-2-ylamino]-N-[3-(4-methyl-piperazin-1-yl)-propyl]-benzamide |
| IV-23 | 4-[9-Chloro-7-(4-fluoro-phenyl)-5H-benzo[c]pyrimido[4,5-e]azepin-2-ylamino]-N-[3-(4-methyl-piperazin-1-yl)-propyl]-benzamide |
| IV-24 | 4-[7-(2-Fluoro-phenyl)-9-methyl-5H-benzo[c]pyrimido[4,5-e]azepin-2-ylamino]-N-[3-(4-methyl-piperazin-1-yl)-propyl]-benzamide |
| IV-25 | 2-{3-[9-Chloro-7-(2-fluoro-phenyl)-5H-benzo[c]pyrimido[4,5-e]azepin-2-ylamino]-phenyl}-N-[3-(4-methyl-piperazin-1-yl)-propyl]-acetamide |
| IV-26 | {4-[9-Chloro-7-(2-fluoro-phenyl)-5H-benzo[c]pyrimido[4,5-e]azepin-2-ylamino]-phenyl}-morpholin-4-yl-methanone |
| IV-27 | 4-[9-Chloro-7-(2-fluoro-phenyl)-5H-benzo[c]pyrimido[4,5-e]azepin-2-ylamino]-N,N-bis-(2-hydroxy-ethyl)-benzamide |
| IV-28 | {4-[9-Chloro-7-(2-chloro-phenyl)-5H-benzo[c]pyrimido[4,5-e]azepin-2-ylamino]-phenyl}-morpholin-4-yl-methanone |
| IV-29 | 4-[9-Chloro-7-(2-fluoro-phenyl)-5H-benzo[c]pyrimido[4,5-e]azepin-2-ylamino]-N-(2-morpholin-4-yl-ethyl)-benzamide |
| IV-30 | 4-[9-Chloro-7-(2-chloro-phenyl)-5H-benzo[c]pyrimido[4,5-e]azepin-2-ylamino]-N-(2-morpholin-4-yl-ethyl)-benzamide |
| IV-31 | 4-(9-Chloro-7-o-tolyl-5H-benzo[c]pyrimido[4,5-e]azepin-2-ylamino)-N-(2-morpholin-4-yl-ethyl)-benzamide |
| IV-32 | 4-[9-Chloro-7-(2-methoxy-phenyl)-5H-benzo[c]pyrimido[4,5-e]azepin-2-ylamino]-N-(3-morpholin-4-yl-propyl)-benzamide |
| IV-33 | 4-[9-Chloro-7-(4-fluoro-phenyl)-5H-benzo[c]pyrimido[4,5-e]azepin-2-ylamino]-N-(2-morpholin-4-yl-ethyl)-benzamide |
| IV-34 | 4-[9-Chloro-7-(2-chloro-phenyl)-5H-benzo[c]pyrimido[4,5-e]azepin-2-ylamino]-2-hydroxy-N-(2-morpholin-4-yl-ethyl)-benzamide |
| IV-35 | [9-Chloro-7-(2-chloro-phenyl)-5H-benzo[c]pyrimido[4,5-e]azepin-2-yl]-pyridin-2-yl-amine |
| IV-36 | [9-Chloro-7-(2-fluoro-phenyl)-5H-benzo[c]pyrimido[4,5-e]azepin-2-yl]-(3,5-dichloro-phenyl)-amine |
| IV-37 | [9-Chloro-7-(2-fluoro-phenyl)-5H-benzo[c]pyrimido[4,5-e]azepin-2-yl]-(4-methoxy-phenyl)-amine |
| IV-38 | [9-Chloro-7-(2-fluoro-phenyl)-5H-benzo[c]pyrimido[4,5-e]azepin-2-yl]-(4-ethoxy-phenyl)-amine |
| IV-39 | [9-Chloro-7-(2-fluoro-phenyl)-5H-benzo[c]pyrimido[4,5-e]azepin-2-yl]-(3-methoxy-phenyl)-amine |

TABLE 2-continued

Examples of Compounds of Formula (IV)

| | |
|---|---|
| IV-40 | [9-Chloro-7-(2-fluoro-phenyl)-5H-benzo[c]pyrimido[4,5-e]azepin-2-yl]-(2-methoxy-phenyl)-amine |
| IV-41 | [9-Chloro-7-(2-fluoro-phenyl)-5H-benzo[c]pyrimido[4,5-e]azepin-2-yl]-(4-chloro-phenyl)-amine |
| IV-42 | [9-Chloro-7-(2-chloro-phenyl)-5H-benzo[c]pyrimido[4,5-e]azepin-2-yl]-(4-chloro-phenyl)-amine |
| IV-43 | [9-Chloro-7-(2-fluoro-phenyl)-5H-benzo[c]pyrimido[4,5-e]azepin-2-yl]-(3-chloro-phenyl)-amine |
| IV-44 | [9-Chloro-7-(2-fluoro-phenyl)-5H-benzo[c]pyrimido[4,5-e]azepin-2-yl]-(2-chloro-phenyl)-amine |
| IV-45 | 4-[9-Chloro-7-(2-chloro-phenyl)-5H-benzo[c]pyrimido[4,5-e]azepin-2-ylamino]-phenol |
| IV-46 | [9-Chloro-7-(2-fluoro-phenyl)-5H-benzo[c]pyrimido[4,5-e]azepin-2-yl]-(4-morpholin-4-yl-phenyl)-amine |
| IV-47 | [9-Chloro-7-(2-fluoro-phenyl)-5H-benzo[c]pyrimido[4,5-e]azepin-2-yl]-[4-(4-methyl-piperazin-1-yl)-phenyl]-amine |
| IV-48 | [9-Chloro-7-(2-fluoro-phenyl)-5H-benzo[c]pyrimido[4,5-e]azepin-2-yl]-(4-pyridin-4-ylmethyl-phenyl)-amine |
| IV-49 | 4-[9-Chloro-7-(2-fluoro-phenyl)-5H-benzo[c]pyrimido[4,5-e]azepin-2-ylamino]-benzonitrile |
| IV-50 | [9-Chloro-7-(2-fluoro-phenyl)-5H-benzo[c]pyrimido[4,5-e]azepin-2-yl]-(4-nitro-phenyl)-amine |
| IV-51 | 4-[7-(2-Fluoro-phenyl)-5H-benzo[c]pyrimido[4,5-e]azepin-2-ylamino]-benzoic acid |
| IV-52 | 4-[9-Chloro-7-(2-fluoro-phenyl)-5H-benzo[c]pyrimido[4,5-e]azepin-2-ylamino]-benzoic acid |
| IV-53 | 4-[9-Chloro-7-(2-chloro-phenyl)-5H-benzo[c]pyrimido[4,5-e]azepin-2-ylamino]-benzoic acid |
| IV-54 | 4-(9-Chloro-7-o-tolyl-5H-benzo[c]pyrimido[4,5-e]azepin-2-ylamino)-benzoic acid |
| IV-55 | 4-[9-Chloro-7-(2-methoxy-phenyl)-5H-benzo[c]pyrimido[4,5-e]azepin-2-ylamino]-benzoic acid |
| IV-56 | 4-[9-Chloro-7-(4-fluoro-phenyl)-5H-benzo[c]pyrimido[4,5-e]azepin-2-ylamino]-benzoic acid |
| IV-57 | 4-[9-Fluoro-7-(2-fluoro-phenyl)-5H-benzo[c]pyrimido[4,5-e]azepin-2-ylamino]-benzoic acid |
| IV-58 | 4-[7-(2-Fluoro-phenyl)-9-methyl-5H-benzo[c]pyrimido[4,5-e]azepin-2-ylamino]-benzoic acid |
| IV-59 | 4-[10-Fluoro-7-(2-fluoro-phenyl)-5H-benzo[c]pyrimido[4,5-e]azepin-2-ylamino]-benzoic acid |
| IV-60 | 4-[10-Chloro-7-(2-fluoro-phenyl)-5H-benzo[c]pyrimido[4,5-e]azepin-2-ylamino]-benzoic acid |
| IV-61 | 4-[10-Bromo-7-(2-fluoro-phenyl)-5H-benzo[c]pyrimido[4,5-e]azepin-2-ylamino]-benzoic acid |
| IV-62 | 4-[7-(2-Fluoro-phenyl)-10-methoxy-5H-benzo[c]pyrimido[4,5-e]azepin-2-ylamino]-benzoic acid |
| IV-63 | 4-[9-Chloro-7-(2-chloro-phenyl)-5H-benzo[c]pyrimido[4,5-e]azepin-2-ylamino]-benzamide |
| IV-64 | 3-[9-Chloro-7-(2-chloro-phenyl)-5H-benzo[c]pyrimido[4,5-e]azepin-2-ylamino]-benzamide |
| IV-65 | {3-[9-Chloro-7-(2-chloro-phenyl)-5H-benzo[c]pyrimido[4,5-e]azepin-2-ylamino]-phenyl}-acetic acid |
| IV-66 | 2-{3-[9-Chloro-7-(2-chloro-phenyl)-5H-benzo[c]pyrimido[4,5-e]azepin-2-ylamino]-phenyl}-acetamide |
| IV-67 | 4-[9-Chloro-7-(2-fluoro-phenyl)-5H-benzo[c]pyrimido[4,5-e]azepin-2-ylamino]-benzenesulfonic acid |
| IV-68 | 4-[9-Chloro-7-(2-fluoro-phenyl)-5H-benzo[c]pyrimido[4,5-e]azepin-2-ylamino]-benzenesulfonamide |
| IV-69 | 4-[9-Chloro-7-(2-chloro-phenyl)-5H-benzo[c]pyrimido[4,5-e]azepin-2-ylamino]-N-(5-methyl-isoxazol-3-yl)-benzenesulfonamide |
| IV-70 | [9-Chloro-7-(2-fluoro-phenyl)-5H-benzo[c]pyrimido[4,5-e]azepin-2-yl]-(4-trifluoromethanesulfonyl-phenyl)-amine |
| IV-71 | [9-Chloro-7-(2-fluoro-phenyl)-5H-benzo[c]pyrimido[4,5-e]azepin-2-yl]-(3,4-dimethoxy-phenyl)-amine |
| IV-72 | [9-Chloro-7-(2-fluoro-phenyl)-6,7-dihydro-5H-benzo[c]pyrimido[4,5-e]azepin-2-yl]-(3,4-dimethoxy-phenyl)-amine |
| IV-73 | [9-Chloro-7-(2-chloro-phenyl)-5H-benzo[c]pyrimido[4,5-e]azepin-2-yl]-(3,4-dimethoxy-phenyl)-amine |
| IV-74 | (9-Chloro-7-o-tolyl-5H-benzo[c]pyrimido[4,5-e]azepin-2-yl)-(3,4-dimethoxy-phenyl)-amine |
| IV-75 | (3,4-Dimethoxy-phenyl)-[7-(2-fluoro-phenyl)-9-methyl-5H-benzo[c]pyrimido-[4,5-e]azepin-2-yl]-amine |
| IV-76 | (3,4-Dimethoxy-phenyl)-[7-(2-fluoro-phenyl)-9-isopropyl-5H-benzo[c]pyrimido[4,5-e]azepin-2-yl]-amine |
| IV-77 | (3,4-Dimethoxy-phenyl)-[10-fluoro-7-(2-fluoro-phenyl)-5H-benzo[c]pyrimido-[4,5-e]azepin-2-yl]-amine |
| IV-78 | [10-Bromo-7-(2-fluoro-phenyl)-5H-benzo[c]pyrimido[4,5-e]azepin-2-yl]-(3,4-dimethoxy-phenyl)-amine |

TABLE 2-continued

Examples of Compounds of Formula (IV)

| | |
|---|---|
| IV-79 | (3,4-Dimethoxy-phenyl)-[7-(2-fluoro-phenyl)-10-trifluoromethyl-5H-benzo[c]pyrimido[4,5-e]azepin-2-yl]-amine |
| IV-80 | (3,4-Dimethoxy-phenyl)-[7-(2-fluoro-phenyl)-10-methyl-5H-benzo[c]pyrimido-[4,5-e]azepin-2-yl]-amine |
| IV-81 | (3,4-Dimethoxy-phenyl)-[7-(2-fluoro-phenyl)-10-methoxy-5H-benzo[c]pyrimido[4,5-e]azepin-2-yl]-amine |
| IV-82 | (3,4-Dimethoxy-phenyl)-[7-(2-fluoro-phenyl)-11-methyl-5H-benzo[c]pyrimido-[4,5-e]azepin-2-yl]-amine |
| IV-83 | [9-Chloro-7-(2-fluoro-phenyl)-5H-benzo[c]pyrimido[4,5-e]azepin-2-yl]-(2,3-dihydro-benzo[1,4]dioxin-6-yl)-amine |
| IV-84 | [9-Chloro-7-(2-fluoro-phenyl)-5H-benzo[c]pyrimido[4,5-e]azepin-2-yl]-(4-fluoro-3-methoxy-phenyl)-amine |
| IV-85 | 4-[9-Chloro-7-(2-fluoro-phenyl)-5H-benzo[c]pyrimido[4,5-e]azepin-2-ylamino]-2-hydroxy-benzoic acid |
| IV-86 | 4-[9-Chloro-7-(2-chloro-phenyl)-5H-benzo[c]pyrimido[4,5-e]azepin-2-ylamino]-2-hydroxy-benzoic acid |
| IV-87 | [9-Chloro-7-(2-fluoro-phenyl)-5H-benzo[c]pyrimido[4,5-e]azepin-2-yl]-(3,4-dichloro-phenyl)-amine |
| IV-88 | [9-Chloro-7-(2-chloro-phenyl)-5H-benzo[c]pyrimido[4,5-e]azepin-2-yl]-(3,5-dimethoxy-phenyl)-amine |
| IV-89 | [9-Chloro-7-(2-fluoro-phenyl)-5H-benzo[c]pyrimido[4,5-e]azepin-2-yl]-(3,5-dimethyl-phenyl)-amine |
| IV-90 | [9-Chloro-7-(2-fluoro-phenyl)-5H-benzo[c]pyrimido[4,5-e]azepin-2-yl]-phenyl-amine |
| IV-91 | 4-[9-Chloro-7-(2,5-difluoro-phenyl)-5H-benzo[c]pyrimido[4,5-e]azepin-2-ylamino]-benzoic acid |
| IV-92 | 4-[9-Chloro-7-(2,3-difluoro-phenyl)-5H-benzo[c]pyrimido[4,5-e]azepin-2-ylamino]-benzoic acid |
| IV-93 | (3-Dimethylamino-pyrrolidin-1-yl)-{4-[7-(2-fluoro-phenyl)-9-methoxy-5H-benzo[c]pyrimido[4,5-e]azepin-2-ylamino]-phenyl}-methanone |
| IV-94 | 4-[9-Chloro-7-(2,5-dimethoxy-phenyl)-5H-benzo[c]pyrimido[4,5-e]azepin-2-ylamino]-benzoic acid |
| IV-95 | 4-[7-(2-Fluoro-phenyl)-9-methoxy-5H-benzo[c]pyrimido[4,5-e]azepin-2-ylamino]-N,N-bis-(2-hydroxy-ethyl)-benzamide |
| IV-96 | 4-[9-Chloro-7-(2,4-difluoro-phenyl)-5H-benzo[c]pyrimido[4,5-e]azepin-2-ylamino]-benzoic acid |
| IV-97 | 4-[9-Chloro-7-(2,4-difluoro-phenyl)-7H-benzo[c]pyrimido[4,5-e]azepin-2-ylamino]-benzoic acid |
| IV-98 | {4-[9-Chloro-7-(2-fluoro-phenyl)-5H-benzo[c]pyrimido[4,5-e]azepin-2-ylamino]-phenyl}-(3-dimethylamino-azetidin-1-yl)-methanone |
| IV-99 | 4-[9-Chloro-7-(2-fluoro-phenyl)-5H-benzo[c]pyrimido[4,5-e]azepin-2-ylamino]-N-methyl-N-(1-methyl-pyrrolidin-3-yl)-benzamide |
| IV-100 | {4-[9-Chloro-7-(2-fluoro-phenyl)-5H-benzo[c]pyrimido[4,5-e]azepin-2-ylamino]-phenyl}-(3-dimethylamino-pyrrolidin-1-yl)-methanone |
| IV-101 | 4-[9-Chloro-7-(2,4-dimethoxy-phenyl)-5H-benzo[c]pyrimido[4,5-e]azepin-2-ylamino]-benzoic acid |
| IV-102 | {4-[9-Chloro-7-(2-fluoro-phenyl)-5H-benzo[c]pyrimido[4,5-e]azepin-2-ylamino]-phenyl}-(3-methylamino-pyrrolidin-1-yl)-methanone |
| IV-103 | (3-Amino-pyrrolidin-1-yl)-{4-[9-chloro-7-(2-fluoro-phenyl)-5H-benzo[c]pyrimido[4,5-e]azepin-2-ylamino]-phenyl}-methanone |
| IV-104 | 4-[9-Chloro-7-(2,3-difluoro-phenyl)-5H-benzo[c]pyrimido[4,5-e]azepin-2-ylamino]-benzoic acid methyl ester |
| IV-105 | 4-[9-Chloro-7-(2,5-difluoro-phenyl)-5H-benzo[c]pyrimido[4,5-e]azepin-2-ylamino]-benzoic acid methyl ester |
| IV-106 | {4-[9-Chloro-7-(2-fluoro-phenyl)-5H-benzo[c]pyrimido[4,5-e]azepin-2-ylamino]-phenyl}-phosphonic acid |
| IV-107 | N-{4-[9-Chloro-7-(2-fluoro-phenyl)-5H-benzo[c]pyrimido[4,5-e]azepin-2-ylamino]-phenyl}-methanesulfonamide |
| IV-108 | N-{4-[9-Chloro-7-(2-fluoro-phenyl)-5H-benzo[c]pyrimido[4,5-e]azepin-2-ylamino]-phenyl}-N-methyl-acetamide |
| IV-109 | 2-{4-[9-Chloro-7-(2-fluoro-phenyl)-5H-benzo[c]pyrimido[4,5-e]azepin-2-ylamino]-benzoylamino}-succinic acid |
| IV-110 | [9-Chloro-7-(2-fluoro-phenyl)-4-methyl-5H-benzo[c]pyrimido[4,5-e]azepin-2-yl]-(3,4-dimethoxy-phenyl)-amine |
| IV-111 | {4-[9-Chloro-7-(2-fluoro-phenyl)-5H-benzo[c]pyrimido[4,5-e]azepin-2-ylamino]-phenyl}-(3,5-dimethyl-piperazin-1-yl)-methanone |
| IV-112 | 1-{4-[9-Chloro-7-(2-fluoro-phenyl)-5H-benzo[c]pyrimido[4,5-e]azepin-2-ylamino]-benzoyl}-pyrrolidine-2-carboxylic acid |
| IV-113 | {4-[9-Chloro-7-(2-fluoro-phenyl)-5H-benzo[c]pyrimido[4,5-e]azepin-2-ylamino]-phenyl}-(3-methyl-piperazin-1-yl)-methanone |
| IV-114 | [9-Chloro-7-(2-fluoro-phenyl)-5H-benzo[c]pyrimido[4,5-e]azepin-2-yl]-[4-(2H-tetrazol-5-yl)-phenyl]-amine |
| IV-115 | N-{4-[9-Chloro-7-(2-fluoro-phenyl)-5H-benzo[c]pyrimido[4,5-e]azepin-2-ylamino]-phenyl}-acetamide |
| IV-116 | 5-[9-Chloro-7-(2-fluoro-phenyl)-5H-benzo[c]pyrimido[4,5-e]azepin-2-ylamino]-2-fluoro-benzoic acid |
| IV-117 | N-(3-Amino-propyl)-4-[9-chloro-7-(2-fluoro-phenyl)-5H-benzo[c]pyrimido-[4,5-e]azepin-2-ylamino]-N-methyl-benzamide |

TABLE 2-continued

Examples of Compounds of Formula (IV)

| | |
|---|---|
| IV-118 | 2-{4-[9-Chloro-7-(2-fluoro-phenyl)-5H-benzo[c]pyrimido[4,5-e]azepin-2-ylamino]-benzoylamino}-propionic acid |
| IV-119 | 5-[9-Chloro-7-(2-fluoro-phenyl)-5H-benzo[c]pyrimido[4,5-e]azepin-2-ylamino]-pyridine-2-carboxylic acid |
| IV-120 | 2-{4-[9-Chloro-7-(2-fluoro-phenyl)-5H-benzo[c]pyrimido[4,5-e]azepin-2-ylamino]-phenyl}-N-(2-morpholin-4-yl-ethyl)-acetamide |
| IV-121 | 5-[9-Chloro-7-(2-fluoro-phenyl)-5H-benzo[c]pyrimido[4,5-e]azepin-2-ylamino]-2-methoxy-benzoic acid |
| IV-122 | 5-[9-Chloro-7-(2-fluoro-phenyl)-5H-benzo[c]pyrimido[4,5-e]azepin-2-ylamino]-2-methyl-benzoic acid |
| IV-123 | 6-[9-Chloro-7-(2-fluoro-phenyl)-5H-benzo[c]pyrimido[4,5-e]azepin-2-ylamino]-nicotinic acid |
| IV-124 | 4-[9-Chloro-7-(2-fluoro-phenyl)-5H-benzo[c]pyrimido[4,5-e]azepin-2-ylamino]-N-(2-morpholin-4-yl-ethyl)-benzenesulfonamide |
| IV-125 | 2-Chloro-5-[9-chloro-7-(2-fluoro-phenyl)-5H-benzo[c]pyrimido[4,5-e]azepin-2-ylamino]-benzoic acid |
| IV-126 | {4-[9-Chloro-7-(2-fluoro-phenyl)-5H-benzo[c]pyrimido[4,5-e]azepin-2-ylamino]-phenyl}-acetic acid |
| IV-127 | 4-[9-Chloro-7-(2-fluoro-phenyl)-5H-benzo[c]pyrimido[4,5-e]azepin-2-ylamino]-2-trifluoromethyl-benzoic acid |
| IV-128 | 4-[9-Chloro-7-(2-fluoro-phenyl)-5H-benzo[c]pyrimido[4,5-e]azepin-2-ylamino]-N-methyl-N-(1-methyl-piperidin-4-yl)-benzamide |
| IV-129 | N-(3-Amino-propyl)-4-[9-chloro-7-(2-fluoro-phenyl)-5H-benzo[c]pyrimido-[4,5-e]azepin-2-ylamino]-benzamide |
| IV-130 | 4-[9-Chloro-7-(2-fluoro-phenyl)-5H-benzo[c]pyrimido[4,5-e]azepin-2-ylamino]-N-(3-methylamino-propyl)-benzamide |
| IV-131 | N-(2-Amino-2-methyl-propyl)-4-[9-chloro-7-(2-fluoro-phenyl)-5H-benzo[c]pyrimido[4,5-e]azepin-2-ylamino]-benzamide |
| IV-132 | 2-(3,4-Dimethoxy-phenylamino)-7-(2-fluoro-phenyl)-5H-benzo[c]pyrimido-[4,5-e]azepine-10-carboxylic acid |
| IV-133 | 4-[9-Chloro-7-(2-fluoro-phenyl)-5H-benzo[c]pyrimido[4,5-e]azepin-2-ylamino]-2-methyl-benzoic acid |
| IV-134 | 2-Chloro-4-[9-chloro-7-(2-fluoro-phenyl)-5H-benzo[c]pyrimido[4,5-e]azepin-2-ylamino]-benzoic acid |
| IV-135 | 4-[9-Chloro-7-(2,6-difluoro-phenyl)-5H-benzo[c]pyrimido[4,5-e]azepin-2-ylamino]-benzoic acid |
| IV-136 | 4-[9-Chloro-7-(2-fluoro-phenyl)-5H-benzo[c]pyrimido[4,5-e]azepin-2-ylamino]-2-fluoro-benzoic acid |
| IV-137 | 4-[7-(2-Fluoro-phenyl)-9-methoxy-5H-benzo[c]pyrimido[4,5-e]azepin-2-ylamino]-benzoic acid |
| IV-138 | (3,4-Dimethoxy-phenyl)-[7-(2-fluoro-phenyl)-9-methoxy-5H-benzo[c]pyrimido-[4,5-e]azepin-2-yl]-amine |
| IV-139 | [9,10-Dichloro-7-(2-fluoro-phenyl)-5H-benzo[c]pyrimido[4,5-e]azepin-2-yl]-(3,4-dimethoxy-phenyl)-amine |
| IV-140 | 4-[9,10-Dichloro-7-(2-fluoro-phenyl)-5H-benzo[c]pyrimido[4,5-e]azepin-2-ylamino]-benzoic acid |
| IV-141 | 4-[9-Chloro-7-(2-fluoro-phenyl)-5H-benzo[c]pyrimido[4,5-e]azepin-2-ylamino]-2-methoxy-benzoic acid |
| IV-142 | N-(2-Amino-ethyl)-4-[9-chloro-7-(2-fluoro-phenyl)-5H-benzo[c]pyrimido-[4,5-e]azepin-2-ylamino]-benzamide |
| IV-143 | 4-(9-Chloro-7-phenyl-5H-benzo[c]pyrimido[4,5-e]azepin-2-ylamino)-benzoic acid |
| IV-144 | [7-(2-Bromo-phenyl)-9-chloro-5H-benzo[c]pyrimido[4,5-e]azepin-2-yl]-(3,4-dimethoxy-phenyl)-amine |
| IV-145 | 2-{4-[9-Chloro-7-(2-fluoro-phenyl)-5H-benzo[c]pyrimido[4,5-e]azepin-2-ylamino]-phenyl}-1-(4-methyl-piperazin-1-yl)-ethanone |
| IV-146 | 3-[9-Chloro-7-(2-fluoro-phenyl)-5H-benzo[c]pyrimido[4,5-e]azepin-2-ylamino]-benzoic acid |
| IV-147 | 4-[9-Chloro-7-(2-fluoro-phenyl)-5H-benzo[c]pyrimido[4,5-e]azepin-2-ylamino]-N-[2-(1H-imidazol-4-yl)-ethyl]-benzamide |
| IV-148 | 4-[7-(2-Fluoro-phenyl)-9-methyl-5H-benzo[c]pyrimido[4,5-e]azepin-2-ylamino]-N-(2-morpholin-4-yl-ethyl)-benzamide |
| IV-149 | {3-[9-Chloro-7-(2-fluoro-phenyl)-5H-benzo[c]pyrimido[4,5-e]azepin-2-ylamino]-phenyl}-acetic acid |
| IV-150 | 4-[9-Chloro-7-(2-fluoro-phenyl)-5H-benzo[c]pyrimido[4,5-e]azepin-2-ylamino]-N-(2-pyridin-4-yl-ethyl)-benzamide |
| IV-151 | 4-[9-Chloro-7-(2-fluoro-phenyl)-5H-benzo[c]pyrimido[4,5-e]azepin-2-ylamino]-N-(2-pyridin-3-yl-ethyl)-benzamide |
| IV-152 | (9-Chloro-7-phenyl-5H-benzo[c]pyrimido[4,5-e]azepin-2-yl)-(3,4-dimethoxy-phenyl)-amine |
| IV-153 | 4-[7-(2-Fluoro-phenyl)-10-methyl-5H-benzo[c]pyrimido[4,5-e]azepin-2-ylamino]-benzoic acid |
| IV-154 | (3,4-Dimethoxy-phenyl)-[7-(2-fluoro-phenyl)-5H-benzo[c]pyrimido-[4,5-e]azepin-2-yl]-amine |
| IV-155 | 4-[9-Chloro-7-(4-methoxy-phenyl)-5H-benzo[c]pyrimido[4,5-e]azepin-2-ylamino]-benzoic acid |
| IV-156 | 4-[9-Chloro-7-(3-methoxy-phenyl)-5H-benzo[c]pyrimido[4,5-e]azepin-2-ylamino]-benzoic acid |

TABLE 2-continued

Examples of Compounds of Formula (IV)

| | |
|---|---|
| IV-157 | 4-[9-Chloro-7-(3-fluoro-phenyl)-5H-benzo[c]pyrimido[4,5-e]azepin-2-ylamino]-N-[3-(4-methyl-piperazin-1-yl)-propyl]-benzamide |
| IV-158 | 4-[9-Chloro-7-(3-fluoro-phenyl)-5H-benzo[c]pyrimido[4,5-e]azepin-2-ylamino]-N-(2-morpholin-4-yl-ethyl)-benzamide |
| IV-159 | {4-[9-Chloro-7-(3-fluoro-phenyl)-5H-benzo[c]pyrimido[4,5-e]azepin-2-ylamino]-phenyl}-(4-methyl-piperazin-1-yl)-methanone |
| IV-160 | 4-[9-Chloro-7-(2-fluoro-phenyl)-5H-benzo[c]pyrimido[4,5-e]azepin-2-ylamino]-N-methyl-N-(2-pyridin-2-yl-ethyl)-benzamide |
| IV-161 | 4-[9-Chloro-7-(2-fluoro-phenyl)-5H-benzo[c]pyrimido[4,5-e]azepin-2-ylamino]-N-(2-pyridin-2-yl-ethyl)-benzamide |
| IV-162 | 4-[9-Chloro-7-(3-fluoro-phenyl)-5H-benzo[c]pyrimido[4,5-e]azepin-2-ylamino]-benzoic acid |
| IV-163 | {3-[9-Chloro-7-(2-fluoro-phenyl)-5H-benzo[c]pyrimido[4,5-e]azepin-2-ylamino]-phenyl}-(4-methyl-piperazin-1-yl)-methanone |
| IV-164 | 9-Chloro-7-(2-fluorophenyl)-N-{4-[(4-pyridin-2-ylpiperazin-1-yl)carbonyl]phenyl}-5H-pyrimido[5,4-d][2]benzazepin-2-amine |
| IV-165 | 9-Chloro-7-(2-fluorophenyl)-N-(4-{[4-(2-morpholin-4-yl-2-oxoethyl)piperazin-1-yl]carbonyl}phenyl)-5H-pyrimido[5,4-d][2]benzazepin-2-amine |
| IV-166 | 9-Chloro-7-(2-fluorophenyl)-N-(4-{[4-(2-furoyl)piperazin-1-yl]carbonyl}phenyl)-5H-pyrimido[5,4-d][2]benzazepin-2-amine |
| IV-167 | Benzyl-4-(4-{[9-chloro-7-(2-fluorophenyl)-5H-pyrimido[5,4-d][2]benzazepin-2-yl]amino}benzoyl)piperazine-1-carboxylate |
| IV-168 | Ethyl-4-(4-{[9-chloro-7-(2-fluorophenyl)-5H-pyrimido[5,4-d][2]benzazepin-2-yl]amino}benzoyl)piperazine-1-carboxylate |
| IV-169 | 2-[4-(4-{[9-Chloro-7-(2-fluorophenyl)-5H-pyrimido[5,4-d][2]benzazepin-2-yl]amino}benzoyl)piperazin-1-yl]benzoic acid |
| IV-170 | 2-[4-(4-{[9-Chloro-7-(2-fluorophenyl)-5H-pyrimido[5,4-d][2]benzazepin-2-yl]amino}benzoyl)piperazin-1-yl]-N-isopropylacetamide |
| IV-171 | 9-Chloro-7-(2-fluorophenyl)-N-(4-{[4-(2-pyrrolidin-1-ylethyl)piperazin-1-yl]carbonyl}phenyl)-5H-pyrimido[5,4-d][2]benzazepin-2-amine |
| IV-172 | N-[2-(aminocarbonyl)phenyl]-4-{[9-chloro-7-(2-fluorophenyl)-5H-pyrimido-[5,4-d][2]benzazepin-2-yl]amino}benzamide |
| IV-173 | 9-Chloro-7-(2-fluorophenyl)-N-{4-[(4-pyrimidin-2-ylpiperazin-1-yl)carbonyl]phenyl}-5H-pyrimido[5,4-d][2]benzazepin-2-amine |
| IV-174 | 4-{[9-Chloro-7-(2-chloro-6-fluorophenyl)-5H-pyrimido[5,4-d][2]benzazepin-2-yl]amino}benzoic acid |
| IV-175 | 9-Chloro-7-(2,6-difluorophenyl)-N-{4-[(3,5-dimethylpiperazin-1-yl)carbonyl]phenyl}-5H-pyrimido[5,4-d][2]benzazepin-2-amine |
| IV-176 | 9-Chloro-7-(2,6-difluorophenyl)-N-(4-{[3-(dimethylamino)pyrrolidin-1-yl]carbonyl}phenyl)-5H-pyrimido[5,4-d][2]benzazepin-2-amine |
| IV-177 | 9-Chloro-N-{4-[(3,5-dimethylpiperazin-1-yl)carbonyl]phenyl}-7-(2-fluoro-6-methoxyphenyl)-5H-pyrimido[5,4-d][2]benzazepin-2-amine |
| IV-178 | 9-Chloro-N-(4-{[3-(dimethylamino)pyrrolidin-1-yl]carbonyl}phenyl)-7-(2-fluoro-6-methoxyphenyl)-5H-pyrimido[5,4-d][2]benzazepin-2-amine |
| IV-179 | 9-Chloro-N-(4-{[3-(dimethylamino)azetidin-1-yl]carbonyl}phenyl)-7-(2-fluoro-6-methoxyphenyl)-5H-pyrimido[5,4-d][2]benzazepin-2-amine |
| IV-180 | 9-Chloro-7-(2,6-difluorophenyl)-N-(4-{[3-(dimethylamino)azetidin-1-yl]carbonyl}phenyl)-5H-pyrimido[5,4-d][2]benzazepin-2-amine |
| IV-181 | {4-[9-Chloro-7-(2-fluoro-phenyl)-5H-benzo[c]pyrimido[4,5-e]azepin-2-ylamino]-phenyl}-[4-(3-piperidin-1-yl-propyl)-piperazin-1-yl]-methanone |
| IV-182 | {4-[9-Chloro-7-(2-fluoro-phenyl)-5H-benzo[c]pyrimido[4,5-e]azepin-2-ylamino]-phenyl}-[4-(2-piperidin-1-yl-ethyl)-piperazin-1-yl]-methanone |
| IV-183 | {4-[9-Chloro-7-(2,6-difluoro-phenyl)-5H-benzo[c]pyrimido[4,5-e]azepin-2-ylamino]-phenyl}-(4-dimethylamino-piperidin-1-yl)-methanone |
| IV-184 | {4-[9-Chloro-7-(2,6-difluoro-phenyl)-5H-benzo[c]pyrimido[4,5-e]azepin-2-ylamino]-phenyl}-(4-methyl-piperazin-1-yl)-methanone |
| IV-185 | 4-[9-Chloro-7-(2,6-difluoro-phenyl)-5H-benzo[c]pyrimido[4,5-e]azepin-2-ylamino]-N-(3-dimethylamino-propyl)-N-methyl-benzamide |
| IV-186 | {4-[9-Chloro-7-(2-fluoro-6-methoxy-phenyl)-5H-benzo[c]pyrimido-[4,5-e]azepin-2-ylamino]-phenyl}-(4-dimethylamino-piperidin-1-yl)-methanone |
| IV-187 | {4-[9-Chloro-7-(2-fluoro-phenyl)-5H-benzo[c]pyrimido[4,5-e]azepin-2-ylamino]-phenyl}-[4-(2-dipropylamino-ethyl)-piperazin-1-yl]-methanone |
| IV-188 | {4-[9-Chloro-7-(2-fluoro-phenyl)-5H-benzo[c]pyrimido[4,5-e]azepin-2-ylamino]-phenyl}-[4-(3-pyrrolidin-1-yl-propyl)-piperazin-1-yl]-methanone |
| IV-189 | {4-[9-Chloro-7-(2-fluoro-phenyl)-5H-benzo[c]pyrimido[4,5-e]azepin-2-ylamino]-phenyl}-[4-(2-morpholin-4-yl-ethyl)-piperazin-1-yl]-methanone |
| IV-190 | 4-[9-Chloro-7-(2-fluoro-6-methoxy-phenyl)-5H-benzo[c]pyrimido[4,5-e]azepin-2-ylamino]-benzoic acid |
| IV-191 | {4-[9-Chloro-7-(2,6-difluoro-phenyl)-5H-benzo[c]pyrimido[4,5-e]azepin-2-ylamino]-phenyl}-(3(S)-methyl-piperazin-1-yl)-methanone |
| IV-192 | (3-Amino-azetidin-1-yl)-{4-[9-chloro-7-(2-fluoro-phenyl)-5H-benzo[c]pyrimido[4,5-e]azepin-2-ylamino]-phenyl}-methanone |
| IV-193 | {4-[9-Chloro-7-(2-fluoro-phenyl)-5H-benzo[c]pyrimido[4,5-e]azepin-2-ylamino]-phenyl}-(3-dimethylaminomethyl-azetidin-1-yl)-methanone |
| IV-194 | {4-[9-Chloro-7-(2,6-difluoro-phenyl)-5H-benzo[c]pyrimido[4,5-e]azepin-2-ylamino]-phenyl}-(3(R)-methyl-piperazin-1-yl)-methanone |
| IV-195 | {4-[9-Chloro-7-(2,6-difluoro-phenyl)-5H-benzo[c]pyrimido[4,5-e]azepin-2-ylamino]-phenyl}-piperazin-1-yl-methanone |

TABLE 2-continued

Examples of Compounds of Formula (IV)

| | |
|---|---|
| IV-196 | (3-Amino-pyrrolidin-1-yl)-{4-[9-chloro-7-(2,6-difluoro-phenyl)-5H-benzo[c]pyrimido[4,5-e]azepin-2-ylamino]-phenyl}-methanone |
| IV-197 | {4-[9-Chloro-7-(2,6-difluoro-phenyl)-5H-benzo[c]pyrimido[4,5-e]azepin-2-ylamino]-phenyl}-(3-methylamino-pyrrolidin-1-yl)-methanone |
| IV-198 | 4-[9-Chloro-7-(2,6-difluoro-phenyl)-5H-benzo[c]pyrimido[4,5-e]azepin-2-ylamino]-N-methyl-N-(3-methylamino-propyl)-benzamide |
| IV-199 | {4-[9-Chloro-7-(2-fluoro-6-methoxy-phenyl)-5H-benzo[c]pyrimido[4,5-e]azepin-2-ylamino]-phenyl}-(3-methylamino-pyrrolidin-1-yl)-methanone |
| IV-200 | 4-[9-Chloro-7-(2-fluoro-phenyl)-5H-benzo[c]pyrimido[4,5-e]azepin-2-ylamino]-cyclohexanecarboxylic acid |
| IV-201 | 9-chloro-N-(4-{[4-(2-ethoxyphenyl)piperazin-1-yl]carbonyl}phenyl)-7-(2-fluorophenyl)-5H-pyrimido[5,4-d][2]benzazepin-2-amine |
| IV-202 | N-[amino(imino)methyl]-4-{[9-chloro-7-(2,6-difluorophenyl)-5H-pyrimido[5,4-d][2]benzazepin-2-yl]amino}benzamide |
| IV-203 | 3-{[9-chloro-7-(2,6-difluorophenyl)-5H-pyrimido[5,4-d][2]benzazepin-2-yl]amino}benzoic acid |
| IV-204 | 9-chloro-7-(2,6-difluorophenyl)-N-(3-{[3-(dimethylamino)azetidin-1-yl]carbonyl}phenyl)-5H-pyrimido[5,4-d][2]benzazepin-2-amine |
| IV-205 | 9-chloro-7-(2,6-difluorophenyl)-N-(3-{[4-(dimethylamino)piperidin-1-yl]carbonyl}phenyl)-5H-pyrimido[5,4-d][2]benzazepin-2-amine |
| IV-206 | 9-chloro-7-(2,6-difluorophenyl)-N-(3-{[3-(dimethylamino)pyrrolidin-1-yl]carbonyl}phenyl)-5H-pyrimido[5,4-d][2]benzazepin-2-amine |
| IV-207 | N-[2-(aminomethyl)-1,3-benzoxazol-5-yl]-9-chloro-7-(2,6-difluorophenyl)-5H-pyrimido[5,4-d][2]benzazepin-2-amine |
| IV-208 | 9-chloro-N-[4-({4-[3-(diethylamino)propyl]piperazin-1-yl}carbonyl)phenyl]-7-(2-fluorophenyl)-5H-pyrimido[5,4-d][2]benzazepin-2-amine |
| IV-209 | 9-chloro-N-[4-({4-[2-(diethylamino)ethyl]piperazin-1-yl}carbonyl)phenyl]-7-(2-fluorophenyl)-5H-pyrimido[5,4-d][2]benzazepin-2-amine |
| IV-210 | 9-chloro-N-[4-({4-[3-(dimethylamino)propyl]piperazin-1-yl}carbonyl)phenyl]-7-(2-fluorophenyl)-5H-pyrimido[5,4-d][2]benzazepin-2-amine |
| IV-211 | 9-chloro-7-(2-fluorophenyl)-N-[4-({4-[(1-methylpiperidin-3-yl)methyl]piperazin-1-yl}carbonyl)phenyl]-5H-pyrimido[5,4-d][2]benzazepin-2-amine |
| IV-212 | 9-chloro-7-(2,6-difluorophenyl)-N-(4-nitrophenyl)-5H-pyrimido[5,4-d][2]benzazepin-2-amine |
| IV-213 | 9-chloro-N-(3-chloro-4-{[4-(2-pyrrolidin-1-ylethyl)piperazin-1-yl]carbonyl}phenyl)-7-(2-fluorophenyl)-5H-pyrimido[5,4-d][2]benzazepin-2-amine |
| IV-214 | 9-chloro-N-{3-chloro-4-[(3-methylpiperazin-1-yl)carbonyl]phenyl}-7-(2-fluorophenyl)-5H-pyrimido[5,4-d][2]benzazepin-2-amine |
| IV-215 | 9-chloro-N-(3-chloro-4-{[3-(dimethylamino)pyrrolidin-1-yl]carbonyl}phenyl)-7-(2,6-difluorophenyl)-5H-pyrimido[5,4-d][2]benzazepin-2-amine |
| IV-216 | 9-chloro-N-{3-chloro-4-[(3-methylpiperazin-1-yl)carbonyl]phenyl}-7-(2,6-difluorophenyl)-5H-pyrimido[5,4-d][2]benzazepin-2-amine |
| IV-217 | N-[9-chloro-7-(2,6-difluorophenyl)-5H-pyrimido[5,4-d][2]benzazepin-2-yl]benzene-1,4-diamine |
| IV-218 | methyl 2-chloro-4-{[9-chloro-7-(2,6-difluorophenyl)-5H-pyrimido[5,4-d][2]benzazepin-2-yl]amino}benzoate |
| IV-219 | 1-(4-{[9-chloro-7-(2,6-difluorophenyl)-5H-pyrimido[5,4-d][2]benzazepin-2-yl]amino}benzoyl)piperazine-2-carboxylic acid |
| IV-220 | 9-chloro-7-(2,6-difluorophenyl)-N-(4-{[4-(methylamino)piperidin-1-yl]carbonyl}phenyl)-5H-pyrimido[5,4-d][2]benzazepin-2-amine |
| IV-221 | N-{4-[(3-aminopiperidin-1-yl)carbonyl]phenyl}-9-chloro-7-(2,6-difluorophenyl)-5H-pyrimido[5,4-d][2]benzazepin-2-amine |
| IV-222 | 9-chloro-7-(2,6-difluorophenyl)-N-{3-[(3,5-dimethylpiperazin-1-yl)carbonyl]phenyl}-5H-pyrimido[5,4-d][2]benzazepin-2-amine |
| IV-223 | 4-{[9-chloro-7-(2,6-difluorophenyl)-5H-pyrimido[5,4-d][2]benzazepin-2-yl]amino}-N-[[4-(dimethylamino)piperidin-1-yl](imino)methyl]benzamide |
| IV-224 | 4-{[9-chloro-7-(2,6-difluorophenyl)-5H-pyrimido[5,4-d][2]benzazepin-2-yl]amino}-N-[imino(piperazin-1-yl)methyl]benzamide |
| IV-225 | 4-{[9-chloro-7-(2-fluoro-6-methoxyphenyl)-5H-pyrimido[5,4-d][2]benzazepin-2-yl]amino}-N-[3-(dimethylamino)propyl]-N-methylbenzamide |
| IV-226 | 3-{[9-chloro-7-(2-fluoro-6-methoxyphenyl)-5H-pyrimido[5,4-d][2]benzazepin-2-yl]amino}-N-[3-(dimethylamino)propyl]-N-methylbenzamide |
| IV-227 | 9-chloro-N-(3-{[3-(dimethylamino)azetidin-1-yl]carbonyl}phenyl)-7-(2-fluoro-6-methoxyphenyl)-5H-pyrimido[5,4-d][2]benzazepin-2-amine |
| IV-228 | 9-chloro-N-{3-[(3,5-dimethylpiperazin-1-yl)carbonyl]phenyl}-7-(2-fluoro-6-methoxyphenyl)-5H-pyrimido[5,4-d][2]benzazepin-2-amine |
| IV-229 | 9-chloro-N-(3-{[4-(dimethylamino)piperidin-1-yl]carbonyl}phenyl)-7-(2-fluoro-6-methoxyphenyl)-5H-pyrimido[5,4-d][2]benzazepin-2-amine |
| IV-230 | N-(4-{[3-(aminomethyl)azetidin-1-yl]carbonyl}phenyl)-9-chloro-7-(2-fluorophenyl)-5H-pyrimido[5,4-d][2]benzazepin-2-amine |
| IV-231 | 9-chloro-N-(3-{[3-(dimethylamino)pyrrolidin-1-yl]carbonyl}phenyl)-7-(2-fluoro-6-methoxyphenyl)-5H-pyrimido[5,4-d][2]benzazepin-2-amine |
| IV-232 | 9-chloro-7-(2-fluoro-6-methoxyphenyl)-N-{4-[(3-methylpiperazin-1-yl)carbonyl]phenyl}-5H-pyrimido[5,4-d][2]benzazepin-2-amine |
| IV-233 | 9-chloro-7-(2-fluoro-6-methoxyphenyl)-N-{4-[(4-methylpiperazin-1-yl)carbonyl]phenyl}-5H-pyrimido[5,4-d][2]benzazepin-2-amine |

TABLE 2-continued

Examples of Compounds of Formula (IV)

| | |
|---|---|
| IV-234 | 9-chloro-7-(2,6-difluorophenyl)-N-(4-{[3-(methylamino)azetidin-1-yl]carbonyl}phenyl)-5H-pyrimido[5,4-d][2]benzazepin-2-amine |
| IV-235 | 9-chloro-7-(2-fluoro-6-methoxyphenyl)-N-(4-{[3-(methylamino)azetidin-1-yl]carbonyl}phenyl)-5H-pyrimido[5,4-d][2]benzazepin-2-amine |
| IV-236 | 4-{[9-chloro-7-(2,6-difluorophenyl)-5H-pyrimido[5,4-d][2]benzazepin-2-yl]amino}benzonitrile |
| IV-237 | 4-{[9-chloro-7-(2,6-difluorophenyl)-5H-pyrimido[5,4-d][2]benzazepin-2-yl]amino}-N-[[3-(dimethylamino)pyrrolidin-1-yl](imino)methyl]benzamide |
| IV-238 | 4-{[9-chloro-7-(2,6-difluorophenyl)-5H-pyrimido[5,4-d][2]benzazepin-2-yl]amino}-N-[(3,5-dimethylpiperazin-1-yl)(imino)methyl]benzamide |
| IV-239 | N-{4-[(4-aminopiperidin-1-yl)carbonyl]phenyl}-9-chloro-7-(2,6-difluorophenyl)-5H-pyrimido[5,4-d][2]benzazepin-2-amine |
| IV-240 | N-{4-[(3-aminopyrrolidin-1-yl)carbonyl]phenyl}-9-chloro-7-(2-fluoro-6-methoxyphenyl)-5H-pyrimido[5,4-d][2]benzazepin-2-amine |
| IV-241 | N-{4-[(4-aminopiperidin-1-yl)carbonyl]phenyl}-9-chloro-7-(2-fluoro-6-methoxyphenyl)-5H-pyrimido[5,4-d][2]benzazepin-2-amine |
| IV-242 | 9-chloro-7-(2-fluoro-6-methoxyphenyl)-N-(4-{[4-(methylamino)piperidin-1-yl]carbonyl}phenyl)-5H-pyrimido[5,4-d][2]benzazepin-2-amine |
| IV-243 | 9-chloro-7-(2-fluoro-6-methoxyphenyl)-N-[4-(piperazin-1-ylcarbonyl)phenyl]-5H-pyrimido[5,4-d][2]benzazepin-2-amine |
| IV-244 | 9-chloro-7-(2,6-difluorophenyl)-N-{4-[[4-(dimethylamino)piperidin-1-yl](imino)methyl]phenyl}-5H-pyrimido[5,4-d][2]benzazepin-2-amine |
| IV-245 | N-(4-{[9-chloro-7-(2,6-difluorophenyl)-5H-pyrimido[5,4-d][2]benzazepin-2-yl]amino}phenyl)guanidine |
| IV-246 | 4-{[9-chloro-7-(2,6-difluorophenyl)-5H-pyrimido[5,4-d][2]benzazepin-2-yl]amino}-N-methyl-N-[2-(methylamino)ethyl]benzamide |
| IV-247 | 4-{[9-chloro-7-(2,6-difluorophenyl)-5H-pyrimido[5,4-d][2]benzazepin-2-yl]amino}-N-[2-(dimethylamino)ethyl]-N-methylbenzamide |
| IV-248 | methyl 4-(4-{[9-chloro-7-(2,6-difluorophenyl)-5H-pyrimido[5,4-d][2]benzazepin-2-yl]amino}benzoyl)piperazine-2-carboxylate |
| IV-249 | 2-[(4-carboxyphenyl)amino]-7-(2-fluorophenyl)-5H-pyrimido[5,4-d][2]benzazepine-9-carboxylic acid |
| IV-250 | 9-chloro-7-(2,6-difluorophenyl)-N-{4-[[3-(dimethylamino)pyrrolidin-1-yl](imino)methyl]phenyl}-5H-pyrimido[5,4-d][2]benzazepin-2-amine |
| IV-251 | 9-chloro-7-(2,6-difluorophenyl)-N-(4-[(3,5-dimethylpiperazin-1-yl)(imino)methyl]phenyl}-5H-pyrimido[5,4-d][2]benzazepin-2-amine |
| IV-252 | N-(2-aminoethyl)-4-{[9-chloro-7-(2,6-difluorophenyl)-5H-pyrimido[5,4-d][2]benzazepin-2-yl]amino}-N-methylbenzamide |
| IV-253 | 9-chloro-7-(2,6-difluorophenyl)-N-(4-{[3-(methylamino)piperidin-1-yl]carbonyl}phenyl)-5H-pyrimido[5,4-d][2]benzazepin-2-amine |
| IV-254 | 4-{[9-chloro-7-(2-fluoro-6-methoxyphenyl)-5H-pyrimido[5,4-d][2]benzazepin-2-yl]amino}-N-methyl-N-[2-(methylamino)ethyl]benzamide |
| IV-255 | 4-{[9-chloro-7-(2-fluoro-6-methoxyphenyl)-5H-pyrimido[5,4-d][2]benzazepin-2-yl]amino}-N-[2-(dimethylamino)ethyl]-N-methylbenzamide |
| IV-256 | 7-(2-fluorophenyl)-2-[(3-methoxyphenyl)amino]-5H-pyrimido[5,4-d][2]benzazepine-9-carboxylic acid |
| IV-257 | N-(3-aminopropyl)-4-{[9-chloro-7-(2,6-difluorophenyl)-5H-pyrimido[5,4-d][2]benzazepin-2-yl]amino}-N-methylbenzamide |
| IV-258 | 2-chloro-5-{[9-chloro-7-(2,6-difluorophenyl)-5H-pyrimido[5,4-d][2]benzazepin-2-yl]amino}benzoic acid |
| IV-259 | 4-{[9-chloro-7-(2,6-difluorophenyl)-5H-pyrimido[5,4-d][2]benzazepin-2-yl]amino}-N-[[3-(dimethylamino)azetidin-1-yl](imino)methyl]benzamide |
| IV-260 | N-(2-amino-2-methylpropyl)-4-{[9-chloro-7-(2,6-difluorophenyl)-5H-pyrimido[5,4-d][2]benzazepin-2-yl]amino}benzamide |
| IV-261 | 4-{[9-chloro-7-(2-fluoro-6-methoxyphenyl)-5H-pyrimido[5,4-d][2]benzazepin-2-yl]amino}-N-methyl-N-[3-(methylamino)propyl]benzamide |
| IV-262 | N-{4-[(3-aminopiperidin-1-yl)carbonyl]phenyl}-9-chloro-7-(2-fluoro-6-methoxyphenyl)-5H-pyrimido[5,4-d][2]benzazepin-2-amine |
| IV-263 | 9-chloro-7-(2-fluoro-6-methoxyphenyl)-N-(4-{[3-(methylamino)piperidin-1-yl]carbonyl}phenyl)-5H-pyrimido[5,4-d][2]benzazepin-2-amine |
| IV-264 | N-(3-aminopropyl)-4-{[9-chloro-7-(2-fluoro-6-methoxyphenyl)-5H-pyrimido[5,4-d][2]benzazepin-2-yl]amino}-N-methylbenzamide |
| IV-265 | N-(2-aminoethyl)-4-{[9-chloro-7-(2-fluoro-6-methoxyphenyl)-5H-pyrimido[5,4-d][2]benzazepin-2-yl]amino}-N-methylbenzamide |
| IV-266 | 4-(4-{[9-chloro-7-(2,6-difluorophenyl)-5H-pyrimido[5,4-d][2]benzazepin-2-yl]amino}benzoyl)piperazine-2-carboxylic acid |
| IV-267 | 9-chloro-7-(2,6-difluorophenyl)-N-{4-[[3-(dimethylamino)azetidin-1-yl](imino)methyl]phenyl}-5H-pyrimido[5,4-d][2]benzazepin-2-amine |
| IV-268 | 9-chloro-7-(2,6-difluorophenyl)-N-(4-{imino[3-(methylamino)pyrrolidin-1-yl]methyl}phenyl)-5H-pyrimido[5,4-d][2]benzazepin-2-amine |
| IV-269 | 9-chloro-N-(4-chloro-3-{[4-(dimethylamino)piperidin-1-yl]carbonyl}phenyl)-7-(2,6-difluorophenyl)-5H-pyrimido[5,4-d][2]benzazepin-2-amine |
| IV-270 | 9-chloro-7-(2,6-difluorophenyl)-N-[4-(5,5-dimethyl-4,5-dihydro-1H-imidazol-2-yl)phenyl]-5H-pyrimido[5,4-d][2]benzazepin-2-amine |
| IV-271 | N-[9-chloro-7-(2,6-difluorophenyl)-5H-pyrimido[5,4-d][2]benzazepin-2-yl]-N'-pyrimidin-2-ylbenzene-1,4-diamine |
| IV-272 | 4-{[9-(3-aminoprop-1-yn-1-yl)-7-(2,6-difluorophenyl)-5H-pyrimido[5,4-d][2]benzazepin-2-yl]amino}benzoic acid |

TABLE 2-continued

Examples of Compounds of Formula (IV)

| | |
|---|---|
| IV-273 | 9-bromo-7-(2,6-difluorophenyl)-N-(3-methoxyphenyl)-5H-pyrimido[5,4-d][2]benzazepin-2-amine |
| IV-274 | 4-{[9-bromo-7-(2,6-difluorophenyl)-5H-pyrimido[5,4-d][2]benzazepin-2-yl]amino}benzoic acid |
| IV-275 | 7-(2,6-difluorophenyl)-N-(3-methoxyphenyl)-9-(3-pyrrolidin-1-ylprop-1-yn-1-yl)-5H-pyrimido[5,4-d][2]benzazepin-2-amine |
| IV-276 | 9-(3-aminoprop-1-yn-1-yl)-7-(2,6-difluorophenyl)-N-(3-methoxyphenyl)-5H-pyrimido[5,4-d][2]benzazepin-2-amine |
| IV-277 | 4-({9-chloro-7-[2-(trifluoromethyl)phenyl]-5H-pyrimido[5,4-d][2]benzazepin-2-yl}amino)benzoic acid |
| IV-278 | N-{4-[(3-aminoazetidin-1-yl)carbonyl]phenyl}-9-chloro-7-(2,6-difluorophenyl)-5H-pyrimido[5,4-d][2]benzazepin-2-amine |
| IV-279 | 4-[(9-chloro-7-pyridin-2-yl-5H-pyrimido[5,4-d][2]benzazepin-2-yl)amino]benzoic acid |
| IV-280 | N-(4-{[9-chloro-7-(2,6-difluorophenyl)-5H-pyrimido[5,4-d][2]benzazepin-2-yl]amino}phenyl)-4-methylpiperazine-1-carboxamide |
| IV-281 | 9-chloro-N-(4-chloro-3-{[3-(methylamino)pyrrolidin-1-yl]carbonyl}phenyl)-7-(2,6-difluorophenyl)-5H-pyrimido[5,4-d][2]benzazepin-2-amine |
| IV-282 | 9-chloro-N-(4-chloro-3-{[4-(methylamino)piperidin-1-yl]carbonyl}phenyl)-7-(2,6-difluorophenyl)-5H-pyrimido[5,4-d][2]benzazepin-2-amine |
| IV-283 | 2-chloro-5-{[9-chloro-7-(2,6-difluorophenyl)-5H-pyrimido[5,4-d][2]benzazepin-2-yl]amino}-N-methyl-N-[2-(methylamino)ethyl]benzamide |
| IV-284 | N-{4-[(3-aminopyrrolidin-1-yl)(imino)methyl]phenyl}-9-chloro-7-(2,6-difluorophenyl)-5H-pyrimido[5,4-d][2]benzazepin-2-amine |
| IV-285 | 2-(4-{[9-chloro-7-(2,6-difluorophenyl)-5H-pyrimido[5,4-d][2]benzazepin-2-yl]amino}phenyl)-1,4,5,6-tetrahydropyrimidin-5-ol |
| IV-286 | N-{4-[(3-aminoazetidin-1-yl)carbonyl]phenyl}-9-chloro-7-(2-fluoro-6-methoxyphenyl)-5H-pyrimido[5,4-d][2]benzazepin-2-amine |
| IV-287 | N-{4-[(4-aminopiperidin-1-yl)carbonyl]phenyl}-9-chloro-7-[2-(trifluoromethyl)phenyl]-5H-pyrimido[5,4-d][2]benzazepin-2-amine |
| IV-288 | 9-chloro-N-(4-{[4-(methylamino)piperidin-1-yl]carbonyl}phenyl)-7-[2-(trifluoromethyl)phenyl]-5H-pyrimido[5,4-d][2]benzazepin-2-amine |
| IV-289 | N-{4-[(3-aminopyrrolidin-1-yl)carbonyl]phenyl}-9-chloro-7-[2-(trifluoromethyl)phenyl]-5H-pyrimido[5,4-d][2]benzazepin-2-amine |
| IV-290 | 9-chloro-N-(4-{[3-(methylamino)pyrrolidin-1-yl]carbonyl}phenyl)-7-[2-(trifluoromethyl)phenyl]-5H-pyrimido[5,4-d][2]benzazepin-2-amine |
| IV-291 | 9-chloro-N-(4-chloro-3-{[3-(methylamino)azetidin-1-yl]carbonyl}phenyl)-7-(2,6-difluorophenyl)-5H-pyrimido[5,4-d][2]benzazepin-2-amine |
| IV-292 | N-{3-[(4-aminopiperidin-1-yl)carbonyl]-4-chlorophenyl}-9-chloro-7-(2,6-difluorophenyl)-5H-pyrimido[5,4-d][2]benzazepin-2-amine |
| IV-293 | 9-chloro-7-(2,6-difluorophenyl)-N-(4-{[3-(dimethylamino)piperidin-1-yl]carbonyl}phenyl)-5H-pyrimido[5,4-d][2]benzazepin-2-amine |
| IV-294 | methyl 4-amino-1-(4-{[9-chloro-7-(2,6-difluorophenyl)-5H-pyrimido[5,4-d][2]benzazepin-2-yl]amino}benzoyl)piperidine-4-carboxylate |
| IV-295 | 4-amino-1-(4-{[9-chloro-7-(2,6-difluorophenyl)-5H-pyrimido[5,4-d][2]benzazepin-2-yl]amino}benzoyl)piperidine-4-carboxylic acid |
| IV-296 | N-{4-[(3-aminoazetidin-1-yl)carbonyl]phenyl}-9-chloro-7-[2-(trifluoromethyl)phenyl]-5H-pyrimido[5,4-d][2]benzazepin-2-amine |
| IV-297 | 9-chloro-N-(4-{[3-(methylamino)azetidin-1-yl]carbonyl}phenyl)-7-[2-(trifluoromethyl)phenyl]-5H-pyrimido[5,4-d][2]benzazepin-2-amine |
| IV-298 | N-{4-[(4-aminopiperidin-1-yl)carbonyl]phenyl}-9-chloro-7-pyridin-2-yl-5H-pyrimido[5,4-d][2]benzazepin-2-amine |
| IV-299 | N-{4-[(3-aminopyrrolidin-1-yl)carbonyl]phenyl}-9-chloro-7-pyridin-2-yl-5H-pyrimido[5,4-d][2]benzazepin-2-amine |
| IV-300 | ethyl 2-amino-4-[(4-{[9-chloro-7-(2,6-difluorophenyl)-5H-pyrimido[5,4-d][2]benzazepin-2-yl]amino}benzoyl)amino]butanoate |
| IV-301 | 4-{[9-chloro-7-(3-fluoropyridin-2-yl)-5H-pyrimido[5,4-d][2]benzazepin-2-yl]amino}benzoic acid |
| IV-302 | 9-{[3-(dimethylamino)azetidin-1-yl]carbonyl}-7-(2-fluorophenyl)-N-(3-methoxyphenyl)-5H-pyrimido[5,4-d][2]benzazepin-2-amine |
| IV-303 | 7-(2-fluorophenyl)-2-[(3-methoxyphenyl)amino]-N-methyl-N-[3-(methylamino)propyl]-5H-pyrimido[5,4-d][2]benzazepine-9-carboxamide |
| IV-304 | N-{4-[(4-aminopiperidin-1-yl)carbonyl]phenyl}-9-chloro-7-(3-fluoropyridin-2-yl)-5H-pyrimido[5,4-d][2]benzazepin-2-amine |
| IV-305 | N-{4-[(3-aminopyrrolidin-1-yl)carbonyl]phenyl}-9-chloro-7-(3-fluoropyridin-2-yl)-5H-pyrimido[5,4-d][2]benzazepin-2-amine |
| IV-306 | 2-(4-{[9-chloro-7-(2,6-difluorophenyl)-5H-pyrimido[5,4-d][2]benzazepin-2-yl]amino}phenyl)-4,5-dihydro-1H-imidazole-5-carboxylic acid |
| IV-307 | N-(4-{[9-chloro-7-(2,6-difluorophenyl)-5H-pyrimido[5,4-d][2]benzazepin-2-yl]amino}phenyl)-2-(dimethylamino)acetamide |
| IV-308 | 2-amino-N-(4-{[9-chloro-7-(2,6-difluorophenyl)-5H-pyrimido[5,4-d][2]benzazepin-2-yl]amino}phenyl)-2-methylpropanamide |
| IV-309 | ethyl (2R)-4-amino-2-[(4-{[9-chloro-7-(2,6-difluorophenyl)-5H-pyrimido[5,4-d][2]benzazepin-2-yl]amino}benzoyl)amino]butanoate |
| IV-310 | 4-(4-{[9-chloro-7-(2,6-difluorophenyl)-5H-pyrimido[5,4-d][2]benzazepin-2-yl]amino}benzoyl)-N-methylpiperazine-2-carboxamide |
| IV-311 | 7-(2-fluorophenyl)-2-[(3-methoxyphenyl)amino]-N-(3-morpholin-4-ylpropyl)-5H-pyrimido[5,4-d][2]benzazepine-9-carboxamide |

TABLE 2-continued

Examples of Compounds of Formula (IV)

| | |
|---|---|
| IV-312 | 9-[(3,5-dimethylpiperazin-1-yl)carbonyl]-7-(2-fluorophenyl)-N-(3-methoxyphenyl)-5H-pyrimido[5,4-d][2]benzazepin-2-amine |
| IV-313 | 9-chloro-N-(3-chloro-4-{[4-(dimethylamino)piperidin-1-yl]carbonyl}phenyl)-7-(2,6-difluorophenyl)-5H-pyrimido[5,4-d][2]benzazepin-2-amine |
| IV-314 | ethyl 2-(4-{[9-chloro-7-(2,6-difluorophenyl)-5H-pyrimido[5,4-d][2]benzazepin-2-yl]amino}phenyl)-4,5-dihydro-1H-imidazole-5-carboxylate |
| IV-315 | 9-chloro-N-(4-{[3-(methylamino)pyrrolidin-1-yl]carbonyl}phenyl)-7-pyridin-2-yl-5H-pyrimido[5,4-d][2]benzazepin-2-amine |
| IV-316 | 9-chloro-N-(4-{[4-(methylamino)piperidin-1-yl]carbonyl}phenyl)-7-pyridin-2-yl-5H-pyrimido[5,4-d][2]benzazepin-2-amine |
| IV-317 | 4-(4-{[9-chloro-7-(2,6-difluorophenyl)-5H-pyrimido[5,4-d][2]benzazepin-2-yl]amino}benzoyl)piperazine-2-carboxamide |
| IV-318 | N-{4-[(3-aminopyrrolidin-1-yl)carbonyl]-3-chlorophenyl}-9-chloro-7-(2,6-difluorophenyl)-5H-pyrimido[5,4-d][2]benzazepin-2-amine |
| IV-319 | N-(4-{[9-chloro-7-(2,6-difluorophenyl)-5H-pyrimido[5,4-d][2]benzazepin-2-yl]amino}phenyl)piperidine-4-carboxamide |
| IV-320 | 4-{[9-chloro-7-(2-fluoro-6-{methyl[2-(methylamino)ethyl]amino}phenyl)-5H-pyrimido[5,4-d][2]benzazepin-2-yl]amino}benzoic acid |
| IV-321 | 9-chloro-7-(2,4-difluorophenyl)-N-{4-[(3,5-dimethylpiperazin-1-yl)carbonyl]phenyl}-5H-pyrimido[5,4-d][2]benzazepin-2-amine |
| IV-322 | 9-chloro-7-(2,4-dimethoxyphenyl)-N-{4-[(3,5-dimethylpiperazin-1-yl)carbonyl]phenyl}-5H-pyrimido[5,4-d][2]benzazepin-2-amine |
| IV-323 | 9-chloro-7-(2-chloro-6-fluorophenyl)-N-{4-[(3-methylpiperazin-1-yl)carbonyl]phenyl}-5H-pyrimido[5,4-d][2]benzazepin-2-amine |
| IV-324 | 9-chloro-7-(2-chloro-6-fluorophenyl)-N-{4-[(3,5-dimethylpiperazin-1-yl)carbonyl]phenyl}-5H-pyrimido[5,4-d][2]benzazepin-2-amine |
| IV-325 | 9-chloro-7-(2-chloro-6-fluorophenyl)-N-(4-{[4-(methylamino)piperidin-1-yl]carbonyl}phenyl)-5H-pyrimido[5,4-d][2]benzazepin-2-amine |
| IV-326 | 9-chloro-7-(2-chloro-6-fluorophenyl)-N-(4-{[3-(methylamino)piperidin-1-yl]carbonyl}phenyl)-5H-pyrimido[5,4-d][2]benzazepin-2-amine |
| IV-327 | 9-chloro-7-(2-chloro-6-fluorophenyl)-N-(4-{[3-(methylamino)pyrrolidin-1-yl]carbonyl}phenyl)-5H-pyrimido[5,4-d][2]benzazepin-2-amine |
| IV-328 | 9-chloro-N-(3,4-dimethoxyphenyl)-7-{2-[(dimethylamino)methyl]phenyl}-5H-pyrimido[5,4-d][2]benzazepin-2-amine |
| IV-329 | 9-chloro-7-(2-methoxyphenyl)-N-{4-[(3-methylpiperazin-1-yl)carbonyl]phenyl}-5H-pyrimido[5,4-d][2]benzazepin-2-amine |
| IV-330 | 9-chloro-N-{4-[(3,5-dimethylpiperazin-1-yl)carbonyl]phenyl}-7-(2-methoxyphenyl)-5H-pyrimido[5,4-d][2]benzazepin-2-amine |
| IV-331 | 9-chloro-7-(2-methoxyphenyl)-N-(4-{[4-(methylamino)piperidin-1-yl]carbonyl}phenyl)-5H-pyrimido[5,4-d][2]benzazepin-2-amine |
| IV-332 | 9-chloro-7-(2-methoxyphenyl)-N-(4-{[3-(methylamino)pyrrolidin-1-yl]carbonyl}phenyl)-5H-pyrimido[5,4-d][2]benzazepin-2-amine |
| IV-333 | 9-chloro-7-(2-methoxyphenyl)-N-(4-{[3-(methylamino)piperidin-1-yl]carbonyl}phenyl)-5H-pyrimido[5,4-d][2]benzazepin-2-amine |
| IV-334 | 4-{[9-chloro-7-(2,6-difluorophenyl)-5H-pyrimido[5,4-d][2]benzazepin-2-yl]amino}-N-methylbenzamide |
| IV-335 | 4-{[9-chloro-7-(2-fluoro-6-{methyl[3-(methylamino)propyl]amino}phenyl)-5H-pyrimido[5,4-d][2]benzazepin-2-yl]amino}benzoic acid |
| IV-336 | 4-{[9-chloro-7-(2-fluoro-6-{methyl[3-(methylamino)propyl]amino}phenyl)-5H-pyrimido[5,4-d][2]benzazepin-2-yl]amino}-N-methylbenzamide |
| IV-337 | 1-(4-{[9-chloro-7-(2,6-difluorophenyl)-5H-pyrimido[5,4-d][2]benzazepin-2-yl]amino}phenyl)ethanone |
| IV-338 | N-[3-(3-aminoprop-1-yn-1-yl)phenyl]-9-chloro-7-(2,6-difluorophenyl)-5H-pyrimido[5,4-d][2]benzazepin-2-amine |
| IV-339 | 4-[(9-chloro-7-{2-fluoro-6-[(2-hydroxyethyl)amino]phenyl}-5H-pyrimido[5,4-d][2]benzazepin-2-yl)amino]-N-methylbenzamide |
| IV-340 | 4-[(7-{2-[(2-aminoethyl)amino]-6-fluorophenyl}-9-chloro-5H-pyrimido[5,4-d][2]benzazepin-2-yl)amino]-N-methylbenzamide |
| IV-341 | 4-amino-1-(4-{[9-chloro-7-(2,6-difluorophenyl)-5H-pyrimido[5,4-d][2]benzazepin-2-yl]amino}benzoyl)-N-methylpiperidine-4-carboxamide |
| IV-342 | 4-[(9-chloro-7-{2-[4-(dimethylamino)piperidin-1-yl]-6-fluorophenyl}-5H-pyrimido[5,4-d][2]benzazepin-2-yl)amino]-N-methylbenzamide |
| IV-343 | 9-chloro-7-(2,6-difluorophenyl)-N-{3-[3-(dimethylamino)prop-1-yn-1-yl]phenyl}-5H-pyrimido[5,4-d][2]benzazepin-2-amine |
| IV-344 | 9-chloro-7-(2,6-difluorophenyl)-N-(3-iodophenyl)-5H-pyrimido[5,4-d][2]benzazepin-2-amine |
| IV-345 | 4-{[9-chloro-7-(2-{[2-(dimethylamino)ethyl]amino}-6-fluorophenyl)-5H-pyrimido[5,4-d][2]benzazepin-2-yl]amino}-N-methylbenzamide |
| IV-346 | 4-[(9-chloro-7-{2-[[2-(dimethylamino)ethyl](methyl)amino]-6-fluorophenyl}-5H-pyrimido[5,4-d][2]benzazepin-2-yl)amino]-N-methylbenzamide |
| IV-347 | 4-{[9-chloro-7-(2-fluoro-6-{methyl[2-(methylamino)ethyl]amino}phenyl)-5H-pyrimido[5,4-d][2]benzazepin-2-yl]amino}-N-methylbenzamide |
| IV-348 | 4-({7-[2-(4-aminopiperidin-1-yl)-6-fluorophenyl]-9-chloro-5H-pyrimido[5,4-d][2]benzazepin-2-yl}amino)-N-methylbenzamide |
| IV-349 | 7-(2-fluorophenyl)-2-[(3-methoxyphenyl)amino]-N-methyl-N-[2-(methylamino)ethyl]-5H-pyrimido[5,4-d][2]benzazepine-9-carboxamide |
| IV-350 | 4-amino-1-(4-{[9-chloro-7-(2,6-difluorophenyl)-5H-pyrimido[5,4-d][2]benzazepin-2-yl]amino}benzoyl)piperidine-4-carboxamide |

TABLE 2-continued

Examples of Compounds of Formula (IV)

| | |
|---|---|
| IV-351 | 9-chloro-7-(2-chloro-6-fluorophenyl)-N-(4-{[3-(methylamino)azetidin-1-yl]carbonyl}phenyl)-5H-pyrimido[5,4-d][2]benzazepin-2-amine |
| IV-352 | 9-chloro-7-(2,6-difluorophenyl)-N-(4-methyl-1,3-thiazol-2-yl)-5H-pyrimido[5,4-d][2]benzazepin-2-amine |
| IV-353 | 7-(2,6-difluorophenyl)-2-[(3-methoxyphenyl)amino]-5H-pyrimido[5,4-d][2]benzazepine-9-carboxylic acid |
| IV-354 | 4-({9-chloro-7-[2-fluoro-6-(methylamino)phenyl]-5H-pyrimido[5,4-d][2]benzazepin-2-yl}amino)-N-methylbenzamide |
| IV-355 | 2-{[9-chloro-7-(2,6-difluorophenyl)-5H-pyrimido[5,4-d][2]benzazepin-2-yl]amino}-N-methyl-1,3-thiazole-4-carboxamide |
| IV-356 | N-1H-benzimidazol-2-yl-9-chloro-7-(2,6-difluorophenyl)-5H-pyrimido[5,4-d][2]benzazepin-2-amine |
| IV-357 | 7-(2,6-difluorophenyl)-2-[(4-methyl-1,3-thiazol-2-yl)amino]-5H-pyrimido[5,4-d][2]benzazepine-9-carboxylic acid |
| IV-358 | 3-amino-1-(3-{[9-chloro-7-(2,6-difluorophenyl)-5H-pyrimido[5,4-d][2]benzazepin-2-yl]amino}phenyl)propan-1-one |
| IV-359 | 1-(3-{[9-chloro-7-(2,6-difluorophenyl)-5H-pyrimido[5,4-d][2]benzazepin-2-yl]amino}phenyl)-3-(dimethylamino)propan-1-one |
| IV-360 | 2-{[9-chloro-7-(2,6-difluorophenyl)-5H-pyrimido[5,4-d][2]benzazepin-2-yl]amino}-1,3-thiazole-4-carboxylic acid |
| IV-361 | ethyl 2-{[9-chloro-7-(2,6-difluorophenyl)-5H-pyrimido[5,4-d][2]benzazepin-2-yl]amino}-1,3-thiazole-4-carboxylate |
| IV-362 | 9-chloro-7-(2,6-difluorophenyl)-N-{4-[(3,5-dimethylpiperazin-1-yl)carbonyl]-1,3-thiazol-2-yl}-5H-pyrimido[5,4-d][2]benzazepin-2-amine |
| IV-363 | ethyl 2-{[9-chloro-7-(2,6-difluorophenyl)-5H-pyrimido[5,4-d][2]benzazepin-2-yl]amino}-1,3-oxazole-5-carboxylate |
| IV-364 | 2-{[9-chloro-7-(2,6-difluorophenyl)-5H-pyrimido[5,4-d][2]benzazepin-2-yl]amino}-1,3-oxazole-5-carboxylic acid |
| IV-365 | 9-chloro-7-(2,6-difluorophenyl)-N-(4-{[(3R)-3-methylpiperazin-1-yl]carbonyl}-1,3-thiazol-2-yl)-5H-pyrimido[5,4-d][2]benzazepin-2-amine |
| IV-366 | 9-chloro-7-(2,6-difluorophenyl)-N-(4-{[(2R)-2-methylpiperazin-1-yl]carbonyl}phenyl)-5H-pyrimido[5,4-d][2]benzazepin-2-amine |
| IV-367 | 9-chloro-7-(2,6-difluorophenyl)-N-(4-{[3-(methylamino)pyrrolidin-1-yl]carbonyl}-1,3-thiazol-2-yl)-5H-pyrimido[5,4-d][2]benzazepin-2-amine |
| IV-368 | 2-{[9-chloro-7-(2,6-difluorophenyl)-5H-pyrimido[5,4-d][2]benzazepin-2-yl]amino}-1,3-oxazole-4-carboxylic acid |
| IV-369 | 9-chloro-7-(2,6-difluorophenyl)-N-{5-[(3,5-dimethylpiperazin-1-yl)carbonyl]-1,3-oxazol-2-yl}-5H-pyrimido[5,4-d][2]benzazepin-2-amine |
| IV-370 | 9-chloro-7-(2,6-difluorophenyl)-N-(5-{[3-(methylamino)pyrrolidin-1-yl]carbonyl}-1,3-oxazol-2-yl)-5H-pyrimido[5,4-d][2]benzazepin-2-amine |
| IV-371 | 4-{[9-chloro-7-(2,6-difluorophenyl)-5-methyl-5H-pyrimido[5,4-d][2]benzazepin-2-yl]amino}benzoic acid |
| IV-372 | 9-chloro-7-(2,6-difluorophenyl)-N-{3-[3-(dimethylamino)propyl]phenyl}-5H-pyrimido[5,4-d][2]benzazepin-2-amine |
| IV-373 | N-[3-(3-aminopropyl)phenyl]-9-chloro-7-(2,6-difluorophenyl)-5H-pyrimido[5,4-d][2]benzazepin-2-amine |
| IV-374 | 9-chloro-7-(2,6-difluorophenyl)-N-{4-[(3,5-dimethylpiperazin-1-yl)carbonyl]-1,3-oxazol-2-yl}-5H-pyrimido[5,4-d][2]benzazepin-2-amine |
| IV-375 | 9-chloro-7-(2,6-difluorophenyl)-N-(4-{[3-(methylamino)pyrrolidin-1-yl]carbonyl}-1,3-oxazol-2-yl)-5H-pyrimido[5,4-d][2]benzazepin-2-amine |
| IV-376 | 7-(2,6-difluorophenyl)-2-({4-[(3,5-dimethylpiperazin-1-yl)carbonyl]phenyl}amino)-N-methyl-5H-pyrimido[5,4-d][2]benzazepine-9-carboxamide |
| IV-377 | 2-{[4-(aminocarbonyl)phenyl]amino}-7-(2,6-difluorophenyl)-5H-pyrimido[5,4-d][2]benzazepine-9-carboxylic acid |
| IV-378 | 1-(4-{[9-chloro-7-(2,6-difluorophenyl)-5H-pyrimido[5,4d][2]benzazepin-2-yl]amino}benzoyl)-N-methyl-4-(methylamino)piperidine-4-carboxamide |
| IV-379 | N-{4-[(3-amino-3-methylpyrrolidin-1-yl)carbonyl]phenyl}-9-chloro-7-(2,6-difluorophenyl)-5H-pyrimido[5,4-d][2]benzazepin-2-amine |
| IV-380 | 9-chloro-7-(2,6-difluorophenyl)-N-(4-{[3-methyl-3-(methylamino)pyrrolidin-1-yl]carbonyl}phenyl)-5H-pyrimido[5,4-d][2]benzazepin-2-amine |
| IV-381 | 1-(4-{[9-chloro-7-(2,6-difluorophenyl)-5H-pyrimido[5,4-d][2]benzazepin-2-yl]amino}benzoyl)-4-(methylamino)piperidine-4-carboxamide |
| IV-382 | 9-chloro-7-(2,6-difluorophenyl)-N-{4-[(3,3,5-trimethylpiperazin-1-yl)carbonyl]phenyl}-5H-pyrimido[5,4-d][2]benzazepin-2-amine |
| IV-383 | N-1-azabicyclo[2.2.2]oct-3-yl-4-{[9-chloro-7-(2,6-difluorophenyl)-5H-pyrimido[5,4-d][2]benzazepin-2-yl]amino}-N-methylbenzamide |
| IV-384 | N-1-azabicyclo[2.2.2]oct-3-yl-4-{[9-chloro-7-(2,6-difluorophenyl)-5H-pyrimido[5,4-d][2]benzazepin-2-yl]amino}benzamide |
| IV-385 | 4-{[9-chloro-7-(2,6-difluorophenyl)-5H-pyrimido[5,4-d][2]benzazepin-2-yl]amino}-N-hydroxybenzamide |
| IV-386 | N-{4-[(aminooxy)carbonyl]phenyl}-9-chloro-7-(2,6-difluorophenyl)-5H-pyrimido[5,4-d][2]benzazepin-2-amine |
| IV-387 | 4-{[9-chloro-7-(2,6-difluorophenyl)-7H-pyrimido[5,4-d][2]benzazepin-2-yl]amino}benzoic acid |
| IV-388 | 4-{[9-chloro-7-(2,3-difluorophenyl)-7H-pyrimido[5,4-d][2]benzazepin-2-yl]amino}benzoic acid |

TABLE 2-continued

Examples of Compounds of Formula (IV)

| | |
|---|---|
| IV-389 | 3-amino-1-(4-{[9-chloro-7-(2,6-difluorophenyl)-5H-pyrimido[5,4-d][2]benzazepin-2-yl]amino}benzoyl)-N-methylpyrrolidine-3-Icarboxamide |
| IV-390 | 3-amino-1-(2-chloro-4-{[9-chloro-7-(2,6-difluorophenyl)-5H-pyrimido[5,4-d][2]benzazepin-2-yl]amino}benzoyl)pyrrolidine-3-carboxamide |
| IV-391 | 9-chloro-7-(2,6-difluorophenyl)-N-{4-[(3,3-dimethylpiperazin-1-yl)carbonyl]phenyl}-5H-pyrimido[5,4-d][2]benzazepin-2-amine |
| IV-392 | 4-{[9-chloro-7-(2,6-difluorophenyl)-5H-pyrimido[5,4-d][2]benzazepin-2-yl]amino}-N-(8-methyl-8-azabicyclo[3.2.1]oct-3-yl)benzamide |
| IV-393 | 9-chloro-7-(2,6-difluorophenyl)-N-(4-{[3-(dimethylamino)-3-methylpyrrolidin-1-yl]carbonyl}phenyl)-5H-pyrimido[5,4-d][2]benzazepin-2-amine |
| IV-394 | 9-chloro-7-(2,6-difluorophenyl)-N-(3-methyl-1H-pyrazol-5-yl)-5H-pyrimido[5,4-d][2]benzazepin-2-amine |
| IV-395 | 2-chloro-4-{[9-chloro-7-(2,6-difluorophenyl)-5H-pyrimido[5,4-d][2]benzazepin-2-yl]amino}benzoic acid |
| IV-396 | 4-amino-1-(2-chloro-4-{[9-chloro-7-(2,6-difluorophenyl)-5H-pyrimido[5,4-d][2]benzazepin-2-yl]amino}benzoyl)-N-methylpiperidine-4-carboxamide |
| IV-397 | 4-amino-1-(2-chloro-4-{[9-chloro-7-(2,6-difluorophenyl)-5H-pyrimido[5,4-d][2]benzazepin-2-yl]amino}benzoyl)-N,N-dimethylpiperidine-4-carboxamide |
| IV-398 | 4-[(9-methoxy-7-oxo-6,7-dihydro-5H-pyrimido[5,4-d][2]benzazepin-2-yl)amino]benzoic acid |
| IV-399 | 2-({4-[(3,5-dimethylpiperazin-1-yl)carbonyl]phenyl}amino)-9-methoxy-5,6-dihydro-7H-pyrimido[5,4-d][2]benzazepin-7-one |
| IV-400 | 9-methoxy-2-[(4-{[3-(methylamino)pyrrolidin-1-yl]carbonyl}phenyl)amino]-5,6-dihydro-7H-pyrimido[5,4-d][2]benzazepin-7-one |
| IV-401 | 4-[(8-methyl-7-oxo-5,6,7,8-tetrahydropyrimido[5,4-c]pyrrolo[3,2-e]azepin-2-yl)amino]benzoic acid |
| IV-402 | 2-({4-[(3,5-dimethylpiperazin-1-yl)carbonyl]phenyl}amino)-8-methyl-5,8-dihydropyrimido[5,4-c]pyrrolo[3,2-e]azepin-7(6H)-one |
| IV-403 | 2-[(3-methoxyphenyl)amino]-8-methyl-5,8-dihydropyrimido[5,4-c]pyrrolo[3,2-e]azepin-7(6H)-one |
| IV-404 | 9-chloro-2-[(3,4-dimethoxyphenyl)amino]-5,6-dihydro-7H-pyrimido[5,4-d][2]benzazepin-7-one |
| IV-405 | 4-{[4-amino-9-chloro-7-(2,6-difluorophenyl)-5H-pyrimido[5,4-d][2]benzazepin-2-yl]amino}benzoic acid |
| IV-406 | 9-chloro-N-(3-chloro-4-{[4-(methylamino)piperidin-1-yl]carbonyl}phenyl)-7-(2,6-difluorophenyl)-5H-pyrimido[5,4-d][2]benzazepin-2-amine |
| IV-407 | 9-chloro-N-(3-chloro-4-{[4-(methylamino)piperidin-1-yl]carbonyl}phenyl)-7-(2-fluoro-6-methoxyphenyl)-5H-pyrimido[5,4-d][2]benzazepin-2-amine |
| IV-408 | 4-{[9-chloro-7-(2-fluoro-6-hydroxyphenyl)-5H-pyrimido[5,4-d][2]benzazepin-2-yl]amino}benzoic acid |
| IV-409 | 9-chloro-N-[4-(1,7-diazaspiro[4.4]non-7-ylcarbonyl)phenyl]-7-(2,6-difluorophenyl)-5H-pyrimido[5,4-d][2]benzazepin-2-amine |
| IV-410 | 9-chloro-7-(2,6-difluorophenyl)-N-(4-{[2-(methylamino)-7-azabicyclo[2.2.1]hept-7-yl]carbonyl}phenyl)-5H-pyrimido[5,4-d][2]benzazepin-2-amine |
| IV-411 | 1-(4-{[9-chloro-7-(2,6-difluorophenyl)-5H-pyrimido[5,4-d][2]benzazepin-2-yl]amino}benzoyl)-N-methyl-3-(methylamino)pyrrolidine-3-carboxamide |
| IV-412 | 1-(4-{[9-chloro-7-(2,6-difluorophenyl)-5H-pyrimido[5,4-d][2]benzazepin-2-yl]amino}benzoyl)-3-(methylamino)pyrrolidine-3-carboxamide |
| IV-413 | 1-(2-chloro-4-{[9-chloro-7-(2,6-difluorophenyl)-5H-pyrimido[5,4-d][2]benzazepin-2-yl]amino}benzoyl)-N-methyl-3-(methylamino)piperidine-3-carboxamide |
| IV-414 | 9-chloro-7-(2,6-difluorophenyl)-N-(4-{[3-methyl-3-(methylamino)piperidin-1-yl]carbonyl}phenyl)-5H-pyrimido[5,4-d][2]benzazepin-2-amine |
| IV-415 | 9-chloro-7-(2-fluoro-6-methoxyphenyl)-N-(4-{[3-methyl-3-(methylamino)piperidin-1-yl]carbonyl}phenyl)-5H-pyrimido[5,4-d][2]benzazepin-2-amine |
| IV-416 | {2-Chloro-4-[9-chloro-7-(2-fluoro-6-methoxy-phenyl)-5H-benzo[c]pyrimido[4,5-e]azepin-2-ylamino]-phenyl}-(3-methyl-3-methylamino-piperidin-1-yl)-methanone |
| IV-417 | 9-chloro-7-(2,6-difluorophenyl)-N-(4-{[4-methyl-4-(methylamino)piperidin-1-yl]carbonyl}phenyl)-5H-pyrimido[5,4-d][2]benzazepin-2-amine |
| IV-418 | 9-chloro-7-(2,6-difluorophenyl)-N-(4-{[4-(dimethylamino)-4-methylpiperidin-1-yl]carbonyl}phenyl)-5H-pyrimido[5,4-d][2]benzazepin-2-amine |
| IV-419 | N-{4-[(4-amino-4-methylpiperidin-1-yl)carbonyl]phenyl}-9-chloro-7-(2,6-difluorophenyl)-5H-pyrimido[5,4-d][2]benzazepin-2-amine |
| IV-420 | 9-chloro-N-(3-chloro-4-{[4-methyl-4-(methylamino)piperidin-1-yl]carbonyl}phenyl)-7-(2,6-difluorophenyl)-5H-pyrimido[5,4-d][2]benzazepin-2-amine |
| IV-421 | 9-chloro-7-(2-fluoro-6-methoxyphenyl)-N-(4-{[4-methyl-4-(methylamino)piperidin-1-yl]carbonyl}phenyl)-5H-pyrimido[5,4-d][2]benzazepin-2-amine |
| IV-422 | 2-Chloro-4-[9-chloro-7-(2-fluoro-6-methoxy-phenyl)-5H-benzo[c]pyrimido[4,5-e]azepin-2-ylamino]-phenyl}-(4-methyl-4-methylamino-piperidin-1-yl)-methanone |
| IV-423 | 9-chloro-7-(2-fluoro-6-methoxyphenyl)-N-(3-fluoro-4-{[4-methyl-4-(methylamino)piperidin-1-yl]carbonyl}phenyl)-5H-pyrimido[5,4-d][2]benzazepin-2-amine |

TABLE 2-continued

Examples of Compounds of Formula (IV)

| | |
|---|---|
| IV-424 | 9-chloro-N-{3-chloro-4-[(3,3,5,5-tetramethylpiperazin-1-yl)carbonyl]phenyl}-7-(2-fluoro-6-methoxyphenyl)-5H-pyrimido[5,4-d][2]benzazepin-2-amine |
| IV-425 | N-1-azabicyclo[2.2.2]oct-3-yl-4-{[9-chloro-7-(2,6-difluorophenyl)-5H-pyrimido[5,4-d][2]benzazepin-2-yl]amino}-2-fluoro-N-methylbenzamide |
| IV-426 | N-1-azabicyclo[2.2.2]oct-3-yl-4-{[9-chloro-7-(2-fluoro-6-methoxyphenyl)-5H-pyrimido[5,4-d][2]benzazepin-2-yl]amino}-N-methylbenzamide |
| IV-427 | N-8-azabicyclo[3.2.1]oct-3-yl-4-{[9-chloro-7-(2,6-difluorophenyl)-5H-pyrimido[5,4-d][2]benzazepin-2-yl]amino}-N-methylbenzamide |
| IV-428 | 9-chloro-7-(2,6-difluorophenyl)-N-(4-{[3-(methylamino)-8-azabicyclo[3.2.1]oct-8-yl]carbonyl}phenyl)-5H-pyrimido[5,4-d][2]benzazepin-2-amine |
| IV-429 | 9-chloro-7-(2-fluoro-6-methoxyphenyl)-N-(4-{[3-(methylamino)-8-azabicyclo[3.2.1]oct-8-yl]carbonyl}phenyl)-5H-pyrimido[5,4-d][2]benzazepin-2-amine |
| IV-430 | 4-{[7-(2,6-difluorophenyl)-9-methyl-5H-pyrimido[5,4-c]thieno[2,3-e]azepin-2-yl]amino}benzoic acid |
| IV-431 | 7-(2,6-difluorophenyl)-N-{4-[(3,3,5,5-tetramethylpiperazin-1-yl)carbonyl]phenyl}-5H-pyrimido[5,4-c]thieno[2,3-e]azepin-2-amine |
| IV-432 | N-{4-[(3-amino-3-methylpyrrolidin-1-yl)carbonyl]phenyl}-7-(2,6-difluorophenyl)-10-methyl-5,10-dihydropyrimido[5,4-c]pyrrolo[2,3-e]azepin-2-amine |
| IV-433 | 7-(2,6-difluorophenyl)-9-methyl-N-(4-{[3-(methylamino)pyrrolidin-1-yl]carbonyl}phenyl)-5H-furo[2,3-c]pyrimido[4,5-e]azepin-2-amine |
| IV-434 | 4-(2,6-difluorophenyl)-2-methyl-N-(4-{[3-methyl-3-(methylamino)pyrrolidin-1-yl]carbonyl}phenyl)-6H-pyrimido[5,4-c][1,3]thiazolo[4,5-e]azepin-9-amine |
| IV-435 | N-{4-[(3-amino-3-methylpyrrolidin-1-yl)carbonyl]phenyl}-7-(2-fluoro-6-methoxyphenyl)-5,9-dihydropyrimido[5,4-c]pyrrolo[3,4-e]azepin-2-amine |
| IV-436 | 4-{[4-(2,6-difluorophenyl)-1-methyl-1,6-dihydropyrazolo[4,3-c]pyrimido[4,5-e]azepin-9-yl]amino}benzoic acid |
| IV-437 | 1-{4-[4-(2,6-Difluoro-phenyl)-2-methyl-6H-3-thia-5,8,10-triaza-benzo[e]azulen-9-ylamino]-benzoyl}-4-dimethylamino-piperidine-4-carboxylic acid methylamide |
| IV-438 | 4-(4-{[7-(2,6-difluorophenyl)-5H-furo[3,2-c]pyrimido[4,5-e]azepin-2-yl]amino}benzoyl)-N-methylpiperazine-2-carboxamide |
| IV-439 | 4-(4-{[4-(2,6-difluorophenyl)-6H-isoxazolo[4,5-c]pyrimido[4,5-e]azepin-9-yl]amino}benzoyl)-N-methylpiperazine-2-carboxamide |
| IV-440 | 4-(2,6-difluorophenyl)-9-[(4-{[3-methyl-3-(methylamino)pyrrolidin-1-yl]carbonyl}phenyl)amino]-3,6-dihydroimidazo[4,5-c]pyrimido[4,5-e]azepin-2(1H)-one |
| IV-441 | 2-amino-N-(3-{[7-(2,6-difluorophenyl)-8,10-dimethyl-5H-pyrimido[5,4-c]thieno[3,4-e]azepin-2-yl]amino}phenyl)-N,2-dimethylpropanamide |
| IV-442 | 9-chloro-7-(2,6-difluorophenyl)-N-{3-[(2,2,6,6-tetramethylpiperidin-4-yl)oxy]phenyl}-5H-pyrimido[5,4-d][2]benzazepin-2-anime |
| IV-443 | 4-(4-{[9-chloro-7-(2,6-difluorophenyl)-5H-pyrimido[5,4-d][2]benzazepin-2-yl]amino}phenyl)-N-methyl-1-(methylamino)cyclohexanecarboxamide |
| IV-444 | 7-(3-{[7-(2-fluoro-6-methoxyphenyl)-9-methoxy-5H-pyrimido[5,4-d][2]benzazepin-2-yl]amino}phenyl)-1,7-diazaspiro[4.4]nonan-6-one |
| IV-445 | 9-chloro-N-[4-(3,8-diazabicyclo[3.2.1]oct-3-ylcarbonyl)phenyl]-7-(2,6-difluorophenyl)-5H-pyrimido[5,4-d][2]benzazepin-2-amine |
| IV-446 | 1-(3-{[9-chloro-7-(2,6-difluorophenyl)-5H-pyrimido[5,4-d][2]benzazepin-2-yl]amino}phenyl)-3,5,5-trimethylpiperazin-2-one |
| IV-447 | 9-chloro-N-[4-(2,6-dimethylpiperidin-4-yl)phenyl]-7-(2-fluoro-6-methoxyphenyl)-5H-pyrimido[5,4-d][2]benzazepin-2-amine |
| IV-448 | N-[4-(1-amino-1-methylethyl)phenyl]-9-chloro-7-(2,6-difluorophenyl)-5H-pyrimido[5,4-d][2]benzazepin-2-amine |
| IV-449 | N-[4-(2,5-diazaspiro[3.4]oct-2-ylcarbonyl)phenyl]-7-(2,6-difluorophenyl)-10-methyl-5H-isothiazolo[5,4-c]pyrimido[4,5-e]azepin-2-amine |
| IV-450 | 4-(2,6-difluorophenyl)-1-methyl-9-[(4-{[4-methyl-4-(methylamino)piperidin-1-yl]carbonyl}phenyl)amino]-1,6-dihydro-2H-pyrimido[5,4-c][1,3]thiazolo[4,5-e]azepin-2-one |
| IV-451 | 4-(2,6-difluorophenyl)-N-[4-(1H-imidazol-2-yl)phenyl]-1-methyl-1,6-dihydroimidazo[4,5-c]pyrimido[4,5-e]azepin-9-amine |
| IV-452 | 4-{[7-(2,6-difluorophenyl)-5H-[1]benzofuro[2,3-c]pyrimido[4,5-e]azepin-2-yl]amino}benzoic acid |
| IV-453 | 7-(2-fluorophenyl)-N-{4-[(3,3,5,5-tetramethylpiperazin-1-yl)carbonyl]phenyl}-8,9,10,11-tetrahydro-5H-pyrido[4',3':4,5]thieno[3,2-c]pyrimido[4,5-e]azepin-2-amine |
| IV-454 | 9-bromo-7-(2-fluorophenyl)-N-(4-{[3-(methylamino)pyrrolidin-1-yl]carbonyl}phenyl)-5,8-dihydropyrimido[5,4-c]pyrrolo[3,2-e]azepin-2-amine |
| IV-455 | 7-(2-fluorophenyl)-N-(3-methyl-1H-indazol-6-yl)-5,12-dihydropyrimido[4',5':5,6]azepino[4,3-b]indol-2-amine |
| IV-456 | 1-(4-{[7-(2,6-difluorophenyl)-9,10-dimethyl-5,8-dihydropyrimido[5,4-c]pyrrolo[3,2-e]azepin-2-yl]amino}benzoyl)-3-(methylamino)pyrrolidine-3-carboxamide |
| IV-457 | {3-[9-Chloro-7-(2-fluoro-6-methoxy-phenyl)-5H-benzo[c]pyrimido-[4,5-e]azepin-2-ylamino]-phenyl}-(4-methyl-piperazin-1-yl)-methanone |
| IV-458 | [9-Chloro-7-(2,6-difluoro-phenyl)-5H-benzo[c]pyrimido[4,5-e]azepin-2-yl]-(2-methylaminomethyl-benzothiazol-6-yl)-amine |

TABLE 2-continued

Examples of Compounds of Formula (IV)

| | |
|---|---|
| IV-459 | 4-[9-Chloro-7-(2-isopropoxy-phenyl)-5H-benzo[c]pyrimido[4,5-e]azepin-2-ylamino]-benzoic acid |
| IV-460 | 4-[9-Chloro-7-(2-fluoro-6-isopropoxy-phenyl)-5H-benzo[c]pyrimido-[4,5-e]azepin-2-ylamino]-benzoic acid |
| IV-461 | 4-[9-Chloro-7-(2-ethoxy-phenyl)-5H-benzo[c]pyrimido[4,5-e]azepin-2-ylamino]-benzoic acid |
| IV-462 | 4-[9-Chloro-7-(2-ethoxy-6-fluoro-phenyl)-5H-benzo[c]pyrimido[4,5-e]azepin-2-ylamino]-benzoic acid |
| IV-463 | 4-[9-Chloro-7-(2-fluoro-6-methyl-phenyl)-5H-benzo[c]pyrimido[4,5-e]azepin-2-ylamino]-benzoic acid |
| IV-464 | 4-[9-Chloro-7-(2-trifluoromethoxy-phenyl)-5H-benzo[c]pyrimido[4,5-e]azepin-2-ylamino]-benzoic acid |
| IV-465 | 4-[9-Chloro-7-(2-fluoro-6-trifluoromethoxy-phenyl)-5H-benzo[c]pyrimido-[4,5-e]azepin-2-ylamino]-benzoic acid |
| IV-466 | 4-[9-Chloro-7-(3-fluoro-2-trifluoromethoxy-phenyl)-5H-benzo[c]pyrimido-[4,5-e]azepin-2-ylamino]-benzoic acid |
| IV-467 | 4-[9-Chloro-7-(2,3-dimethoxy-phenyl)-5H-benzo[c]pyrimido[4,5-e]azepin-2-ylamino]-benzoic acid |
| IV-468 | 4-[9-Chloro-7-(2-isobutyl-phenyl)-5H-benzo[c]pyrimido[4,5-e]azepin-2-ylamino]-benzoic acid |
| IV-469 | 4-(7-Benzofuran-2-yl-9-chloro-5H-benzo[c]pyrimido[4,5-e]azepin-2-ylamino)-benzoic acid |
| IV-470 | 4-[9-Chloro-7-(1-methyl-1H-pyrrol-2-yl)-5H-benzo[c]pyrimido[4,5-e]azepin-2-ylamino]-benzoic acid |
| IV-471 | 4-[9-Chloro-7-(1-methyl-1H-imidazol-2-yl)-5H-benzo[c]pyrimido[4,5-e]azepin-2-ylamino]-benzoic acid |
| IV-472 | 4-(9-Chloro-7-thiophen-2-yl-5H-benzo[c]pyrimido[4,5-e]azepin-2-ylamino)-benzoic acid |
| IV-473 | 4-[9-Chloro-7-(2H-pyrazol-3-yl)-5H-benzo[c]pyrimido[4,5-e]azepin-2-ylamino]-benzoic acid |
| IV-474 | 4-[9-Chloro-7-(2-ethynyl-phenyl)-5H-benzo[c]pyrimido[4,5-e]azepin-2-ylamino]-benzoic acid |
| IV-475 | 4-[7-(2-Aminomethyl-phenyl)-9-chloro-5H-benzo[c]pyrimido[4,5-e]azepin-2-ylamino]-benzoic acid |
| IV-476 | 4-[9-Chloro-7-(5-fluoro-2-methoxy-phenyl)-5H-benzo[c]pyrimido[4,5-e]azepin-2-ylamino]-benzoic acid |
| IV-477 | 4-[9-Chloro-7-(3-methoxy-pyridin-2-yl)-5H-benzo[c]pyrimido[4,5-e]azepin-2-ylamino]-benzoic acid |
| IV-478 | 4-[8-Fluoro-7-(2-fluoro-phenyl)-5H-benzo[c]pyrimido[4,5-e]azepin-2-ylamino]-benzoic acid |
| IV-479 | 4-[8-Chloro-7-(2-fluoro-phenyl)-5H-benzo[c]pyrimido[4,5-e]azepin-2-ylamino]-benzoic acid |
| IV-480 | 4-[11-Fluoro-7-(2-fluoro-phenyl)-5H-benzo[c]pyrimido[4,5-e]azepin-2-ylamino]-benzoic acid |
| IV-481 | 4-[11-Chloro-7-(2-fluoro-phenyl)-5H-benzo[c]pyrimido[4,5-e]azepin-2-ylamino]-benzoic acid |
| IV-482 | 6-[9-Chloro-7-(2-fluoro-phenyl)-5H-benzo[c]pyrimido[4,5-e]azepin-2-ylamino]-pyridazine-3-carboxylic acid |
| IV-483 | 2-[9-Chloro-7-(2-fluoro-phenyl)-5H-benzo[c]pyrimido[4,5-e]azepin-2-ylamino]-1H-imidazole-4-carboxylic acid |
| IV-484 | 4-[9-Chloro-7-(2-fluoro-phenyl)-4-methyl-5H-benzo[c]pyrimido[4,5-e]azepin-2-ylamino]-benzoic acid |
| IV-485 | 4-[4-Aminomethyl-9-chloro-7-(2-fluoro-phenyl)-5H-benzo[c]pyrimido-[4,5-e]azepin-2-ylamino]-benzoic acid |
| IV-486 | 4-(9-Aminomethyl-7-phenyl-5H-benzo[c]pyrimido[4,5-e]azepin-2-ylamino)-benzoic acid |
| IV-487 | 9-Chloro-7-(2-fluorophenyl)-N-{4-[(2-methylpiperazin-1-yl)carbonyl]phenyl}-5H-pyrimido[5,4-d][2]benzazepin-2-amine |
| IV-488 | 4-{[9-Chloro-7-(2-fluorophenyl)-5H-pyrimido[5,4-d][2]benzazepin-2-yl]amino}-N-[{3-[(dimethylamino)methyl]azetidin-1-yl}(imino)methyl]benzamide |
| IV-489 | 4-{[9-Chloro-7-(2-fluorophenyl)-5H-pyrimido[5,4-d][2]benzazepin-2-yl]amino}-N-[imino(piperazin-1-yl)methyl]benzamide |
| IV-490 | 4-{[9-Chloro-7-(2-fluorophenyl)-5H-pyrimido[5,4-d][2]benzazepin-2-yl]amino}-N-[imino(3-methylpiperazin-1-yl)methyl]benzamide |
| IV-491 | 4-{[9-Chloro-7-(2-fluorophenyl)-5H-pyrimido[5,4-d][2]benzazepin-2-yl]amino}-N-[[3-(dimethylamino)pyrrolidin-1-yl](imino)methyl]benzamide |
| IV-492 | 4-{[9-Chloro-7-(2-fluorophenyl)-5H-pyrimido[5,4-d][2]benzazepin-2-yl]amino}-N-[imino(4-methylpiperazin-1-yl)methyl]benzamide |
| IV-493 | 4-{[9-Chloro-7-(2-fluorophenyl)-5H-pyrimido[5,4-d][2]benzazepin-2-yl]amino}-N-[(3,5-dimethylpiperazin-1-yl)(imino)methyl]benzamide |
| IV-494 | 1-[[(4-{[9-Chloro-7-(2-fluorophenyl)-5H-pyrimido[5,4-d][2]benzazepin-2-yl]amino}benzoyl)amino](imino)methyl]pyrrolidine-3-carboxamide |
| IV-495 | 1-[[(4-{[9-Chloro-7-(2-fluorophenyl)-5H-pyrimido[5,4-d][2]benzazepin-2-yl]amino}benzoyl)amino](imino)methyl]piperidine-3-carboxamide |
| IV-496 | 4-{[9-Chloro-7-(2-fluorophenyl)-5H-pyrimido[5,4-d][2]benzazepin-2-yl]amino}-N-[{4-[(cyclopropylcarbonyl)amino]piperidin-1-yl}(imino)methyl]benzamide |

TABLE 2-continued

Examples of Compounds of Formula (IV)

| | |
|---|---|
| IV-497 | 4-{[9-Chloro-7-(2-fluorophenyl)-5H-pyrimido[5,4-d][2]benzazepin-2-yl]amino}-N-[(dimethylamino)(imino)methyl]benzamide |
| IV-498 | N-[[(4-{[9-Chloro-7-(2-fluorophenyl)-5H-pyrimido[5,4-d][2]benzazepin-2-yl]amino}phenyl)amino](imino)methyl]cyclopropanecarboxamide |
| IV-499 | N-[[(4-{[9-Chloro-7-(2-fluorophenyl)-5H-pyrimido[5,4-d][2]benzazepin-2-yl]amino}phenyl)amino](imino)methyl]-3-(dimethylamino)cyclopentanecarboxamide |
| IV-500 | 4-({9-Chloro-7-[2-fluoro-6-(trifluoromethyl)phenyl]-5H-pyrimido-[5,4-d][2]benzazepin-2-yl}amino)benzoic acid |
| IV-501 | 4-{[9-Chloro-7-(2,6-dichlorophenyl)-5H>-pyrimido[5,4-d][2]benzazepin-2-yl]amino}benzoic acid |
| IV-502 | 4-{[9-Chloro-7-(2-fluoro-6-methylphenyl)-5H-pyrimido[5,4-d][2]benzazepin-2-yl]amino}benzoic acid |
| IV-503 | 4-{[7-(2-Bromo-6-chlorophenyl)-9-chloro-5H-pyrimido[5,4-d][2]benzazepin-2-yl]amino}benzoic acid |
| IV-504 | 9-Chloro-7-(2,6-difluorophenyl)-N-{4-[(3,5-dimethylpiperazin-1-yl)carbonyl]-3-fluorophenyl}-5H-pyrimido[5,4-d][2]benzazepin-2-amine |
| IV-505 | 4-{[9-Chloro-7-(2,6-difluorophenyl)-5H-pyrimido[5,4-d][2]benzazepin-2-yl]amino}-N-[(3,5-dimethylpiperazin-1-yl)(imino)methyl]-N-methylbenzamide |
| IV-506 | 4-{[9-Chloro-7-(2,6-difluorophenyl)-5H-pyrimido[5,4-d][2]benzazepin-2-yl]amino}-N-[[3-(dimethylamino)azetidin-1-yl](imino)methyl]-N-methylbenzamide |
| IV-507 | 3-{[9-Chloro-7-(2,6-difluorophenyl)-5H-pyrimido[5,4-d][2]benzazepin-2-yl]amino}-N-[(3,5-dimethylpiperazin-1-yl)(imino)methyl]benzamide |
| IV-508 | 3-{[9-Chloro-7-(2,6-difluorophenyl)-5H-pyrimido[5,4-d][2]benzazepin-2-yl]amino}-N-[[3-(dimethylamino)pyrrolidin-1-yl](imino)methyl]benzamide |
| IV-509 | 9-Chloro-7-(2,6-difluorophenyl)-N-{3-[(3,5-dimethylpiperazin-1-yl)carbonyl]-4-fluorophenyl}-5H-pyrimido[5,4-d][2]benzazepin-2-amine |
| IV-510 | N-[[(4-{[9-Chloro-7-(2,6-difluorophenyl)-5H-pyrimido[5,4-d][2]benzazepin-2-yl]amino}phenyl)amino](imino)methyl]-3-(dimethylamino)cyclopentanecarboxamide |
| IV-511 | N-[[(4-{[9-Chloro-7-(2,6-difluorophenyl)-5H-pyrimido[5,4-d][2]benzazepin-2-yl]amino}-2-fluorophenyl)amino](imino)methyl]-3-(dimethylamino)cyclopentanecarboxamide |
| IV-512 | N-[[(5-{[9-Chloro-7-(2,6-difluorophenyl)-5H-pyrimido[5,4-d][2]benzazepin-2-yl]amino}-2-fluorophenyl)amino](imino)methyl]-3-(dimethylamino)cyclopentanecarboxamide |
| IV-513 | N-(4-{[9-Chloro-7-(2,6-difluorophenyl)-5H-pyrimido[5,4-d][2]benzazepin-2-yl]amino}phenyl)-3,5-dimethylpiperazine-1-carboximidamide |
| IV-514 | 4-{[9-Chloro-7-(2,6-difluorophenyl)-5H-pyrimido[5,4-d][2]benzazepin-2-yl]amino}-N-[[3-(dimethylamino)pyrrolidin-1-yl](imino)methyl]-N-methylbenzamide |
| IV-515 | N-(3-{[9-Chloro-7-(2,6-difluorophenyl)-5H-pyrimido[5,4-d][2]benzazepin-2-yl]amino}phenyl)-3,5-dimethylpiperazine-1-carboximidamide |
| IV-516 | N-(3-{[9-Chloro-7-(2,6-difluorophenyl)-5H-pyrimido[5,4-d][2]benzazepin-2-yl]amino}phenyl)-N,3,5-trimethylpiperazine-1-carboximidamide |
| IV-517 | 3-{[9-Chloro-7-(2,6-difluorophenyl)-5H-pyrimido[5,4-d][2]benzazepin-2-yl]amino}-N-[[3-(dimethylamino)azetidin-1-yl](imino)methyl]benzamide |
| IV-518 | N-(5-{[9-Chloro-7-(2,6-difluorophenyl)-5H-pyrimido[5,4-d][2]benzazepin-2-yl]amino}-2-fluorophenyl)-N,3,5-trimethylpiperazine-1-carboximidamide |
| IV-519 | N-[[(3-{[9-Chloro-7-(2,6-difluorophenyl)-5H-pyrimido[5,4-d][2]benzazepin-2-yl]amino}phenyl)amino](imino)methyl]-3-(dimethylamino)cyclopentanecarboxamide |
| IV-520 | 9-Chloro-7-(2,6-difluorophenyl)-N-{3-[(3,5-dimethylpiperazin-1-yl)(imino)methyl]phenyl}-5H-pyrimido[5,4-d][2]benzazepin-2-amine |
| IV-521 | N-(4-{[9-Chloro-7-(2,6-difluorophenyl)-5H-pyrimido[5,4-d][2]benzazepin-2-yl]amino}phenyl)-N,3,5-trimethylpiperazine-1-carboximidamide |
| IV-522 | N-(4-{[9-Chloro-7-(2,6-difluorophenyl)-5H-pyrimido[5,4-d][2]benzazepin-2-yl]amino}-2-fluorophenyl)-3,5-dimethylpiperazine-1-carboximidamide |
| IV-523 | 9-Chloro-7-(2,6-difluorophenyl)-N-{4-[(3,5-dimethylpiperazin-1-yl)(imino)methyl]-3-fluorophenyl}-5H-pyrimido[5,4-d][2]benzazepin-2-amine |
| IV-524 | 5-{[9-Chloro-7-(2,6-difluorophenyl)-5H-pyrimido[5,4-d][2]benzazepin-2-yl]amino}-2-(2,6-dimethylpiperidin-4-yl)-1H-isoindole-1,3(2H)-dione |
| IV-525 | N-[2-(Aminomethyl)-1H-benzimidazol-6-yl]-9-chloro-7-(2-fluorophenyl)-5H-pyrimido[5,4-d][2]benzazepin-2-amine |
| IV-526 | 9-Chloro-7-(2-fluorophenyl)-N-{2-[(methylamino)methyl]-1H-benzimidazol-6-yl}-5H-pyrimido[5,4-d][2]benzazepin-2-amine |
| IV-527 | 9-Chloro-N-{2-[(dimethylamino)methyl]-1H-benzimidazol-6-yl}-7-(2-fluorophenyl)-5H-pyrimido[5,4-d][2]benzazepin-2-amine |
| IV-528 | 9-Chloro-7-(2-fluorophenyl)-N-{2-[(methylamino)methyl]-1,3-benzothiazol-6-yl}-5H-pyrimido[5,4-d][2]benzazepin-2-amine |
| IV-529 | 9-Chloro-7-(2,6-difluorophenyl)-N-{2-[(methylamino)methyl]-1H-benzimidazol-6-yl}-5H-pyrimido[5,4-d][2]benzazepin-2-amine |
| IV-530 | 9-Chloro-7-(2,6-difluorophenyl)-N-{2-[(methylamino)methyl]-1,3-benzoxazol-6-yl}-5H-pyrimido[5,4-d][2]benzazepin-2-amine |
| IV-531 | 9-Chloro-7-(2-fluorophenyl)-N-{2-[(methylamino)methyl]-1,3-benzoxazol-6-yl}-5H-pyrimido[5,4-d][2]benzazepin-2-amine |

TABLE 2-continued

Examples of Compounds of Formula (IV)

| | |
|---|---|
| IV-532 | 9-Chloro-7-(2,6-difluorophenyl)-N-{3-[(3,5-dimethylpiperazin-1-yl)(imino)methyl]-4-fluorophenyl}-5H-pyrimido[5,4-d][2]benzazepin-2-amine |
| IV-533 | 9-Chloro-7-(2,6-difluorophenyl)-N-{2-[(methylamino)methyl]-1,3-benzothiazol-6-yl}-5H-pyrimido[5,4-d][2]benzazepin-2-amine |
| IV-534 | {3-[9-Chloro-7-(2,6-difluorophenyl)-5H-benzo[c]pyrimido[4,5-e]azepin-2-ylamino]-phenyl}-(4-methyl-piperazin-1-yl)-methanone |
| IV-535 | 3-[9-Chloro-7-(2,6-difluoro-phenyl)-5H-benzo[c]pyrimido[4,5-e]azepin-2-ylamino]-N-methyl-N-(4-methyl-pentyl)-benzamide |

In some embodiments, the selective Aurora A kinase inhibitor is represented by formula (V):

(V)

or a pharmaceutically acceptable salt thereof;
wherein:
$R^a$ is selected from the group consisting of $C_{1-3}$ aliphatic, $C_{1-3}$ fluoroaliphatic, —$R^1$, -T-$R^1$, —$R^2$, and -T-$R^2$;
T is a $C_{1-3}$ alkylene chain optionally substituted with fluoro;
$R^1$ is an optionally substituted aryl, heteroaryl, or heterocyclyl group;
$R^2$ is selected from the group consisting of halo, —C≡C—$R^3$, —CH═CH—$R^3$, —N($R^4$)$_2$, and —O$R^5$;
$R^3$ is hydrogen or an optionally substituted aliphatic, aryl, heteroaryl, or heterocyclyl group;
each $R^4$ independently is hydrogen or an optionally substituted aliphatic, aryl, heteroaryl, or heterocyclyl group; or two $R^4$ on the same nitrogen atom, taken together with the nitrogen atom form an optionally substituted 5- to 6-membered heteroaryl or 4- to 8-membered heterocyclyl ring having, in addition to the nitrogen atom, 0-2 ring heteroatoms selected from N, O, and S;
$R^5$ is hydrogen or an optionally substituted aliphatic, aryl, heteroaryl, or heterocyclyl group; and
$R^b$ is selected from the group consisting of fluoro, chloro, —$CH_3$, —$CF_3$, —OH, —$OCH_3$, —$OCF_3$, —$OCH_2CH_3$, and —$OCH_2CF_3$.

In some embodiments, $R^1$ is a 5- or 6-membered aryl, heteroaryl, or heterocyclyl ring optionally substituted with one or two substituents independently selected from the group consisting of halo, $C_{1-3}$ aliphatic, and $C_{1-3}$-fluoroaliphatic. In certain embodiments, $R^1$ is a phenyl, furyl, pyrrolidinyl, or thienyl ring optionally substituted with one or two substituents independently selected from the group consisting of halo, $C_{1-3}$ aliphatic, and $C_{1-3}$-fluoroaliphatic.

In some embodiments, $R^3$ is hydrogen, $C_{1-3}$ aliphatic, $C_{1-3}$ fluoroaliphatic, or —$CH_2$—$OCH_3$.

In some embodiments, $R^5$ is hydrogen, $C_{1-3}$ aliphatic, or $C_{1-3}$ fluoroaliphatic.

In certain embodiments, $R^a$ is halo, $C_{1-3}$ aliphatic, $C_{1-3}$ fluoroaliphatic, —OH, —O($C_{1-3}$ aliphatic), —O($C_{1-3}$ fluoroaliphatic), —C≡C—$R^3$, —CH═CH—$R^3$, or an optionally substituted pyrrolidinyl, thienyl, furyl, or phenyl ring, wherein $R^3$ is hydrogen, $Cl_3$ aliphatic, $C_{1-3}$ fluoroaliphatic, or —$CH_2$—$OCH_3$. In certain particular embodiments, $R^a$ is selected from the group consisting of chloro, fluoro, $C_{1-3}$ aliphatic, $C_{1-3}$ fluoroaliphatic, —$OCH_3$, —$OCF_3$, —C≡C—H, —C≡C—$CH_3$, —C≡C—$CH_2OCH_3$, —CH═$CH_2$, —CH═$CHCH_3$, N-methylpyrrolidinyl, thienyl, methylthienyl, furyl, methylfuryl, phenyl, fluorophenyl, and tolyl. In certain embodiments, $R^a$ is a phenyl, furyl, pyrrolidinyl, or thienyl ring optionally substituted with one or two substituents independently selected from the group consisting of halo, $C_{1-3}$ aliphatic, and $C_{1-3}$ fluoroaliphatic.

Table 3 provides the chemical names for specific examples of compounds of formula (V).

TABLE 3

Examples of Compounds of Formula (V)

| | Chemical Name |
|---|---|
| V-1 | 4-{[9-chloro-7-(2-fluoro-6-methoxyphenyl)-5H-pyrimido[5,4-d][2]benzazepin-2-yl]amino}-2-methoxybenzoic acid |
| V-2 | 4-{[9-ethynyl-7-(2-fluoro-6-methoxyphenyl)-5H-pyrimido[5,4-d][2]benzazepin-2-yl]amino}-2-methoxybenzoic acid |
| V-3 | 4-({9-chloro-7-[2-fluoro-6-(trifluoromethoxy)phenyl]-5H-pyrimido[5,4-d][2]benzazepin-2-yl}amino)-2-methoxybenzoic acid |
| V-4 | 4-{[7-(2-fluoro-6-methoxyphenyl)-9-(1-methyl-1H-pyrrol-2-yl)-5H-pyrimido[5,4-d][2]benzazepin-2-yl]amino}-2-methoxybenzoic acid |

TABLE 3-continued

Examples of Compounds of Formula (V)

| | Chemical Name |
|---|---|
| V-5 | 4-{[7-(2-fluoro-6-methoxyphenyl)-9-(4-methyl-3-thienyl)-5H-pyrimido[5,4-d][2]benzazepin-2-yl]amino}-2-methoxybenzoic acid |
| V-6 | 4-{[7-(2-fluoro-6-methoxyphenyl)-9-(3-methyl-2-furyl)-5H-pyrimido[5,4-d][2]benzazepin-2-yl]amino}-2-methoxybenzoic acid |
| V-7 | 4-({9-ethynyl-7-[2-fluoro-6-(2,2,2-trifluoroethoxy)phenyl]-5H-pyrimido[5,4-d][2]benzazepin-2-yl}amino)-2-methoxybenzoic acid |
| V-8 | 4-{[9-chloro-7-(2,6-difluorophenyl)-5H-pyrimido[5,4-d][2]benzazepin-2-yl]amino}-2-methoxybenzoic acid |
| V-9 | 4-{[7-(2-fluoro-6-methoxyphenyl)-9-(2-methylphenyl)-5H-pyrimido[5,4-d][2]benzazepin-2-yl]amino}-2-methoxybenzoic acid |
| V-10 | 4-{[7-(2-fluoro-6-methoxyphenyl)-9-prop-1-yn-1-yl-5H-pyrimido[5,4-d][2]benzazepin-2-yl]amino}-2-methoxybenzoic acid |
| V-11 | 4-{[7-(2-fluoro-6-methoxyphenyl)-9-vinyl-5H-pyrimido[5,4-d][2]benzazepin-2-yl]amino}-2-methoxybenzoic acid |
| V-12 | 4-{[7-(2-fluoro-6-methoxyphenyl)-9-(2-fluorophenyl)-5H-pyrimido[5,4-d][2]benzazepin-2-yl]amino}-2-methoxybenzoic acid |
| V-13 | 4-{[7-(2-fluoro-6-methoxyphenyl)-9-(3-methoxyprop-1-yn-1-yl)-5H-pyrimido[5,4-d][2]benzazepin-2-yl]amino}-2-methoxybenzoic acid |
| V-14 | 4-({7-(2-fluoro-6-methoxyphenyl)-9-[(1E)-prop-1-en-1-yl]-5H-pyrimido[5,4-d][2]benzazepin-2-yl}amino)-2-methoxybenzoic acid |
| V-15 | 4-({9-chloro-7-[2-fluoro-6-(2,2,2-trifluoroethoxy)phenyl]-5H-pyrimido[5,4-d][2]benzazepin-2-yl}amino)-2-methoxybenzoic acid |
| V-16 | 4-{[7-(2-fluoro-6-methoxyphenyl)-9-(2-furyl)-5H-pyrimido[5,4-d][2]benzazepin-2-yl]amino}-2-methoxybenzoic acid |
| V-17 | 4-{[9-chloro-7-(2-fluoro-6-hydroxyphenyl)-5H-pyrimido[5,4-d][2]benzazepin-2-yl]amino}-2-methoxybenzoic acid |
| V-18 | 4-{[7-(2-fluoro-6-methoxyphenyl)-9-phenyl-5H-pyrimido[5,4-d][2]benzazepin-2-yl]amino}-2-methoxybenzoic acid |

In one embodiment, the compound of formula (III), (IV), or (V) is 4-{[9-chloro-7-(2-fluoro-6-methoxyphenyl)-5H-pyrimido[5,4-d][2]benzazepin-2-yl]amino}-2-methoxybenzoic acid (alisertib (MLN8237)), or a pharmaceutically acceptable salt thereof. In a particular embodiment, the compound of formula (III), (IV), or (V) is sodium 4-{[9-chloro-7-(2-fluoro-6-methoxyphenyl)-5H-pyrimido[5,4-d][2]benzazepin-2-yl]amino}-2-methoxybenzoate. In another embodiment, the compound of formula (III), (IV), or (V) is sodium 4-{[9-chloro-7-(2-fluoro-6-methoxyphenyl)-5H-pyrimido[5,4-d][2]benzazepin-2-yl]amino}-2-methoxybenzoate monohydrate. In another embodiment, the compound of formula (III), (IV), or (V) is sodium 4-{[9-chloro-7-(2-fluoro-6-methoxyphenyl)-5H-pyrimido[5,4-d][2]benzazepin-2-yl]amino}-2-methoxybenzoate polymorph Form 2, as described in US Publication No. 2008/0167292, U.S. Pat. No. 8,026,246, and US Publication No. 2011/0245234, hereby incorporated by reference in their entirety.

In another aspect, the invention provides a method for inhibiting cellular growth/cellular proliferation comprising contacting a cell with a MEK inhibitor (as described herein) in combination with a selective inhibitor of Aurora A kinase (as described herein). In one embodiment, the invention provides a method for inhibiting cellular growth/cellular proliferation comprising contacting a cell with a MEK inhibitor in combination with a selective inhibitor of Aurora A kinase, e.g., sodium 4-{[9-chloro-7-(2-fluoro-6-methoxyphenyl)-5H-pyrimido[5,4-d][2]benzazepin-2-yl]amino}-2-methoxybenzoate. In an another embodiment, the invention provides a method for inhibiting cellular growth/cellular proliferation comprising contacting a cell with a MEK inhibitor, e.g., 3-[(2R)-2,3-dihydroxypropyl]-6-fluoro-5-[(2-fluoro-4-iodophenyl)amino]-8-methylpyrido[2,3-d]pyrimidine-4,7(3H,8H)-dione, or a pharmaceutically acceptable salt thereof, in combination with a selective inhibitor of Aurora A kinase.

Preferably, the method according to the invention causes an inhibition of cell proliferation of the contacted cells. The phrase "inhibiting cell proliferation" is used to denote an ability of a MEK inhibitor and/or a selective inhibitor of Aurora A kinase to inhibit cell number or cell growth in contacted cells as compared to cells not contacted with the inhibitors. An assessment of cell proliferation can be made by counting cells using a cell counter or by an assay of cell viability, e.g., a BrdU, MTT, XTT, or WST assay. Where the cells are in a solid growth (e.g., a solid tumor or organ), such an assessment of cell proliferation can be made by measuring the growth, e.g., with calipers, and comparing the size of the growth of contacted cells with non-contacted cells.

Preferably, the growth of cells contacted with a MEK inhibitor and a selective inhibitor of Aurora A kinase is retarded by at least about 50% as compared to growth of non-contacted cells. In various embodiments, cell proliferation of contacted cells is inhibited by at least about 75%, at least about 90%, or at least about 95% as compared to non-contacted cells. In some embodiments, the phrase "inhibiting cell proliferation" includes a reduction in the number of contacted cells, as compare to non-contacted cells. Thus, a MEK inhibitor and/or a selective inhibitor of Aurora A kinase that inhibits cell proliferation in a contacted cell may induce the contacted cell to undergo growth retardation, to undergo growth arrest, to undergo programmed cell death (i.e., apoptosis), or to undergo necrotic cell death.

In another aspect, the invention provides a pharmaceutical composition comprising i) a MEK inhibitor (as described herein); and ii) a selective inhibitor of Aurora A kinase (as described herein). In some embodiments, the MEK inhibitor is selected from the group consisting of a) the compounds of formulas (I), (II), and (IA); b) the compounds disclosed in, for example, WO 08/079,814, WO 10/059,503, and U.S. Application No. 61/477,196, filed Apr. 20, 2011, hereby incorporated by reference in their entirety, 3-[(2R)-2,3- dihydroxypropyl]-6-fluoro-5-[(2-fluoro-4-iodophenyl)amino]-8-methylpyrido[2,3-d]pyrimidine-4,7(3H,8H)-dione, PD98059, U0126, Ro 09-2210, CI-1040 (Pfizer—formerly PD 184352), PD0325901 (Pfizer), AZD6244 (Array BioPharma/AstraZeneca—formerly ARRY-142886), GDC-0973 (Exelixis/Genentech—formerly XL518), AR-119/RDEA119 (Ardea Biosciences/Bayer—formerly BAY 869766), GSK1120212 (GlaxoSmithKline), AZD8330 (Array BioPharma/AstraZeneca), RO5126766, RO4987655, RO4927350, RO5068760 (Hoffmann La Roche), AS703026, AS-701173, and AS-701255 (EMD Serono); and c) pharmaceutically acceptable salts thereof. In some embodiments the selective inhibitor of Aurora A kinase is selected from the group consisting of a) the compounds of formulas (II), (IV), and (V); b) the compounds disclosed in, for example, US Publication No. 2008/0045501, U.S. Pat. No. 7,572,784, WO 05/111039, WO 08/021,038, U.S. Pat. No. 7,718,648, WO 08/063,525, US Publication No. 2008/0167292, U.S. Pat. No. 8,026,246, WO 10/134,965, US Publication No. 2010/0310651, WO 11/014,248, US Publication No. 2011/0039826, and US Publication No. 2011/0245234; c) sodium 4-{[9-chloro-7-(2-fluoro-6-methoxyphenyl)-5H-pyrimido[5,4-d][2]benzazepin-2-yl]amino}-2-methoxybenzoate, KW-2449 (Kyowa), ENMD-2076 (EntreMed), and MK-5108 (Vertex/Merck); and d) pharmaceutically acceptable salts of any of the foregoing.

If a pharmaceutically acceptable salt of the MEK inhibitor or selective inhibitor of Aurora A kinase is utilized in these compositions, the salt preferably is derived from an inorganic or organic acid or base. For reviews of suitable salts, see, e.g., Berge et al, *J. Pharm. Sci.* 66:1-19 (1977) and *Remington: The Science and Practice of Pharmacy*, 20th Ed., ed. A. Gennaro, Lippincott Williams & Wilkins, 2000.

Nonlimiting examples of suitable acid addition salts include the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate.

Suitable base addition salts include, without limitation, ammonium salts, alkali metal salts, such as sodium and potassium salts, alkaline earth metal salts, such as calcium and magnesium salts, salts with organic bases, such as dicyclohexylamine, N-methyl-D-glucamine, t-butylamine, ethylene diamine, ethanolamine, and choline, and salts with amino acids such as arginine, lysine, and so forth.

Also, basic nitrogen-containing groups may be quaternized with such agents as lower alkyl halides, such as methyl, ethyl, propyl, and butyl chlorides, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The term "pharmaceutically acceptable carrier" is used herein to refer to a material that is compatible with a recipient subject, preferably a mammal, more preferably a human, and is suitable for delivering an active agent to the target site without terminating the activity of the agent. The toxicity or adverse effects, if any, associated with the carrier preferably are commensurate with a reasonable risk/benefit ratio for the intended use of the active agent.

The terms "carrier", "adjuvant", or "vehicle" are used interchangeably herein, and include any and all solvents, diluents, and other liquid vehicles, dispersion or suspension aids, surface active agents, isotonic agents, thickening or emulsifying agents, preservatives, solid binders, lubricants and the like, as suited to the particular dosage form desired. *Remington: The Science and Practice of Pharmacy*, 20th Ed., ed. A. Gennaro, Lippincott Williams & Wilkins, 2000 discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as disodium hydrogen phosphate, potassium hydrogen phosphate, sodium carbonate, sodium bicarbonate, potassium carbonate, potassium bicarbonate, magnesium hydroxide and aluminum hydroxide, glycine, sorbic acid, or potassium sorbate, partial glyceride mixtures of saturated vegetable fatty acids, water, pyrogen-free water, salts or electrolytes such as protamine sulfate, disodium hydrogen phosphate, potassium hydrogen phosphate, sodium chloride, and zinc salts, colloidal silica, magnesium trisilicate, polyvinyl pyrrolidone, polyacrylates, waxes, polyethylene-polyoxypropylene-block polymers, wool fat, sugars such as lactose, glucose, sucrose, starches such as corn starch and potato starch, cellulose and its derivatives such as sodium carboxymethyl cellulose, ethyl cellulose and cellulose acetate, powdered tragacanth; malt, gelatin, talc, excipients such as cocoa butter and suppository waxes, oils such as peanut oil, cottonseed oil, safflower oil, sesame oil, olive oil, corn oil and soybean oil, glycols such as propylene glycol and polyethylene glycol, esters such as ethyl oleate and ethyl laurate, agar, alginic acid, isotonic saline, Ringer's solution, alcohols such as ethanol, isopropyl alcohol, hexadecyl alcohol, and glycerol, cyclodextrins, lubricants such as sodium lauryl sulfate and magnesium stearate, petroleum hydrocarbons such as mineral oil and petrolatum. Coloring agents, releasing agents, coating agents, sweetening, flavoring and perfuming agents, preservatives and antioxidants can also be present in the composition, according to the judgment of the formulator.

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain solvents, diluents, and other liquid vehicles, dispersion or suspension aids, surface active agents, pH modifiers, isotonic agents, thickening or emulsifying agents, stabilizers and preservatives, solid binders, lubricants and the like, as suited to the particular dosage form desired.

According to a preferred embodiment, the compositions of this invention are formulated for pharmaceutical administration to a mammal, preferably a human being. Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intravenously, or subcutaneously. The formulations of the invention may be designed to be short-acting, fast-releasing, or long-acting. Still further, compounds can be administered in a local rather than systemic means, such as administration (e.g., by injection) at a tumor site.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, cyclodextrins, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. Compositions formulated for parenteral administration may be injected by bolus injection or by timed push, or may be administered by continuous infusion.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffinin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents such as phosphates or carbonates.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The present invention provides new combination therapies for the treatment of cell proliferative disorders. As used herein, the terms "proliferative disorders" or "proliferative diseases" includes, but is not limited to, cancerous hyperproliferative disorders (e.g., brain, lung, squamous cell, bladder, gastric, pancreatic, breast, head and neck, squamous cell carcinoma of the head and neck, renal (e.g., metastatic renal cell carcinoma), liver, kidney, ovarian (e.g., progressive epithelial or primary peritoneal cancer), prostate (e.g., androgen-dependent and androgen-independent prostate cancer), colorectal, colon, hepatocellular carcinoma, epidermoid, esophageal, testicular, gynecological or thyroid cancer, cervical cancer, acute myeloid leukemia, multiple myeloma, mesothelioma, Non-small cell lung carcinoma (NSCLC), Small cell lung carcinoma (SCLC), bronchioloalveolar carcinoma (BAC), and adenocarcinoma of the lung, neuroendocrine (e.g., including metastatic neuroendocrine tumors), neuroblastoma, chronic lymphocytic leukemia (CLL), acute myeloid leukemia (AML), chronic myelogenous leukemia (CML), including accelerated CML and CML blast phase (CML-BP), acute lymphoblastic leukemia (ALL), Hodgkin's disease (HD), non-Hodgkin's lymphoma (NHL), including follicular lymphoma and mantle cell lymphoma, B-cell lymphoma, T-cell lymphoma, Burkitt's lymphoma, multiple myeloma (MM), Waldenstrom's macroglobulinemia, myelodysplastic syndromes (MDS), including refractory anemia (RA), refractory anemia with ringed sideroblasts (RARS), (refractory anemia with excess blasts (RAEB), and RAEB in transformation (RAEB-T), and myeloproliferative syndromes); non-cancerous hyperproliferative disorders (e.g., benign hyperplasia of the skin (e.g., psoriasis), restenosis, and benign prostatic hypertrophy (BPH)); and diseases related to vasculogenesis or angiogenesis (e.g., tumor angiogenesis, hemangioma, glioma, melanoma, nasopharyngeal carcinoma, pediatric sarcomas, soft tissue sarcoma, bone cancer, Kaposi's sarcoma and ovarian, breast, lung, pancreatic, prostate, colon and epidermoid cancer). These "proliferative disorders" and "proliferative diseases" encompass both primary and metastatic or advanced cancers, including intransient metasteses. In one embodiment, the cancer is metastatic. In another embodiment, proliferative disorders or diseases treatable by the combination of an Aurora A kinase selective inhibitor and a MEK inhibitor include ovarian, Head and neck, breast, colorectal, NSCLC, SCLC, gastric, pancreatic, prostate, Non Hodgkin's lymphoma, including follicular, mantle cell, DLBCL, PTCL, and Burkitt's lymphoma, neruoblastoma, AML, hepatocelullar carcinoma, nasopharyngeal carcinoma, pediatric sarcomas, glioma, multiple myeloma, Waldenstrom's macroglobenemia, and melanoma. In a further preferred embodiment, diseases or disorders treatable by the combination of an Aurora A kinase selective inhibitor and a MEK inhibitor include lung cancer, ovarian cancer, prostate cancer, melanoma, colorectal cancer, and pancreatic cancer. In a further preferred embodiment, diseases or disorders treatable by the combination of an Aurora A kinase selective inhibitor and a MEK inhibitor include gastric cancer, head and neck squamous cell carcinoma, small cell lung cancer, melanoma, and colorectal cancer The term "patient", as used herein, means an animal, preferably a mammal, more preferably a human. In some embodiments, the patient has been treated with an agent, e.g., an Aurora A kinase selective inhibitor or a MEK inhibitor, prior to initiation of treatment according to the method of the invention. In some embodiments, the patient is a patient at risk of developing or experiencing a recurrence of a proliferative disorder.

The expressions "therapeutically effective" and "therapeutic effect" refer to a benefit including, but not limited to, the treatment or prophylaxis or amelioration of symptoms of a proliferative disorder discussed herein. It will be appreciated that the therapeutically effective amount or the amount of agent required to provide a therapeutic effect will vary depending upon the intended application (in vitro or in vivo), or the subject and disease condition being treated (e.g., nature of the severity of the condition to be treated, the particular inhibitor, the route of administration and the age, weight, general health, and response of the individual patient), which can be readily determined by a person of skill in the art. For example, an amount of a selective inhibitor of Aurora A kinase in combination with an amount of a MEK inhibitor is therapeutically effective if it is sufficient to effect the treatment or prophylaxis or amelioration of symptoms of a proliferative disorder discussed herein.

Compositions for use in the method of the invention may be formulated in unit dosage form for ease of administration and uniformity of dosage. The expression "unit dosage form" as used herein refers to a physically discrete unit of agent appropriate for the patient to be treated. It will be understood, however, that the total daily usage of the compounds and compositions of the present invention will be decided by the attending physician within the scope of sound medical judgment. A unit dosage form for parenteral administration may be in ampoules or in multi-dose containers.

The MEK inhibitor may be administered with the selective inhibitor of Aurora A kinase in a single dosage form or as a separate dosage form. In one embodiment, when administered as a separate dosage form, the MEK inhibitor may be administered prior to, at the same time as, or following administration of the selective inhibitor of Aurora A kinase of the invention. In another embodiment, when administered as a separate dosage form, one or more doses of the MEK inhibitor may be administered prior to the selective inhibitor of Aurora A kinase of the invention.

In another embodiment, when administered as a separate dosage form, one or more doses of the selective inhibitor of Aurora A kinase may be administered prior to the MEK inhibitor of the invention.

In some particular embodiments, the method of the invention comprises administering to a patient suffering from a proliferative disorder a MEK inhibitor of Formula (I), (II), or (IIA), as defined herein, in combination with a selective inhibitor of Aurora A kinase of Formula (III), (IV) or (V), as defined herein, wherein the amounts of each inhibitor are therapeutically effective when used in combination.

In another embodiment, the method of the invention comprises administering to a patient suffering from a proliferative disorder 3-[(2R)-2,3-dihydroxypropyl]-6-fluoro-5-[(2-fluoro-4-iodophenyl)amino]-8-methylpyrido[2,3-d]pyrimidine-4,7(3H,8H)-dione, in combination with a selective inhibitor of Aurora A kinase of Formula (III), (IV) or (V), as defined herein, wherein the amounts of each inhibitor are therapeutically effective when used in combination.

In another embodiment, the method of the invention comprises administering to a patient suffering from a proliferative disorder a MEK inhibitor of Formula (I), (II), or (IIA), as defined herein, in combination with sodium 4-{[9-chloro-7-(2-fluoro-6-methoxyphenyl)-5H-pyrimido[5,4-d][2]benzazepin-2-yl]amino}-2-methoxybenzoate, wherein the amounts of each inhibitor are therapeutically effective when used in combination.

In another embodiment, the method of the invention comprises administering to a patient suffering from a proliferative disorder 3-[(2R)-2,3-dihydroxypropyl]-6-fluoro-5-[(2-fluoro-4-iodophenyl)amino]-8-methylpyrido[2,3-d]pyrimidine-4,7(3H,8H)-dione, in combination with sodium 4-{[9-chloro-7-(2-fluoro-6-methoxyphenyl)-5H-pyrimido[5,4-d][2]benzazepin-2-yl]amino}-2-methoxybenzoate, wherein the amounts of each inhibitor are therapeutically effective when used in combination.

Additionally, the invention relates to use of a MEK inhibitor in the manufacture of a medicament for use in combination therapy with a selective inhibitor of Aurora A kinase for the treatment of a proliferative disorder. In other particular embodiments, the invention relates to the use of a MEK inhibitor of Formula (I), (II), or (IIA) (as defined herein), in the manufacture of a medicament for use in combination therapy with a selective inhibitor of Aurora A kinase of Formula (III), (IV) or (V) (as defined herein), for the treatment of a proliferative disorder.

In another embodiment, the invention relates to the use of 3-[(2R)-2,3-dihydroxypropyl]-6-fluoro-5-[(2-fluoro-4-iodophenyl)amino]-8-methylpyrido[2,3-d]pyrimidine-4,7(3H,8H)-dione, in the manufacture of a medicament for use in combination therapy with a selective inhibitor of Aurora A kinase of Formula (III), (IV) or (V) (as defined herein), for the treatment of a proliferative disorder.

In another embodiment, the invention relates to the use of a MEK inhibitor of Formula (I), (II), or (IIA) (as defined herein), in the manufacture of a medicament for use in combination therapy with sodium 4-{[9-chloro-7-(2-fluoro-6-methoxyphenyl)-5H-pyrimido[5,4-d][2]benzazepin-2-yl]amino}-2-methoxybenzoate, as defined herein, for the treatment of a proliferative disorder.

In another embodiment, the invention relates to the use of 3-[(2R)-2,3-dihydroxypropyl]-6-fluoro-5-[(2-fluoro-4-iodophenyl)amino]-8-methylpyrido[2,3-d]pyrimidine-4,7(3H,8H)-dione, in the manufacture of a medicament for use in combination therapy with sodium 4-{[9-chloro-7-(2-fluoro-6-methoxyphenyl)-5H-pyrimido[5,4-d][2]benzazepin-2-yl]amino}-2-methoxybenzoate for the treatment of a proliferative disorder.

As specifically contemplated herein, the instant invention includes the following methods:

a. A method to treat a patient suffering from a proliferative disorder comprising administering to said patient a MEK inhibitor, as defined herein, in combination with a selective inhibitor of Aurora A kinase, as defined herein, wherein the amounts of each inhibitor are therapeutically effective when used in combination. In some embodiments, the proliferative disorder is selected from the group consisting of gastric cancer, head and neck squamous cell carcinoma, small cell lung cancer, melanoma, and colorectal cancer. In one embodiment, the proliferative disorder is gastric cancer. In another embodiment, the proliferative disorder is head and neck squamous cell carcinoma. In another embodiment, the proliferative disorder is small cell lung cancer. In another embodiment, the proliferative disorder is colorectal cancer. In another embodiment, the proliferative disorder is melanoma. In another embodiment, the proliferative disorder is ovarian cancer.

b. A method to treat a patient suffering from a proliferative disorder comprising administering to said patient 3-[(2R)-2,3-dihydroxypropyl]-6-fluoro-5-[(2-fluoro-4-iodophenyl)amino]-8-methylpyrido[2,3-d]pyrimidine-4,7(3H,8H)-dione, or a pharmaceutically acceptable salt thereof, in combination with a selective inhibitor of Aurora A kinase, as defined herein, wherein the amounts of each inhibitor are therapeutically effective when used in combination. In some embodiments, the proliferative disorder is selected from the group consisting of gastric cancer, head and neck squamous cell carcinoma, small cell lung cancer, melanoma, and colorectal cancer. In one embodiment, the proliferative disorder is gastric cancer. In another embodiment, the proliferative disorder is head and neck squamous cell carcinoma. In another embodiment, the proliferative disorder is small cell lung cancer. In another embodiment, the proliferative disorder is colorectal cancer. In another embodiment, the proliferative disorder is melanoma. In another embodiment, the proliferative disorder is ovarian cancer.

c. A method to treat a patient suffering from a proliferative disorder comprising administering to said patient a MEK inhibitor, as defined herein, in combination with sodium 4-{[9-chloro-7-(2-fluoro-6-methoxyphenyl)-5H-pyrimido[5,4-d][2]benzazepin-2-yl]amino}-2-methoxybenzoate, wherein the amounts of each inhibitor are therapeutically effective when used in combination. In some embodiments, the proliferative disorder is selected from the group consisting of gastric cancer, head and neck squamous cell carcinoma, small cell lung cancer, melanoma, and colorectal cancer In one embodiment, the proliferative disorder is gastric cancer. In another embodiment, the proliferative disorder is head and neck squamous cell carcinoma. In another embodiment, the proliferative disorder is small cell lung cancer. In another embodiment, the proliferative disorder is colorectal cancer. In another embodiment, the proliferative disorder is melanoma. In another embodiment, the proliferative disorder is ovarian cancer.

d. A method to treat a patient suffering from a proliferative disorder comprising administering to said patient sodium 4-{[9-chloro-7-(2-fluoro-6-methoxyphenyl)-5H-pyrimido[5,4-d][2]benzazepin-2-yl]amino}-2-methoxybenzoate in combination with 3-[(2R)-2,3-dihydroxypropyl]-6-fluoro-5-[(2-fluoro-4-iodophenyl)amino]-8-methylpyrido[2,3-d]pyrimidine-4,7(3H,8H)-dione, or a pharmaceutically acceptable salt thereof, wherein the amounts of each inhibitor are therapeutically effective when used in combination. In some embodiments, the proliferative disorder is selected from the group consisting of gastric cancer, head and neck squamous cell carcinoma, small cell lung cancer, melanoma, and colorectal cancer In one embodiment, the proliferative disorder is gastric cancer. In another embodiment, the proliferative disorder is head and neck squamous cell carcinoma. In another embodiment, the proliferative disorder is small cell lung cancer. In another embodiment, the proliferative disorder is colorectal cancer. In another embodiment, the proliferative disorder is melanoma. In another embodiment, the proliferative disorder is ovarian cancer.

In the methods of the invention, the MEK inhibitor can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a selective Aurora A kinase inhibitor to a patient with a cell proliferative disorder. In some embodiments, the MEK inhibitor and the selective Aurora A kinase inhibitor are administered within the same patient visit. In some embodiments, the MEK inhibitor and the selective Aurora A kinase inhibitor are administered by the patient at home over a period of time that is approximately the same duration as a patient visit.

In some embodiments, the MEK inhibitor and selective Aurora A kinase inhibitor are administered to a patient, for example, a mammal, such as a human, in a sequence and within a time interval such that the inhibitor that is administered first acts together with the inhibitor that is administered second to provide greater benefit than if each inhibitor were administered otherwise. For example, the MEK inhibitor and selective Aurora A kinase inhibitor can be administered at the same time or sequentially in any order at different points in time; however, if not administered at the same time, the MEK inhibitor and selective Aurora A kinase inhibitor are administered sufficiently close in time so as to provide the desired therapeutic or prophylactic effect of the combination of the two inhibitors. In one embodiment, the MEK inhibitor and selective Aurora A kinase inhibitor exert their effect at times which overlap. In some embodiments, the MEK inhibitor and Aurora A kinase inhibitor each are administered as separate dosage forms, in any appropriate form and by any suitable route. In other embodiments, the MEK inhibitor and selective Aurora A kinase inhibitor are administered simultaneously in a single dosage form.

It will be appreciated that the frequency with which any of these therapeutic agents can be administered can be once or more than once over a period of about 2 days, about 3 days, about 4 days, about 5 days, about 6 days, about 7 days, about 8 days, about 9 days, about 10 days, about 11 days, about 12 days, about 13 days, about 14 days, about 20 days, about 28 days, about a week, about 2 weeks, about 3 weeks, about 4 weeks, about a month, about every 2 months, about every 3 months, about every 4 months, about every 5 months, about every 6 months, about every 7 months, about every 8 months, about every 9 months, about every 10 months, about every 11 months, about every year, about every 2 years, about every 3 years, about every 4 years, or about every 5 years.

For example, an agent may be administered daily, weekly, biweekly, or monthly for a particular period of time. An agent may be dosed daily over a 14 day time period, or twice daily over a seven day time period. In some embodiments, a certain amount of the MEK inhibitor can be administered daily over a period of 14 days. In some embodiments, a certain amount of the selective Aurora A kinase can be administered daily for 7 days. Alternatively, an agent may be administered daily, weekly, biweekly, or monthly for a particular period of time followed by a particular period of non-treatment. In some embodiments, a certain amount of the MEK inhibitor can be administered daily for 14 days followed by seven days of non-treatment, and repeated for two more cycles of daily administration for 14 days followed by seven days of non-treatment. In some embodiments, a certain amount of the selective Aurora A kinase inhibitor can be administered twice daily for seven days followed by 14 days of non-treatment, which may be repeated for one or two more cycles of twice daily administration for seven days followed by 14 days of non-treatment.

In one embodiment, a certain amount of the MEK inhibitor is administered daily over a period of 14 days. In another embodiment, a certain amount of the MEK inhibitor is administered daily over a period of 12 days, or 11 days, or 10 days, or nine days, or eight days. In another embodiment, a certain amount of the MEK inhibitor is administered daily over a period of seven days.

In one embodiment, a certain amount of the selective Aurora A kinase inhibitor is administered daily over a period of seven days. In another embodiment, a certain amount of the Aurora A inhibitor is administered daily over a period of six days, or five days, or four days, or three days.

In some embodiments, courses of treatment are administered concomitantly to a patient, i.e., individual doses of the MEK inhibitor and the selective Aurora A kinase inhibitor are administered as separate dosage forms yet within a time interval such that the two inhibitors can work together (e.g., within 1 hour, 2 hours, 4 hours, 6 hours, 12 hours, 24 hours, 48 hours, 72 hours, 96 hours, 5 days, 6 days, 1 week, or 2 weeks). For example, a MEK inhibitor, e.g., 3-[(2R)-2,3-dihydroxypropyl]-6-fluoro-5-[(2-fluoro-4-iodophenyl)amino]-8-methylpyrido[2,3-d]pyrimidine-4,7(3H,8H)-dione, or a pharmaceutically acceptable salt thereof can be administered once daily for 21 days in a 28-day cycle, in combination with a selective Aurora A kinase inhibitor, e.g., sodium 4-{[9-chloro-7-(2-fluoro-6-methoxyphenyl)-5H-pyrimido[5,4-d][2]benzazepin-2-yl]amino}-2-methoxybenzoate, administered twice daily for 7 days in a 21-day cycle. In other words, the dosing regimens are carried out concomitantly because day one of each cycle begins on the same day even if the therapeutic agents are not administered simultaneously or during the same day during every day of the cycle.

In one embodiment, the administration is on a 21-day dose schedule in which the MEK inhibitor is administered once daily for 14 days followed by seven days of non-treatment, in combination with administration of the selective inhibitor of Aurora A kinase twice-daily for seven days followed by 14 days of non-treatment (e.g., the MEK inhibitor is administered once daily on days 1-14 and the selective inhibitor of Aurora A kinase is administered twice daily on days 1-7 of the 21-day schedule).

In some embodiments, the treatment period during which the therapeutic agents are administered is then followed by a non-treatment period of a particular time duration, during which the therapeutic agents are not administered to the patient. This non-treatment period can then be followed by a series of subsequent treatment and non-treatment periods of the same or different frequencies for the same or different lengths of time. In some embodiments, the treatment and non-treatment periods are alternated. It will be understood that the period of treatment in cycling therapy may continue until the patient has achieved a complete response or a partial response, at which point the treatment may be stopped. Alternatively, the period of treatment in cycling therapy may continue until the patient has achieved a complete response or a partial response, at which point the period of treatment may continue for a particular number of cycles. In some embodiments, the length of the period of treatment may be a particular number of cycles, regardless of patient response. In some other embodiments, the length of the period of treatment may continue until the patient relapses.

In some embodiments, the MEK inhibitor and the selective Aurora A kinase inhibitor are cyclically administered to a patient. Cycling therapy involves the administration of a first agent (e.g., a first prophylactic or therapeutic agents) for a period of time, followed by the administration of a second agent and/or third agent (e.g., a second and/or third prophylactic or therapeutic agents) for a period of time and repeating this sequential administration. Cycling therapy can reduce the development of resistance to one or more of the therapies, avoid or reduce the side effects of one of the therapies, and/or improve the efficacy of the treatment.

In some embodiments, the MEK inhibitor is administered for a particular length of time prior to administration of the selective Aurora A kinase inhibitor. For example, in a 21-day cycle, the MEK inhibitor may be administered on days 1 to 5, days 1 to 7, days 1 to 10, or days 1 to 14, and the selective Aurora A kinase inhibitor may be administered on days 6 to 21, days 8 to 21, days 11 to 21, or days 14 to 21. In other embodiments, the selective Aurora A kinase inhibitor is administered for a particular length of time prior to administration of the MEK inhibitor. For example, in a 21-day cycle, the selective Aurora A kinase inhibitor may be administered on days 1 to 5, days 1 to 7, days 1 to 10, or days 1 to 14, and the MEK inhibitor may be administered on days 6 to 21, days 8 to 21, days 11 to 21, or days 14 to 21.

In another embodiment, the administration is on a 21-day dose schedule in which a once daily dose of MEK inhibitor is administered beginning on day eight for seven days, followed by seven days of non-treatment, in combination with twice-daily administration of the selective inhibitor of Aurora A kinase for seven days followed by 14 days of non-treatment (e.g., the MEK inhibitor is administered on days 8-14 and the selective inhibitor of Aurora A kinase is administered on days 1-7 of the 21-day schedule).

In some embodiments, the MEK inhibitor and selective Aurora A kinase inhibitor each are administered at a dose and schedule typically used for that agent when used as a single agent. In some other embodiments, when the MEK inhibitor and selective Aurora A kinase inhibitor are administered concomitantly, one or both of the agents can advantageously be administered at a lower dose than typically administered when the agent is used as a single agent, such that the dose falls below the threshold that an adverse side effect is elicited.

The therapeutically effective amounts or suitable dosages of the MEK inhibitor and the selective inhibitor of Aurora A kinase in combination depends upon a number of factors, including the nature of the severity of the condition to be treated, the particular inhibitor, the route of administration and the age, weight, general health, and response of the individual patient. In certain embodiments, the suitable dose level is one that achieves an effective exposure as measured by increased skin mitotic index, or decreased chromosome alignment and spindle bipolarity in tumor mitotic cells, or other standard measures of effective exposure in patients with cell proliferative disorders. In certain embodiments, the suitable dose level is one that achieves a therapeutic response as measured by tumor regression or other standard measures of disease progression, progression free survival, or overall survival. In other embodiments, the suitable dose level is one that achieves this therapeutic response and also minimizes any side effects associated with the administration of the therapeutic agent.

Suitable daily dosages of MEK inhibitors kinase can generally range, in single or divided or multiple doses, from about 10% to about 120% of the maximum tolerated dose as a single agent. In certain embodiments, the suitable dosages are from about 20% to about 100% of the maximum tolerated dose as a single agent. In some other embodiments, the suitable dosages are from about 25% to about 90% of the maximum tolerated dose as a single agent. In some other embodiments, the suitable dosages are from about 30% to about 80% of the maximum tolerated dose as a single agent. In some other embodiments, the suitable dosages are from about 40% to about 75% of the maximum tolerated dose as a single agent. In some other embodiments, the suitable dosages are from about 45% to about 60% of the maximum tolerated dose as a single agent. In other embodiments, suitable dosages are about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, or about 120% of the maximum tolerated dose as a single agent.

Suitable daily dosages of TAK-733 can generally range, in single or divided or multiple doses, from about 1 mg to about 40 mg per day. Other suitable daily dosages of TAK-733 can generally range, in single or divided or multiple doses, from about 10 mg to about 30 mg per day. Other suitable daily dosages of TAK-733 can generally range, in single or divided or multiple doses, from about 15 mg to about 25 mg per day. In certain embodiments, the suitable dosages are from about 5 mg once daily to about 40 mg once daily. In some other embodiments, the suitable dosages are from about 10 mg once daily to about 30 mg once daily. In some other embodiments, the suitable dosages are from about 15 mg once daily to about 25 mg once daily. In other embodiments, suitable dosages are about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, or about 20 mg per day. In certain other embodiments, suitable dosages are about 6.2 mg, about 6.4 mg, about 6.6 mg, about 6.8 mg, about 7 mg, 7.2 mg, about 7.4 mg, about 7.6 mg, about 7.8 mg, about 8 mg, about 8.2 mg, 8.4 mg, about 8.6 mg, about 8.8 mg, about 9 mg, 9.2 mg, about 9.4 mg, about 9.6 mg, about 9.8 mg, about 10 mg, 10.2 mg, about 10.4 mg, about 10.6 mg, about 10.8 mg, about 11 mg, 11.2 mg, about 11.4 mg, about 11.6 mg, about 11.8 mg, about 12, about 12.2 mg, about 12.4 mg, about 12.6 mg, about 12.8 mg, about 13 mg, 13.2 mg, about 13.4 mg, about 13.6 mg, about 13.8 mg, about 14 mg, about 14.2 mg, 14.4 mg, about 14.6 mg, about 14.8 mg, about 15 mg, 15.2 mg, about 15.4 mg, about 15.6 mg, about 15.8 mg, about 16 mg, 16.2 mg, about 16.4 mg, about 16.6 mg, about 16.8 mg, or about 17 mg once daily.

It will be understood that a suitable dosage of a MEK inhibitor may be taken at any time of the day or night. In some embodiments, a suitable dosage of a MEK inhibitor is taken in the morning. In some other embodiments, a suitable dosage of a MEK inhibitor is taken in the evening. It will be understood that a suitable dosage of a MEK inhibitor may be taken with or without food. In some embodiments a suitable dosage of a MEK inhibitor is taken with a meal. In some embodiments a suitable dosage of a MEK inhibitor is taken while fasting.

Suitable daily dosages of selective inhibitors of Aurora A kinase can generally range, in single or divided or multiple doses, from about 10% to about 120% of the maximum tolerated dose as a single agent. In certain embodiments, the suitable dosages are from about 20% to about 100% of the maximum tolerated dose as a single agent. In some other embodiments, the suitable dosages are from about 25% to about 90% of the maximum tolerated dose as a single agent. In some other embodiments, the suitable dosages are from about 30% to about 80% of the maximum tolerated dose as a single agent. In some other embodiments, the suitable dosages are from about 40% to about 75% of the maximum tolerated dose as a single agent. In some other embodiments, the suitable dosages are from about 45% to about 60% of the maximum tolerated dose as a single agent. In other embodiments, suitable dosages are about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, or about 120% of the maximum tolerated dose as a single agent.

Suitable daily dosages of alisertib can generally range, in single or divided or multiple doses, from about 20 mg to about 100 mg per day. Other suitable daily dosages of alisertib can generally range, in single or divided or multiple doses, from about 30 mg to about 90 mg per day. Other suitable daily dosages of alisertib can generally range, in single or divided or multiple doses, from about 40 mg to about 80 mg per day. In certain embodiments, the suitable dosages are from about 10 mg twice daily to about 50 mg twice daily. In some other embodiments, the suitable dosages are from about 15 mg twice daily to about 45 mg twice daily. In some other embodiments, the suitable dosages are from about 20 mg twice daily to about 40 mg twice daily. In some other embodiments, the suitable dosages are from about 25 mg twice daily to about 40 mg twice daily. In some other embodiments, the suitable dosages are from about 30 mg twice daily to about 40 mg twice daily. In other embodiments, suitable dosages are about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg per day. In certain other embodiments, suitable dosages are about 10 mg, about 15 mg, about 20 mg, about 25 mg, about 30 mg, about 35 mg, about 40 mg, about 45 mg, or about 50 mg twice daily.

It will be understood that a suitable dosage of a selective inhibitor of Aurora A kinase may be taken at any time of the day or night. In some embodiments, a suitable dosage of a selective inhibitor of Aurora A kinase is taken in the morning. In some other embodiments, a suitable dosage of a selective inhibitor of Aurora A kinase is taken in the evening. In some other embodiments, a suitable dosage of a selective inhibitor of Aurora A kinase is taken both in the morning and the evening. It will be understood that a suitable dosage of a selective inhibitor of Aurora A kinase may be taken with or without food. In some embodiments a suitable dosage of a selective inhibitor of Aurora A kinase is taken with a meal. In some embodiments a suitable dosage of a selective inhibitor of Aurora A kinase is taken while fasting.

In some embodiments, a first treatment period in which a first amount of the selective inhibitor of Aurora A kinase is administered can be followed by another treatment period in which a same or different amount of the same or a different selective inhibitor of Aurora A kinase is administered. A wide variety of therapeutic agents may have a therapeutically relevant added benefit in combination with the combination of MEK inhibitors and selective inhibitors of Aurora A kinase of the present invention. Combination therapies that comprise the MEK inhibitors and selective inhibitors of Aurora A kinase of the present invention with one or more other therapeutic agents can be used, for example, to: 1) enhance the therapeutic effect(s) of the methods of the present invention and/or the one or more other therapeutic agents; 2) reduce the side effects exhibited by the methods of the present invention and/or the one or more other therapeutic agents; and/or 3) reduce the effective dose of the MEK inhibitors and selective inhibitors of Aurora A kinase of the present invention and/or the one or more other therapeutic agents. For example, such therapeutic agents may combine with the MEK inhibitors and selective inhibitors of Aurora A kinase of the present invention to inhibit undesirable cell growth, such as inappropriate cell growth resulting in undesirable benign conditions or tumor growth.

Examples of therapeutic agents that may be used in combination with the combination of MEK inhibitors and selective inhibitors of Aurora A kinase of the present invention include, but are not limited to, anti-proliferative agents, anticancer agents, alkylating agents, antibiotic agents, antimetabolic agents, hormonal agents, plant-derived agents, and biologic agents.

Alkylating agents are polyfunctional compounds that have the ability to substitute alkyl groups for hydrogen ions. Examples of alkylating agents include, but are not limited to, bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin), nonclassic alkylating agents (altretamine, dacarbazine, and procarbazine), platinum compounds (carboplastin and cisplatin). These compounds react with phosphate, amino, hydroxyl, sulfihydryl, carboxyl, and imidazole groups. Under physiological conditions, these drugs ionize and produce positively charged ion that attach to susceptible nucleic acids and proteins, leading to cell cycle arrest and/or cell death. Combination therapy including an inhibitor of the present invention and an alkylating agent may have therapeutic synergistic effects on cancer and reduce sides affects associated with these chemotherapeutic agents.

Antibiotic agents are a group of drugs that produced in a manner similar to antibiotics as a modification of natural products. Examples of antibiotic agents include, but are not limited to, anthracyclines (e.g. doxorubicin, daunorubicin, epirubicin, idarubicin and anthracenedione), mitomycin C, bleomycin, dactinomycin, plicatomycin. These antibiotic agents interfere with cell growth by targeting different cellular components. For example, anthracyclines are generally believed to interfere with the action of DNA topoisomerase II in the regions of transcriptionally active DNA, which leads to DNA strand scissions. Bleomycin is generally believed to chelate iron and forms an activated complex, which then binds to bases of DNA, causing strand scissions and cell death. Combination therapy including an inhibitor of the present invention and an antibiotic agent may have therapeutic synergistic effects on cancer and reduce sides affects associated with these chemotherapeutic agents.

Antimetabolic agents are a group of drugs that interfere with metabolic processes vital to the physiology and proliferation of cancer cells. Actively proliferating cancer cells require continuous synthesis of large quantities of nucleic acids, proteins, lipids, and other vital cellular constituents. Many of the antimetabolites inhibit the synthesis of purine or pyrimidine nucleosides or inhibit the enzymes of DNA replication. Some antimetabolites also interfere with the synthesis of ribonucleosides and RNA and/or amino acid metabolism and protein synthesis as well. By interfering with the synthesis of vital cellular constituents, antimetabolites can delay or arrest the growth of cancer cells. Examples of antimetabolic agents include, but are not limited to, fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, and gemcitabine. Combination therapy including an inhibitor of the present invention and a antimetabolic agent may have therapeutic synergistic effects on cancer and reduce sides affects associated with these chemotherapeutic agents.

Hormonal agents are a group of drug that regulate the growth and development of their target organs. Most of the hormonal agents are sex steroids and their derivatives and analogs thereof, such as estrogens, androgens, and progestins. These hormonal agents may serve as antagonists of receptors for the sex steroids to down regulate receptor expression and transcription of vital genes. Examples of such hormonal agents are synthetic estrogens (e.g. diethylstibestrol), antiestrogens (e.g. tamoxifen, toremifene, fluoxymesterol and raloxifene), antiandrogens (bicalutamide, nilutamide, and flutamide), aromatase inhibitors (e.g., aminoglutethimide, anastrozole and tetrazole), ketoconazole, goserelin acetate, leuprolide, megestrol acetate and mifepristone. Combination therapy including an inhibitor of the present invention and a hormonal agent may have therapeutic synergistic effects on cancer and reduce sides affects associated with these chemotherapeutic agents.

Plant-derived agents are a group of drugs that are derived from plants or modified based on the molecular structure of the agents. Examples of plant-derived agents include, but are not limited to, vinca alkaloids (e.g., vincristine, vinblastine, vindesine, vinzolidine and vinorelbine), podophyllotoxins (e.g., etoposide (VP-16) and teniposide (VM-26)), and taxanes (e.g., paclitaxel and docetaxel). These plant-derived agents generally act as antimitotic agents that bind to tubulin and inhibit mitosis. Podophyllotoxins such as etoposide are believed to interfere with DNA synthesis by interacting with topoisomerase II, leading to DNA strand scission. Combination therapy including an inhibitor of the present invention and a plant-derived agent may have therapeutic synergistic effects on cancer and reduce sides affects associated with these chemotherapeutic agents.

Biologic agents are a group of biomolecules that elicit cancer/tumor regression when used alone or in combination with chemotherapy and/or radiotherapy. Examples of biologic agents include, but are not limited to, immuno-modulating proteins such as cytokines, monoclonal antibodies against tumor antigens, tumor suppressor genes, and cancer vaccines. Combination therapy including an inhibitor of the present invention and a biologic agent may have therapeutic synergistic effects on cancer, enhance the patient's immune responses to tumorigenic signals, and reduce potential sides affects associated with this chemotherapeutic agent.

Cytokines possess profound immunomodulatory activity. Some cytokines such as interleukin-2 (IL-2, aldesleukin) and interferon have demonstrated antitumor activity and have been approved for the treatment of patients with metastatic renal cell carcinoma and metastatic malignant melanoma. IL-2 is a T-cell growth factor that is central to T-cell-mediated immune responses. The selective antitumor effects of IL-2 on some patients are believed to be the result of a cell-mediated immune response that discriminate between self and nonself. Examples of interleukins that may be used in conjunction with inhibitors of the present invention include, but are not limited to, interleukin 2 (IL-2), and interleukin 4 (IL-4), interleukin 12 (IL-12).

Interferons include more than 23 related subtypes with overlapping activities, all of the IFN subtypes within the scope of the present invention. IFN has demonstrated activity against many solid and hematologic malignancies, the later appearing to be particularly sensitive.

Other cytokines that may be used in conjunction with the inhibitors of the present invention include those cytokines that exert profound effects on hematopoiesis and immune functions. Examples of such cytokines include, but are not limited to erythropoietin, granulocyte-CSF (filgrastin), and granulocyte, macrophage-CSF (sargramostim). These cytokines may be used in conjunction with an inhibitor of the present invention to reduce chemotherapy-induced myelopoietic toxicity.

Other immuno-modulating agents other than cytokines may also be used in conjunction with the inhibitors of the present invention to inhibit abnormal cell growth. Examples of such immuno-modulating agents include, but are not limited to *bacillus* Calmette-Guerin, levamisole, and octreotide, a long-acting octapeptide that mimics the effects of the naturally occurring hormone somatostatin.

Monoclonal antibodies against tumor antigens are antibodies elicited against antigens expressed by tumors, preferably tumor-specific antigens. For example, monoclonal antibody HERCEPTIN® (Trastruzumab) is raised against human epidermal growth factor receptor2 (HER2) that is overexpressed in some breast tumors including metastatic breast cancer. Overexpression of HER2 protein is associated with more aggressive disease and poorer prognosis in the clinic. HERCEPTIN® is used as a single agent for the treatment of patients with metastatic breast cancer whose tumors over express the HER2 protein. Combination therapy including an inhibitor of the present invention and HERCEPTIN® may have therapeutic synergistic effects on tumors, especially on metastatic cancers.

Another example of monoclonal antibodies against tumor antigens is RITUXAN® (Rituximab) that is raised against CD20 on lymphoma cells and selectively deplete normal and malignant $CD20^+$ pre-B and mature B cells. RITUXAN® is used as single agent for the treatment of patients with relapsed or refractory low-grade or follicular, CD20+, B cell non-Hodgkin's lymphoma. Combination therapy including an inhibitor of the present invention and RITUXAN® may have therapeutic synergistic effects not only on lymphoma, but also on other forms or types of malignant tumors.

Tumor suppressor genes are genes that function to inhibit the cell growth and division cycles, thus preventing the development of neoplasia. Mutations in tumor suppressor genes cause the cell to ignore one or more of the components of the network of inhibitory signals, overcoming the cell cycle check points and resulting in a higher rate of controlled cell growth-cancer. Examples of the tumor suppressor genes include, but are not limited to, DPC-4, NF-1, NF-2, RB, p53, WT1, BRCA1, and BRCA2.

DPC-4 is involved in pancreatic cancer and participates in a cytoplasmic pathway that inhibits cell division. NF-1 codes for a protein that inhibits Ras, a cytoplasmic inhibitory protein. NF-1 is involved in neurofibroma and pheochromocytomas of the nervous system and myeloid leukemia. NF-2 encodes a nuclear protein that is involved in meningioma, schwanoma, and ependymoma of the nervous system. RB codes for the pRB protein, a nuclear protein that is a major inhibitor of cell cycle. RB is involved in retinoblastoma as well as bone, bladder, small cell lung and breast cancer. P53 codes for p53 protein that regulates cell division and can induce apoptosis. Mutation and/or inaction of p53 is found in a wide ranges of cancers. WT1 is involved in Wilms tumor of the kidneys. BRCA1 is involved in breast and ovarian cancer, and BRCA2 is involved in breast cancer. The tumor suppressor gene can be transferred into the tumor cells where it exerts its tumor suppressing functions. Combination therapy including an inhibitor of the present invention and a tumor suppressor may have therapeutic synergistic effects on patients suffering from various forms of cancers.

Cancer vaccines are a group of agents that induce the body's specific immune response to tumors. Most of cancer vaccines under research and development and clinical trials are tumor-associated antigens (TAAs). TAA are structures (i.e. proteins, enzymes or carbohydrates) which are present on tumor cells and relatively absent or diminished on normal cells. By virtue of being fairly unique to the tumor cell, TAAs provide targets for the immune system to recognize and cause their destruction. Example of TAAs include, but are not limited to gangliosides (GM2), prostate specific antigen (PSA), alpha-fetoprotein (AFP), carcinoembryonic antigen (CEA) (produced by colon cancers and other adenocarcinomas, e.g. breast, lung, gastric, and pancreas cancer s), melanoma associated antigens (MART-1, gp100, MAGE 1,3 tyrosinase), papillomavirus E6 and E7 fragments, whole cells or portions/lysates of antologous tumor cells and allogeneic tumor cells.

An adjuvant may be used to augment the immune response to TAAs. Examples of adjuvants include, but are not limited to, *bacillus* Calmette-Guerin (BCG), endotoxin lipopolysaccharides, keyhole limpet hemocyanin (GKLH), interleukin-2 (IL-2), granulocyte-macrophage colony-stimulating factor (GM-CSF) and cytoxan, a chemotherapeutic agent which is believe to reduce tumor-induced suppression when given in low doses.

The present invention is also directed to kits and other articles of manufacture for treating proliferative diseases. In one embodiment, a kit is provided that comprises a MEK inhibitor, or a pharmaceutically acceptable salt thereof, as described herein; a selective inhibitor of Aurora A kinase, or a pharmaceutically acceptable salt thereof, as described herein; and instructions. The kit may optionally further include the one or more additional therapeutic agents. The instructions may indicate the disease state for which the kit is to be used, storage information, dosing information and/or instructions regarding how to administer the MEK inhibitor, the selective inhibitor of Aurora A kinase, and/or additional therapeutic agent or agents. The kit may also comprise packaging materials. The packaging material may comprise a container for housing the contents of the kit. The kit may also optionally comprise additional components, such as syringes for administration of the contents of the kit. The kit may comprise the MEK inhibitor, the selective inhibitor Aurora A kinase, and/or additional therapeutic agent or agents in single or multiple dose forms.

In another embodiment, an article of manufacture is provided that comprises the MEK inhibitor, or a pharmaceutically acceptable salt thereof; the selective inhibitor of Aurora A kinase, or a pharmaceutically acceptable salt thereof; and packaging materials. The article of manufacture may optionally further include the one or more additional therapeutic agents. The packaging material may comprise a container for housing the contents of the article of manufacture. The container may optionally comprise a label indicating the disease state for which the article is to be used, storage information, dosing information and/or instructions regarding how to administer the MEK inhibitor, selective inhibitor of Aurora A kinase, and/or additional therapeutic agent or agents. The article of manufacture may also optionally comprise additional components, such as syringes for administration of the composition. The article may comprise the MEK inhibitor, selective inhibitor of Aurora A kinase, and/or additional therapeutic agent or agents in single or multiple dose forms.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices and materials are herein described. All publications mentioned herein are hereby incorporated by reference in their entirety for the purpose of describing and disclosing the materials and methodologies that are reported in the publication which might be used in connection with the invention.

EXAMPLES

In the Examples described below, MLN8237 (alisertib) refers to the sodium salt, sodium 4-{[9-chloro-7-(2-fluoro-6-methoxyphenyl)-5H-pyrimido[5,4-d][2]benzazepin-2-yl]amino}-2-methoxybenzoate monohydrate, and TAK-733 refers to 3-[(2R)-2,3-dihydroxypropyl]-6-fluoro-5-[(2-fluoro-4-iodophenyl)amino]-8-methylpyrido[2,3-d]pyrimidine-4,7(3H,8H)-dione.

Cell Culture and Compound Treatment

A375, Colo205, PC-3 and SK-Mel-2 human tumor cell lines were obtained from the American Type Culture Collection (ATCC [Manassas, Va.]) and maintained according to the ATCC's recommendations. A2780 human tumor cell line was obtained from The European Collection of Cell Cultures (ECACC) (Sigma-Aldrich distribution [St. Louis, Mo., USA]) and also maintained following the ECACC's recommendations. The following test articles were used in these studies: MLN8237-004-H and TAK-733-001-B obtained from an internal drug source, dissolved in DMSO at 10 mM concentration and aliquoted into small vials to reduce the number of freeze-thaw cycles. Aliquots were stored at −20° C. DMSO was used as vehicle. All compounds were previously diluted within the growth media for each particular cell line before addition to the cells.

Statistical Analysis

The statistical significance (p value) for various experiments was assessed either by using two-tailed unpaired t-tests with Bonferroni correction or 1-way ANOVA analysis of variance followed by a Dunnett's multiple comparison post test, or f-tests used to assess unequal variance.

Experiment 1

Video Microscopy

Experimental design: A2780 and A375 cells were seeded at $1.3 \times 10^4$ or $0.6 \times 10^4$ cells/ml respectively and grown on 12 well cell culture dishes overnight at 37° C. with 5% $CO_2$.

Cells were incubated with DMSO, TAK-733, MLN8237 or TAK-733 and MLN8237 simultaneously. Immediately following drug addition, cells were placed in a live cell timelapse environmental enclosure (Solent Scientific [Segensworth, UK]) maintained at 37° C. with 5% $CO_2$. Live images of cells were acquired by bright field illumination (Hoffman modulation) every five minutes for 120 hours using an inverted epifluorescence microscope (Eclipse TE2000-U, Nikon [Melville, N.Y.]) equipped with a 20× objective and an automated XYZ stage (Prior Scientific [Rockland, Mass., USA]). Images were captured using a cooled CCD camera (Orca-ER, Hamamatsu [Bridgewater, N.J., USA]) and Metamorph software (Molecular Devices [Sunnyvale, Calif., USA]) was used to stack images and to generate AVI files. The timing of cell cycle events was determined by measuring the average elapsed time required for cells to become rounded (mitotic cells), for rounded cells to divide, and for recently divided cells to flatten and reattach to the plate surface.

Results: Cultured A2780 cells treated with the Mek inhibitor TAK-733 (at 200 nM) continued to divide over a 5 day experiment. In timelapse video microscopy observations of cell cycle progression, cells treated with TAK-733 underwent one and two divisions with almost the same frequency as control cells (~90%). For up to 4 divisions, cells divided at almost a 40% frequency relative to controls (FIG. 1). Though the TAK-733 cells continued to divide throughout the 5 day experiment, the time between mitotic events was delayed relative to the DMSO treated cells, 29 hours in A2780s treated with 200 nM TAK-733 versus 17 hours in the DMSO treated control (Table 4), demonstrating that TAK-733 treatment disrupted normal cell cycle progression.

TABLE 4

Cell cycle progression effects of TAK-733, MLN8237 or the combination on cultured A2780 tumor cells

| Treatment | Time to 1st mitosis (Hr) | Time through all mitoses (min) | Time between mitoses (Hr) |
|---|---|---|---|
| DMSO | 8.1 | 38 | 17 |
| 200 nM TAK-733 | 7.3 | 33 | 29[a] |
| 50 nM MLN8237 | 14.2 | 109[a] | 27[a] |
| 200 nM TAK-733, 50 nM MLN8237 | 12.2 | 107[ab] | 41[a] | p values based on t-test with Bonferroni correction
[a]p < 0.0001 relative to DMSO
[b]p < 0.0001 relative to TAK-733

The results observed in the video microscopy assay described above using the A2780 cells treated with TAK-733 at 200 nM were corroborated with flow cytometry using CFDA-SE (Carboxyfluorescein diacetate succinimidyl ester). CFDA-SE is a cell permeable small molecule that enters cells, whereby it is processed by intracellular esterases to CFSE, a fluorescent label that is retained within the cell cytoplasm. The rate of decay of CFSE signal is a measure of the cell division rate, as the signal can only be diluted during division.

Experiment 2

Carboxyfluorescein Succinimidyl Ester (CFSE) Assay

Experimental design: $5 \times 10^6$ A375 or Colo205 cells were labeled with 1 μM carboxyfluorescein diacetate succinmydyl ester (CFDA-SE, Molecular Probes/Invitrogen [Eugene, Oreg., USA]) in PBS pre-warmed to 37° C. for 10 minutes. Staining was quenched by the addition of 5 volumes of ice cold media to the cells, followed by incubation for 5 minutes on ice. Cells were washed 3× in fresh warm media and plated at $2 \times 10^4$ cells/ml in a 6 well plate. Cells were treated with DMSO (0.05% v/v) or TAK-733 at the appropriate $IC_{50}$ or $IC_{90}$ concentration for 24 and 48 hours. Cells were harvested at the appropriate time point with trypsin ethylenediaminetetraacetic acid (EDTA) 1× (Gibco/Invitrogen [Carlsbad, Calif., USA]), washed once with phosphate-buffered saline (PBS) then resuspended in PBS containing 1% BSA. Samples were passed through a cell strainer to ensure a single cell suspension and CFSE fluorescence was assessed by flow cytometry (FACS Canto II, Becton Dickinson [San Jose, Calif., USA]) and samples analyzed using FACSDIVA software (Becton Dickinson [San Jose, Calif., USA]).

Results: The attenuation of CFSE signal in response to TAK-733 treatment occurred at a comparable rate to controls consistent with the cells continuing to cycle after Mek inhibition. This continued cell cycle division in the presence of TAK-733 has been demonstrated to occur with abnormal DNA content profiles determined using flow cytometry consistent with altered rates of passage through S and G2/M phase.

Experiment 3

BrdU Proliferation Assay

A2780, A375, PC-3, and SK-MeI-2 human tumor cell lines were seeded at $2.0 \times 10^3$, $1.0 \times 10^3$, $4.0 \times 10^3$ and $2.0 \times 10^3$ cells per well, respectively, in 80 μL of the appropriate cell culture growth media. Plating densities were chosen to ensure optimal linear growth over 120 hours. After 20 hours, 10 μL of each compound was added to the cells in a matrix with dose responses of both agents. MLN8237 was added to all cell lines in 4-fold serial dilutions in DMSO diluted with growth media to achieve final concentrations ranging from 5 to 0.00122 μM. TAK-733 was added to A375 and SK-MeI-2 cell lines in 10-fold serial dilutions in DMSO diluted with growth media to achieve final concentrations ranging from 10 to $1.0 \times 10^{-7}$ μM. For A2780 and PC-3 cell lines, TAK-733 was added so that the final concentrations started at 50 and 25 μM and continued with a 5-fold serial dilution in DMSO diluted with growth media from 10 to 0.00064 μM. Each matrix was generated in triplicate with each replicate on a separate plate. Cells treated with DMSO diluted with growth media (n=1 per plate; 0.65% final concentration for A375 and SK-MeI-2 cell lines, and 0.75% final concentration for A2780 and PC-3 cell lines) served as the untreated control. The cells were treated with MLN8237 and TAK-733 for 96 hours at 37° C. in a humidified cell culture chamber.

Cell proliferation of each cell line was measured using the cell proliferation enzyme-linked immunosorbent assay (ELISA), 5-bromo-2-deoxyuridine (BrdU) colorimetric kit according to the manufacturer's instructions (Roche [Mannheim, Germany]). The assay measures cell proliferation by quantifying BrdU incorporation into replicating deoxyribonucleic acid (DNA). Briefly, each well was incubated with 10 μL of BrdU labeling reagent for 2 hours at 37° C. in a humidified cell culture chamber. After aspiration of the labeling media, the plates were wrapped in foil and kept at 4° C. to assay at a future time. The cells were fixed and denatured by adding 100 L of ethanol to each well and incubated for 30 minutes at room temperature. The ethanol was aspirated and 50 µl of blocking reagent (Roche [Mannheim, Germany]) was added to the cells and incubated for 30 minutes. 100 µL of peroxidase-conjugated anti BrdU antibody ([anti-BrdU-POD]; 1:100 in antibody dilution buffer) was added to the cells. The cells were incubated with the antibody for 120 minutes at room temperature. The cells were then washed 2× with 150 µL of wash buffer per well and 100 µL of tetramethyl benzidine was then added. The cells were incubated for 15 to 30 minutes at room temperature prior to spectrophotometric analysis. A SpectraMax Plus 384 plate reader (Molecular Devices [Sunny Vale Calif., USA]) or WALLAC 1420 Workstation (Perkin Elmer [Turku, Finland]) were used to measure the absorbance of each well at 395 or 405 nm, respectively, depending on the machine used. The A2780 and A375 cell lines were measured using the SpectraMax Plus at 395 nm, while the PC-3 and SK-Mel-2 cell lines were measured using the WALLAC 1420 Workstation at 405 nm. Analysis of the data was performed using GraphPad Prism 5.0.

Results: A2780, A375, SKMEL-2 and PC-3 cells were treated with various concentrations of either MLN8237 or TAK-733 for 96 hours, and concentration response curves were generated for each molecule as a single agent. The effect on $IC_{50}$ and $IC_{90}$ for MLN8237 in response to various concentrations of TAK-733 was then determined as shown in Table 5. The addition of TAK-733 shifted the $IC_{50}$ and $IC_{90}$ of MLN8237 in the A2780, SKMEL-2 and PC-3 cell lines in a concentration-dependent manner (Table 5). No added benefit was observed in the A375 cell line.

70% ethanol and stored at −20° C. for at least 24 hours. The cells were washed once more in PBS, then resuspended in 50 µg/ml propidium iodide (Invitrogen, [Carlsbad, Calif., USA]) and 30 µg/ml ribonuclease (RNAse) A (Sigma [St Louis, Mo., USA]) in PBS and incubated for 30 minutes at room temperature protected from light. Cell cycle distributions were determined by measuring deoxyribonucleic acid (DNA) content using flow cytometry on a FACS Canto II flow cytometer (Becton Dickinson [San Jose, Calif., USA]) and samples were analyzed using FACSDIVA software (Becton Dickinson [San Jose, Calif., USA]).

Figure 2:
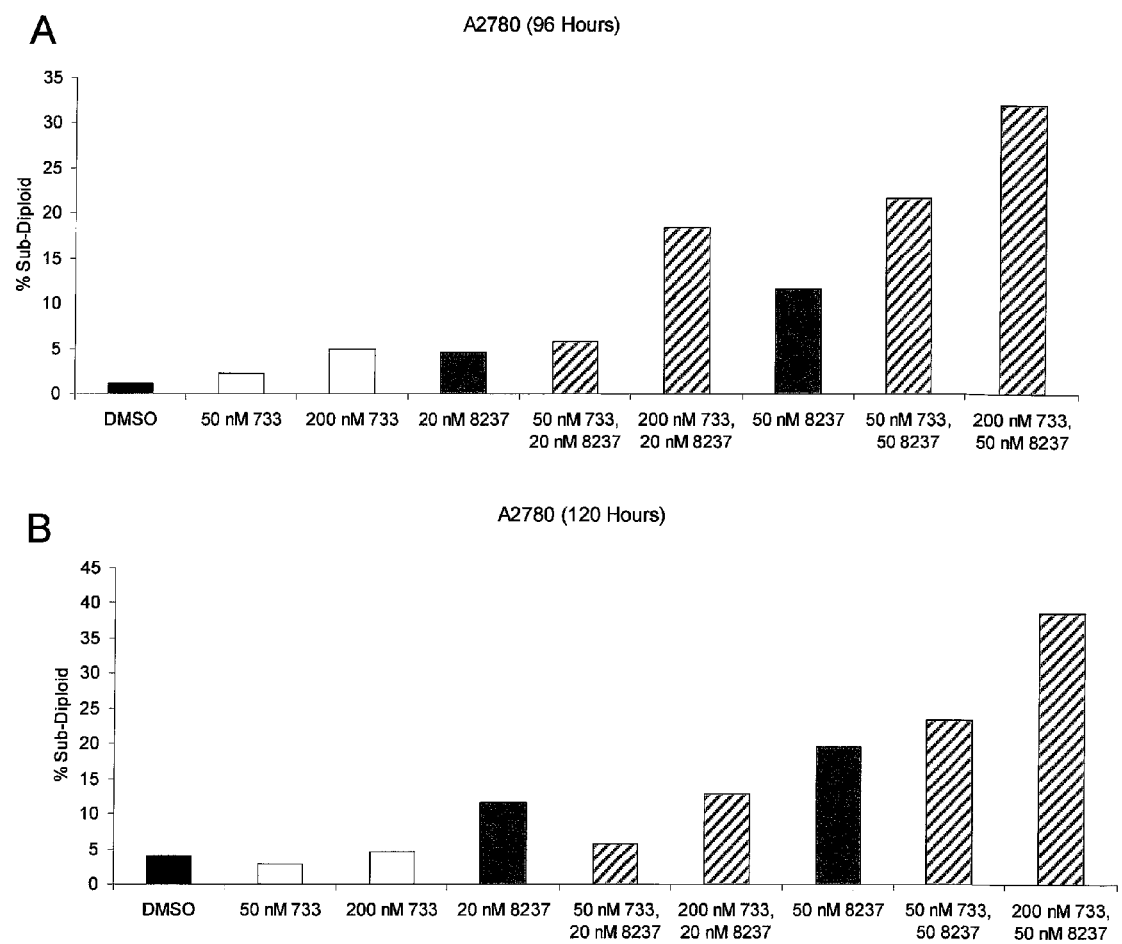
FIG. 2 The combination of TAK-733 & MLN8237 leads to a moderate increase in cell death as compared to single agents alone. A2780 cells were seeded at 2×104 cells/ml and grown on 6 well cell culture dishes overnight at 37° C. with 5% CO2. Cells were treated with DMSO (0.05% v/v), TAK-733 (50 nM or 200 nM), MLN8237 (20 nM or 50 nM) or TAK-733 and MLN8237 simultaneously and incubated at 37° C. with 5% CO2 for 96 (A) or 120 (B) hours. Cell cycle profiles were generated as described in methods. Sub-diploid cells were gated as those with a lower level of propidium iodide fluorescence than cells with 2N DNA content. In this paragraph, MLN8237 refers to the sodium salt, sodium 4-{[9-chloro-7-(2-fluoro-6-methoxyphenyl)-5H-pyrimido[5,4-d][2]benzazepin-2-yl]amino}-2-methoxybenzoate monohydrate, and TAK-733 refers to 3-[(2R)-2,3-dihy-droxypropyl]-6-fluoro-5-[(2-fluoro-4-iodophenyl)amino]-8-methylpyrido[2,3-d]pyrimidine-4,7(3H, 8H)-dione.

Results: The sub-diploid DNA content of cultured A2780 cells was quantified using flow cytometry profiles after treatment with DMSO, TAK-733, MLN8237 or the combination of TAK-733 and MLN8237 for 96 and 120 hours (FIGS. 2A and 2B, respectively). As can be seen in FIG. 2A, neither TAK-733 nor MLN8237 caused appreciable increases in the percentage of sub-diploid cells at the concentrations tested relative to DMSO, with the exception of the 50 nM MLN8237 treated sample. In combination, however, TAK-733 and MLN8237 caused an increase in the percentage of sub-diploid cells at several of the concentrations tested, namely 200 nM TAK-733/20 nM MLN8237; 50 nM TAK-733/50 nM MLN8237; and 200 nM TAK-733/50 nM MLN8237. As can be seen in FIG. 2B, which represents 120 hours of cell culture, the combination of TAK-733 and MLN8237 at the higher concentration of MLN8237 caused an increase in the percentage of sub-diploid cells.

As can be seen in FIG. 1, the frequency of mitotic events that occur over a 5 day period in A2780 cells treated with

TABLE 5

MLN8237 $IC_{50}$ and $IC_{90}$ with varying concentrations of TAK-733 in cultured tumor cells

| TAK-733 (nM) | A2780 | | A375 | | SKMEL-2 | | PC-3 | |
|---|---|---|---|---|---|---|---|---|
| | $IC_{50}$[a] (nM) | $IC_{90}$[a] (nM) | $IC_{50}$ (nM) | $IC_{90}$ (nM) | $IC_{50}$ (nM) | $IC_{90}$ (nM) | $IC_{50}$ (nM) | $IC_{90}$ (nM) |
| 0.0 | 43 | >5000 | 59 | 530 | 67 | >5000 | 134 | >5000 |
| 0.0001 | | | 73 | 554 | | | | |
| 0.001 | | | 63 | 408 | | | | |
| 0.01 | | | 58 | 882 | 66 | >5000 | | |
| 0.1 | | | 62 | 325 | 54 | >5000 | | |
| 0.64 | 34 | >5000 | | | | | | |
| 1 | | | 65 | >5000 | 48 | >5000 | | |
| 3.2 | 29 | 288 | | | | | | |
| 10 | | | | | 16 | 309 | | |
| 16 | 19 | 28 | | | | | 84 | >5000 |
| 80 | 11 | 46 | | | | | 93 | 1064 |
| 400 | | | | | | | 100 | 890 |
| 2000 | | | | | | | 74 | 569 |

[a]MLN8237 $IC_{50}$ and $IC_{90}$ determined after treating cells with varying concentrations of MLN8237 and TAK-733 for 96 hours using a BrdU proliferation assay Experiment 4

Quantification of Sub-Diploid Cells by Flow Cytometry

A2780, A375, PC-3 and SK-MEL-2 cells were seeded at 2×10$^4$ cells/ml and grown on 6 well cell culture dishes overnight at 37° C. with 5% $CO_2$. Cells were treated with DMSO, TAK-733, MLN8237 or TAK-733 and MLN8237 simultaneously and incubated at 37° C. with 5% $CO_2$ for the appropriate amount of time. At the relevant time points cells were harvested with trypsin ethylenediaminetetraacetic acid (EDTA) 1× (Gibco/Invitrogen [Carlsbad, Calif., USA]), washed once with phosphate-buffered saline (PBS), fixed in both TAK-733 and MLN8237 is significantly reduced relative to cells treated with either agent alone. This is consistent with the increase in the average time between mitotic events in cells treated with combined TAK-733 and MLN8237 relative to the single agents (Table 4). These data collectively demonstrate that the combination of TAK-733 and MLN8237 perturb cell cycle progression to a greater extent than either agent alone. The percentage of cultured A2780 cells with greater than 4N DNA was quantified from the flow cytometry profiles at 96 hours (Table 6). The results demonstrate that single agent MLN8237 caused a substantial increase in the percentage of cells with greater than 4N DNA content at 24 and 48 hours. In all of the cell lines tested, with the exception of PC-3 cells, there was a dramatic reduction in the percentage of cells with greater than 4N DNA content when TAK-733 was added in combination with MLN8237 (back to levels comparable to control levels). In contrast, in the PC-3 cell line, which was the only TAK-733 insensitive cell line tested, this reduction in the percentage of cells with greater than 4N DNA content was not observed. These data support the idea that TAK-733 suppresses cell cycle progression subsequent to abnormal mitoses induced by MLN8237. This finding is in agreement with published literature describing the MEK pathway's role in cell cycle checkpoint function ((*Oncogene* (2007) 26:4689-98; *Mol Biol Cell.* (2006) 17:5227-40; *Cancer Res.* (2008) 68:5113-21; *Cell Cycle* (2011) 10:481-91; *Oncogene* (2006) 25:1153-64).

TABLE 6

Percentage of cells with greater than 4N DNA[a]

| Treatment | A2780 | | A375 | | SKMEL-2 | | PC3 | |
|---|---|---|---|---|---|---|---|---|
| | 24 Hr | 48 Hr | 24 Hr | 48 Hr | 24 Hr | 48 Hr | 24 Hr | 48 Hr |
| DMSO | 1.7 | 2.2 | 0.9 | 1.4 | 3.1 | 2.7 | 10.5 | 10.7 |
| TAK-733 | 2.5 | 4.4 | 0.5 | 0.6 | 2.5 | 3.8 | 10.7 | 11.4 |
| MLN8237 | 9.6 | 13 | 16 | 18.6 | 14.5 | 36.4 | 21 | 30.5 |
| TAK-733, MLN8237 | 3.6 | 5.3 | 2.7 | 3.2 | 6.9 | 11.3 | 20.5 | 31.8 |

[a]The percentage of greater than 4N cells was determined by staining fixed cells with propidium iodide and measuring the DNA content by flow cytometry.

Experiment 5

Anti-Tumor Activity of TAK-733 and MLN8237, as Single Agents or in Combination or Dosed in Schedules Administered Orally to Female Nude Mice Bearing NCI-H23 Non Small Cell Lung Carcinoma Xenografts The objective of this study is to assess the tumor response activity and establish the response rate of NCI-H23 xenografts to multiple doses of TAK-733 and MLN8237 as single agent or in combination by measurement of the treatment induced delay in tumor growth and body weight loss when administered PO to mice.

Test and Control Articles: TAK-733 was prepared in 0.5% methylcellulose 400 (MC) (Wako Chemical USA, Richmond, Va., USA) every 5 days and stored at approximately 25° C. in the dark.

MLN8237 was prepared in 10% hydroxypropyl-beta-cyclodextrin (HP-β-CD) (Sigma, St. Louis, Mo., USA)+1% NaHCO3 (Sigma, St. Louis, Mo., USA) every 5 days and stored at approximately 25° C. in the dark.

Test System: The animals used in this study are described in Table 7. Low passage NCI-H23 cells were grown in RPMI (Roswell Park Memorial Institute)-1640 (ATCC, Manassas, Va., USA) 10% Fetal Bovine Serum (PAA Laboratories PTY LTD, Morningside, QLD, Australia) and supplied at a concentration of $5.0\times10^7$ cells/ml Matrigel support (BD Biosciences, Bedford, Mass., USA). $5.0\times10^6$ NCI-H23 cells/animal (0.1 ml injection volume) were implanted SC into the right flank of Balb/c nude mice.

TABLE 7

| | Test System |
|---|---|
| Species: | *Mus musculus* |
| Strain: | nude |
| Source: | Harlan Laboratories (Indianapolis, IN, USA) |
| Number of animals per group: | 8 |
| Total number of animals: | 64 |
| Age and sex: | 14 weeks at start of dosing, female |
| Weight: | 24 grams at start of dosing |
| Acclimation period: | At least 31 days |

Experimental Design: 7-9 week old female Balb/c nude mice were inoculated subcutaneously in the flank (cell suspension) with $5.0\times10^6$ NCI-H23 cells. Tumor growth was monitored with vernier calipers. The mean tumor volume was calculated using the formula $V=W^2\times L/2$. When the mean tumor volume (MTV) reached approximately 105 mm$^3$, the animals were randomized into 8 treatment groups (n=8/group). Mice were then dosed with vehicles in combination (10% HP-β-CD+1% NaHCO$_3$ and 0.5% MC), TAK-733, MLN8237, combinations of TAK-733 and MLN8237, or TAK-733 and MLN8237 administered individually for 10 days each with one day off in between, over a 21 day period. Tumor growth and body weight were measured twice per week. Tumor growth inhibition and body weight change were calculated on Day 99 of treatment.

Antitumor activity was determined by calculating the percent TGI ([mean tumor volume of the control group−mean tumor volume of a treated group]/mean tumor volume of the control group) on Day 99. Treatment started on Day 1 for 21 days. For many tumor/treatment combinations, tumor volume at the end of therapy provides an inaccurate measure of tumor response. Many therapies do not kill tumors cells promptly but kill cells over several generations of proliferation and immediate assessment of therapeutic effects at the end of therapy has limited accuracy. Thus, extending the study to include tumor regrowth allows for the evaluation of the differences in tumor cellular response between groups. The use of Day 99 allows us to evaluate tumor response and statistically compare the ΔAUC for each group over the regrowth period.

Additional endpoints used to evaluate efficacy were: complete and partial tumor response CR and PR), and the number of tumor-free survivors (TFS) at the end of the study. A CR was defined as a decrease in tumor mass to an undetectable size (<50 mm$^3$), and PR was defined as a greater than 50% decrease in tumor mass from that at first treatment. Animals were considered TFS if no measurable tumor was observed at study termination (Day 135), PRs were considered exclusive of CRs, whereas TFS were included in the CR count.

Statistical Analysis: Statistical analysis was performed with a linear mixed effects regression model. This model takes into account the differences in trends of tumor growth between control and treated samples. Differences among mice were treated as random effects, and a compound symmetry covariance structure was used to model the variability between repeated tumor measurements on each mouse. Treatment comparisons were performed by using the fitted curves from the model to calculate the changes in the areas under the tumor volume-versus-time curves (ΔAUCs). The significance of the ΔAUC was assessed using permutation testing. P-values <0.05 were considered significant.

Drug combinations were assessed for synergy using observed AUC values. The change in AUC relative to the control was calculated for both single agent treatment groups as well as the combination group. The interaction between the two compounds was then assessed by comparing the change in AUC observed in the combination group to the sum of the changes observed in both single agents. A statistically significant p value (p<0.05) suggests that the interaction between the two compounds was either antagonistic or synergistic.

Results and Discussion

Tumors in the vehicle-control group grew progressively in all surviving mice and reached the MTV size of 422 mm$^3$ (2× tumor volume doubling from initial size) in 71.6 days. Tumor growth was approximately log-linear between Days 0 and 28 and showed a tumor volume doubling time of 35 days.

Daily PO administration of 10 mg/kg TAK-733 or 20 mg/kg MLN8237 for 21 days resulted in TGI of 31.9% and 43.4% in NCI-H23 xenograft mice that was not statistically significant from control (p>0.05). TAK-733 10 mg/kg PO QD resulted in 1 of 8 PR and 1 of 8 CR with 1 of 8 TFS. MLN8237 20 mg/kg PO QD resulted in 2 of 8 CR and 2 TFS. Treatment with 30 mg/kg of MLN8237 PO resulted in antitumor activity that was statistically significant from vehicle control, (p<0.05) with TGI of 73.3% and 4 of 8 PR and 4 of 8 CR and 2 TFS. Concurrent combination treatment (QD for 21 days) of TAK-733 at 10 mg/kg and MLN8237 at 20 mg/kg resulted in antitumor activity that was significantly different from vehicle control (p<0.05) with 24.5% decrease in total tumor burden at the end of the study and 8 of 8 CR and 2 TFS. TAK-733 at 10 mg/kg and MLN8237 at 30 mg/kg resulted in statistically significant (p<0.05) antitumor activity with 100% TGI and 8 of 8 CR and 7 of 8 TFS and the effect was shown to be synergistic. The high dose combination of treatment also resulted in a significant (p<0.05) increase in TGI over single agent therapies.

Intermittent dosing (alternation) of the TAK-733/MLN8237 combination did not result in any therapeutic advantage over concurrent combination therapy. Oral administration of 10 mg/kg TAK-733 (10 days treatment 1 day dose holiday) followed by 20 mg/kg MLN8237 (10 days treatment) or the opposite, 20 mg/kg MLN8237 (10 days treatment and 1 day dose holiday) followed by 10 mg/kg TAK-733 (10 days treatment) resulted in significant (p<0.05) TGI of 12.5% and 18.1%, respectively, in NCI-H23 cell implanted mice. TAK-733 followed by MLN8237 treatment resulted in 7 of 8 PR, 1 of 8 CR, and 1 of 8 TFS. MLN8237 followed by TAK-733 resulted in PR in 2 of 8, CR in 2 of 8, and 2 of 8 TFS. No spontaneous regressions (PR or CR) were seen in the vehicle control group.

There was no weight loss in the vehicle group, the TAK-733 (10 mg/kg) group, the MLN8237 (20 or 30 mg/kg) groups, the TAK-733/MLN8237 (20 mg/kg) combination group, or the TAK-733 (10 days) followed by MLN8237 20 mg/kg (for 10 days) group. The mean maximum percent body weight change (BWC) in mice dosed with TAK-733 for 10 days, followed by 1 day of no treatment and then MLN8237 (20 mg/kg) for 10 days was 8.9% on Day 14 of treatment. The mean maximum BWC in the MLN8237 (20 mg/kg) for 10 days followed by one day of no treatment and then TAK-733 for 10 days was 0.9% on Day 14 of treatment.

Synergy analysis revealed a synergistic effect when TAK-733 (10 mg/kg) and MLN8237 (30 mg/kg) were administered concurrently (p<0.05). TAK-733 (10 mg/kg) with MLN8237 at 20 mg/kg concurrent combination dosing and the scheduled dosing were shown to be additive (p>0.05).

No mice were removed from the study during the dosing period. One mouse was removed from the vehicle group before the end of the 99-day study period due to tumor size. Two mice were removed from the MLN8237 20 mg/kg PO QD group due to tumor size. One mouse from the TAK-733 (10 mg/kg) with MLN8237 (30 mg/kg) combination group was found dead and removed from the study after the dosing period (on Day 29). No mice were removed from the study because of body weight loss.

Conclusion

Concurrent combination therapy of oral administered TAK-733 (10 mg/kg) and MLN8237 (30 mg/kg) had significant (p<0.05) enhanced antitumor activity compared to either drug alone in the NCI-H23 human non small cell lung carcinoma tumor xenograft model, with the TAK 733 at 10 mg/kg/day and MLN8237 at 30 mg/kg/day having the highest efficacy and the effect was shown to be synergistic (p<0.05). Intermittent therapy of the combination did not result in any therapeutic advantage over single agent therapy as evidenced by synergy analysis (p>0.05).

Experiment 6

Antitumor Activity of TAK-733 or MLN8237 Administered Orally as Single Agents or in Combination to Female Nude Mice Bearing Panc-1 Human Pancreatic Carcinoma Xenografts The objective of this study was to assess the tumor response activity of TAK-733 or MLN8237 given PO as single agents or in combination in female nude mice bearing Panc-1 xenografts by measuring the treatment induced tumor growth inhibition and body weight loss.

Test and Control Articles: TAK-733 was prepared in 0.5% methylcellulose 400 (MC) (Wako Chemical USA, Richmond, Va., USA) every 5 days and stored at approximately 25° C. in the dark. MLN8237 was prepared in 10% hydroxypropyl-beta-cyclodextrin (HP-β-CD) (Sigma, St. Louis, Mo., USA)+1% NaHCO3 (Sigma, St. Louis, Mo., USA) every 5 days and stored at approximately 25° C. in the dark.

Test System: The animals used in this study are described in Table 8.

TABLE 8

| Test System | |
| --- | --- |
| Species: | *Mus musculus* |
| Strain: | Nude |
| Source: | Harlan Laboratories (Indianapolis, IN, USA) |
| Number of animals per group: | 8 |
| Total number of animals: | 32 |
| Age and sex: | 13-15 weeks at start of dosing, female |
| Weight: | 21 grams at start of dosing |
| Acclimation period: | At least 24 days |

Experimental Design: Low passage (passage TC08) Panc-1 cells (ATCC, Manassas, Va., USA) were grown in Roswell Park Memorial Institute (RPMI)-1640 (ATCC, Manassas, Va., USA) 10% Fetal Bovine Serum (PAA Laboratories PTY LTD, Morningside, QLD, Australia) and supplied at a concentration of 5.0×10$^7$ cells/mLl in Dulbecco's phosphate-buffered saline (DPBS) (Invitrogen-Gibco, Grand Island, N.Y., USA). Cells were mixed 1:1 with Matrigel support (BD Biosciences, Bedford, Mass., USA) and 5.0×10$^6$ Panc-1 cells/animal (0.2 mL injection volume) were implanted SC into the right flank of female Balb/c nude mice.

Tumor growth was monitored twice weekly using calipers and the mean tumor volume was calculated using the formula (0.5×[length×width$^2$]). When the mean tumor volume reached approximately 208 mm³, animals were randomized into treatment groups (n=8/group) and dosed QD, SC with vehicle (HP-β-CD) plus 1% NaHCO₃ and 0.5% methylcellulose), TAK-733 at 10 mg/kg or MLN8237 at 30 mg/kg for 21 days. Tumor size and body weight were measured twice weekly and the study was terminated on Day 63 when tumors in the control group reached approximately 1127.8 mm³. Tumor volumes and BW of animals in the combination treatment group were monitored up to Day 111.

Antitumor activity was determined by calculating the percent TGI ([mean tumor volume of the control group—mean tumor volume of a treated group]/mean tumor volume of the control group) on Day 63. Treatment started on Day 1 and lasted through Day 21. Maximum percent BWL was evaluated during the treatment period (Day 1-Day 21). Antitumor effects were measured as the incidence of complete regressions (CR), partial regressions (PR), the number of tumor-free survivors (TFS) at the end of the study and, tumor growth inhibition (TGI). CRs are defined as tumors that are reduced to below the limit of palpation. Partial regressions (PR) are defined as tumors that are reduced by more than 50% but less than 100% of their initial size. A minimum duration of 7 days is required for a CR or PR to be considered durable. Animals were considered TFS if no measurable tumor was observed at study termination (Day 111), PRs were considered exclusive of CRs, whereas TFS were included in the CR count.

Drug combinations were assessed for synergy using observed AUC values by comparing the ΔAUC observed in the combination group to the sum of the changes observed in both single agents.

Statistical Analysis:

Tumor Growth Inhibition: The change in tumor volume values from the initial treatment day were compared across treatment groups on the last day of treatment to assess whether the differences were statistically significant. A p value <0.05 was considered statistically significant.

Change in the Area Under the Curve (ΔAUC): Statistical analysis was performed with a linear mixed effects regression model. This model takes into account the differences in trends of tumor growth between control and treated samples. Differences among mice were treated as random effects, and a compound symmetry covariance structure was used to model the variability between repeated tumor measurements on each mouse. Treatment comparisons were performed by using the fitted curves from the model to calculate the ΔAUCs. The significance of the ΔAUC was assessed using permutation testing. P-values <0.05 were considered significant.

Combination Treatment Effects: A combination score calculation was used to address the question of whether the effects of the combination treatments were more than additive (synergistic), additive, or subadditive (antagonistic) relative to the individual treatments. The effect of the combination treatment was considered more than additive if the combination score was less than 0, additive if the combination score equaled 0, and subadditive if the combination score was greater than 0, Standard errors and 95% confidence intervals (calculated as 2*SE) were used to determine whether the combination scores were significantly different from 0. P-values <0.05 were considered significant.

Results and Discussion

Tumors in the vehicle-control group grew rapidly and progressively in all surviving mice and reached the median tumor volume (MTV) size of 832 mm³ (2 tumor volume doubling from initial size) in 57.8 days.

Tumor growth was significantly inhibited in the 10 mg/kg TAK-733 (TGI=41.7%, p<0.001) 30 mg/kg MLN8237 (TGI=−6.4%, p<0.001) and the combination treatment groups (TGI=79.1%, p<0.001) when compared to vehicle treatment in Panc-1 cell implanted mice. The combination treatment resulted in a statistically significant antitumor activity (p=0.022) compared to single agent therapies. Partial tumor regressions were observed in two animals in the combination treatment group.

There were no test article treatment-related deaths in this study. TAK-733 (10 mg/kg) and MLN8273 (30 mg/kg) were well tolerated as a single agents with mean maximum body weight losses of 2.0% (Day 5) and 0.2% (Day 5), respectively. Combination therapy of TAK-733 and MLN8237 was also tolerated with observed treatment associated weight loss of 8.7% on Day 9.

There were no treatment related deaths during the study.

Conclusion

Combination therapy with oral administered TAK-733 (10 mg/kg) and MLN8237 (30 mg/kg) was tolerated and showed significantly increased antitumor activity (p=0.022) compared to either drug alone in the Panc-1 human pancreatic carcinoma tumor xenograft model.

Mechanistic studies with A2780 and A375 cells in culture demonstrate slowing of cell cycle progression and increased levels of cell death with the combination of TAK-733 and MLN8237, relative to either agent alone. The increased delay and cell death resulting from the combination result in a shift in the $IC_{50}$ and $IC_{90}$ concentrations of the antiproliferative effect of MLN8237. Combination treatment also results in a reduction of cells with abnormal levels of DNA content relative to MLN8237 alone. These findings are consistent with a mechanism whereby MEK inhibition, in addition to its own deleterious effects on cellular viability, also enhances the deleterious effects of MLN8237 on cellular viability via enhanced killing of cells with abnormal DNA content.

Experiments 1 to 6 demonstrate that the combination of a selective inhibitor of Aurora A kinase with a MEK inhibitor results in enhanced antitumor activity. The clinical study described in Experiment 7 can be carried out to confirm the effectiveness of the combination of a selective inhibitor of Aurora A kinase with a MEK inhibitor in the treatment of patients having cell proliferative disorders.

Experiment 7

Clinical Study

TAK-733 and alisertib are administered on an empty stomach. Patients are instructed to refrain from eating and drinking (except for water and prescribed medications) for 2 hours before and 1 hour after each dose. Each dose of TAK-733 and/or alisertib is given orally with 8 ounces (240 mL) of water. Antacids and calcium-containing supplements cannot be taken for 2 hours prior to until 2 hours after each alisertib dose.

TAK-733 is administered orally QD on Days 1-14 of the 21 day cycle. Alisertib is administered orally BID on Days 1-7 of the 21 day cycle. Patients are instructed to take TAK-733 and alisertib at the same time on the mornings of Days 1-7. A second dose of alisertib is taken in the evenings of Days 1-7 approximately 12 hours after the morning dose. On the mornings of Days 8 through 14, patients take TAK-733 only. A 7-day treatment-free recovery period follows each 14 day dosing period.

An exception to the above administration schedule occurs in Cycle 2 for patients in the PK Expansion Cohort. During Cycle 2, patients in the PK Expansion Cohort are instructed to take alisertib only on the mornings of Days 1-7. A second dose of alisertib is taken in the evening of Days 1-7 approximately 12 hours after the morning dose. On the mornings of Days 8 through 14, patients take TAK-733 only. As for other cycles, a 7-day treatment-free recovery period follows each 14-day dosing period. This alternative schedule allows plasma PK characterization of alisertib in the absence of concomitantly administered TAK-733 and of TAK-733 in the absence of concomitantly administered alisertib.

Patients are instructed to take their study medication at approximately the same time each day and to not take more than the prescribed dose at any time. TAK-733 is taken with the morning dose of alisertib. In the event that a patient fails to take their TAK-733 and/or alisertib doses within the time frame specified, the dose is skipped and considered a missed dose. Patients record any missed doses in a dosing diary and resume dosing at the next scheduled time with the prescribed dosage. Under no circumstances should patients take doses of alisertib less than 6 hours apart.

If severe emesis or mucositis prevents the patient from taking scheduled doses, that dose is skipped. If emesis occurs after study medication ingestion, the dose is not re-administered, and patients resume dosing at the next scheduled time with the prescribed dosage. Patients record the time of the emesis in their dosing diaries. Under no circumstance should a patient repeat a dose or double-up doses.

What is claimed is:

1. A method of treating a patient suffering from a proliferative disorder, comprising administering to the patient a MEK inhibitor in combination with a selective inhibitor of Aurora A kinase that is 4-{[9-chloro-7-(2-fluoro-6-methoxyphenyl)-5H-pyrimido[5,4-d][2]benzazepin-2-yl]amino}-2-methoxybenzoic acid, or a pharmaceutically acceptable salt thereof, wherein the proliferative disorder is selected from the group consisting of lung cancer, ovarian cancer, prostate cancer, pancreatic cancer, gastric cancer, head and neck squamous cell carcinoma, small cell lung cancer, melanoma and colorectal cancer, and wherein the MEK inhibitor is 3-[(2R)-2,3-dihydroxypropyl]-6-fluoro-5-[(2-fluoro-4-iodophenyl)amino]-8-methylpyrido[2,3-d]pyrimidine-4,7(3H,8H)-dione, or a pharmaceutically acceptable salt thereof.

2. The method of claim 1, wherein the proliferative disorder is selected from the group consisting of gastric cancer, head and neck squamous cell carcinoma, small cell lung cancer, melanoma, and colorectal cancer.

3. The method of claim 1, wherein the selective inhibitor of Aurora A kinase is sodium 4-{[9-chloro-7-(2-fluoro-6-methoxyphenyl)-5H-pyrimido[5,4-d][2]benzazepin-2-yl]amino}-2-methoxybenzoate.

4. The method of claim 1, wherein the selective inhibitor of Aurora A kinase and the MEK inhibitor are administered as separate dosage forms and wherein the MEK inhibitor is administered prior to, at the same time as, or following administration of the selective inhibitor of Aurora A kinase.

5. The method of claim 1, wherein the MEK inhibitor and the selective inhibitor of Aurora A kinase are administered in a single dosage form.

6. The method of claim 1, wherein the MEK inhibitor is 3-[(2R)-2,3-dihydroxypropyl]-6-fluoro-5-[(2-fluoro-4-iodophenyl)amino]-8-methylpyrido[2,3-d]pyrimidine-4,7(3H,8H)-dione.

* * * * *